(12) United States Patent
de Sauvage et al.

(10) Patent No.: US 7,393,532 B1
(45) Date of Patent: Jul. 1, 2008

(54) MODULATION OF T CELL DIFFERENTIATION FOR THE TREATMENT OF T HELPER CELL MEDIATED DISEASES

(75) Inventors: Frederic J. de Sauvage, Foster City, CA (US); Iqbal Grewal, Fremont, CA (US); Austin L. Gurney, Belmont, CA (US)

(73) Assignee: Genentech, Inc., South San Francisco, CA (US)

( * ) Notice: Subject to any disclaimer, the term of this patent is extended or adjusted under 35 U.S.C. 154(b) by 424 days.

(21) Appl. No.: 10/088,950

(22) PCT Filed: Oct. 18, 2000

(86) PCT No.: PCT/US00/28827

§ 371 (c)(1),
(2), (4) Date: Mar. 20, 2002

(87) PCT Pub. No.: WO01/29070

PCT Pub. Date: Apr. 26, 2001

(51) Int. Cl.
*A61K 39/395* (2006.01)
*A61K 39/00* (2006.01)

(52) U.S. Cl. .............. 424/144.1; 424/130.1; 424/134.1; 424/143.1; 424/154.1; 424/133.1; 424/178.1; 435/377

(58) Field of Classification Search .............. 424/144.1; 530/387.1, 387.3, 387.9, 388.2, 388.22
See application file for complete search history.

(56) References Cited

U.S. PATENT DOCUMENTS

| | | | |
|---|---|---|---|
| 4,275,149 A | 6/1981 | Litman et al. | |
| 4,816,567 A | 3/1989 | Cabilly et al. | |
| 5,223,409 A | 6/1993 | Ladner et al. | |
| 5,403,484 A | 4/1995 | Ladner et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,571,698 A | 11/1996 | Ladner et al. | |
| 5,585,089 A | 12/1996 | Queen et al. ............. | 424/133.1 |
| 5,625,126 A | 4/1997 | Lonberg et al. | |
| 5,633,425 A | 5/1997 | Lonberg et al. | |
| 5,658,570 A | 8/1997 | Newman et al. | |
| 5,681,722 A | 10/1997 | Newman et al. | |
| 5,693,780 A | 12/1997 | Newman et al. | |
| 5,750,105 A | 5/1998 | Newman et al. | |
| 5,750,373 A | 5/1998 | Garrard et al. | |
| 5,756,096 A | 5/1998 | Newman et al. | |
| 5,792,850 A * | 8/1998 | Baumgartner et al. ...... | 536/23.5 |
| 5,837,242 A | 11/1998 | Holliger et al. .......... | 424/136.1 |
| 5,925,735 A | 7/1999 | Baumgartner et al. ....... | 530/352 |
| 6,080,406 A | 6/2000 | Baumgartner et al. .... | 424/143.1 |
| 6,323,027 B1 * | 11/2001 | Burkly et al. ............... | 435/334 |
| 2004/0219096 A1 * | 11/2004 | De Waal Malefyt et al. ............ | 424/1.41 |
| 2004/0234522 A1 | 11/2004 | DeSauvage et al. ...... | 424/144.1 |
| 2005/0164307 A1 * | 7/2005 | Kojima et al. ................ | 435/7.2 |

FOREIGN PATENT DOCUMENTS

| | | |
|---|---|---|
| WO | WO 97/44455 | 11/1997 |
| WO | WO 99/41095 | * 8/1999 |
| WO | WO 00/28827 | 10/2000 |

OTHER PUBLICATIONS

Lewis (2002), Curr. Opin. Immun. 14: 644-651.*
Lucas et al., (Proc Natl. Acad. Sci. U S A. Dec. 9, 2003; 100(25):15047-52).*
Altschul et al., "Gapped BLAST and PSI-BLAST: A New Generation of Protein Database Search Programs" *Nucleic Acids Research*, 25(17):3389-3402 (1997).
Bazan, J., "Structural Design and Molecular Evolution of a Cytokine Receptor Superfamily" *Proc. Natl. Acad. Sci. USA* 87:6934-6938 (1990).
Boerner et al., "Production of Antigen-Specific Human Monoclonal Antibodies From In Vitro-Primed Human Splenocytes" *The Journal of Immunology* 147(1):86-95 (1991).
Bolton, C., "Recent Advances in the Pharmacological Control of Experimental Allergic Encephalomyelitis (EAE) and the Implications for Multiple Sclerosis Treatment." *Multiple Sclerosis*, 1:143-149 (1995).
Carter et al., "Improved Oligonucleotide Site-Directed Mutagenesis Using M13 Vectors" *Nucl. Acids Res.* 13(12):4431-4443 (Jun. 25, 1985).
Chambers and Allison., "Co-Stimulation in T Cell Responses." *Current Opinion in Immunology*, 9(3):396-404 (Jun. 1997).
Clackson et al., "Making Antibody Fragments Using Phage Display Libraries" *Nature* 352:624-628 (1991).
Cole et al., "The EBV-Hybridoma Technique and Its Application to Human Lung Cancer" *Monoclonal Antibodies and Cancer Therapy*, New York:Alan R. Liss, Inc. pp. 77-96 (1985).
Constant, S.L. et al., "Induction of Th1 and Th2 CD4+ T Cell Responses: The alternative approaches" *Annual Review of Immunology* 15:297-322 (1997).

(Continued)

*Primary Examiner*—Manjunath Rao
*Assistant Examiner*—Daniel C Gamett
(74) *Attorney, Agent, or Firm*—Morrison & Foerster LLP

(57) ABSTRACT

The present invention relates to methods for the treatment and diagnosis of immune related diseases, including those mediated by cytokines released primarily either Th1 or Th2 cells in response to antigenic stimulation. The present invention further relates to methods for biasing the differentiation of T-cells in either the Th1 subtype or the Th2 subtype, based on the relative expression levels of the gene TCCR, and its agonists or antagonists. The present invention further relates to a method of diagnosing Th1- and Th2-mediated diseases.

9 Claims, 14 Drawing Sheets

OTHER PUBLICATIONS

Cosman, D., "The Hematopoietin Receptor Superfamily" *Cytokine* 5(2):95-106 (Mar. 1993).

Finn and Lotze., "Introduction: Third Keystone Symposium on Cellular Immunology and the Immunotherapy of Cancer." *Journal of Immunotherapy*, 21(2):114-118 (Mar. 1998).

Fishwild et al., "High-Avidity Human IgGk Monoclonal Antibodies From a Novel Strain of Minilocus Transgenic Mice" *Nature Biotechnology*, 14(7):845-851 (Jul. 1996).

Heid et al., "Real time quantitative PCR" *Genome Research* 6(10):986-994 (1996).

Hoogenboom and Winter, "By-Passing Immunisation: Human Antibodies from Synthetic Repertoires of Germline $V_H$ Gene Segments Rearranged in Vitro" *J. Mol. Biol.* 227:381-388 (1992).

Hsieh, C.S. et al., "Development of $T_H$ 1 CD4$^+$T Cells Through IL-12 Produced by Listeria-Induced Macrophages" *Science* 260:547-549 (1993).

Jenkins, M., "The Ups and Downs of T Cell Costimulation." *Immunity*, 1(6):443-446 (Sep. 1994).

Jones et al., "Replacing the Complementarity-Determining Regions in a Human Antibody with those from a Mouse" *Nature* 321:522-525 (May 29, 1986).

June et al., "The B7 and CD28 Receptor Families." *Immunology Today*, 15(7):321-331 (Jul. 1994).

Kaplan, M. H. et al., "Impaired IL-12 responses and enhanced development of Th2 cells in Stat4-deficient mice" *Nature* 382:174-177 (1996).

Kohler, G. and Milstein, C., "Continuous Cultures of Fused Cells Secreting Antibody of Predefined Specificity" *Nature* 256:495-497 (Aug. 7, 1975).

Kuhn, R. et al., "Generation and analysis of interleukin-4 deficient mice" *Science* 254:707-710 (1991).

Kwon et al., "Manipulation of T Cell Costimulatory and Inhibitory Signals for Immunotherapy of Prostate Cancer." *Proc. Natl. Acad. Sci. USA* 94(15):8099-8103 (Jul. 22, 1997).

Le Gros, G. et al., "Generation of Interleukin 4 (IL-4) -producing Cells In Vivo and In Vitro: IL-2 and IL-4 Are Required For In Vivo Generation of IL-4-producing Cells" *Journal of Experimental Medicine* 172:921-929 (1990).

Linsley and Ledbetter., "The Role of the CD28 Receptor During T Cell Responses to Antigen." *Annu. Rev. Immunol.* 11:191-212 (1993).

Lonberg and Huszar., "Human Antibodies From Transgenic Mice" *International Reviews of Immunology* 13(1):65-93 (1995).

Lonberg et al., "Antigen-Specific Human Antibodies From Mice Comprising Four Distinct Genetic Modifications" *Nature.* 368(6474):856-859 (Apr. 28, 1994).

Lynch et al., "Flt3 Ligand Induces Tumor Regression and Antitumor Immune Responses In Vivo." *Nature Medicine*, 3(6):625-631 (Jun. 1997).

Magram, J. et al., "IL-12-deficient mice are defective in IFNγ production and type 1 cytokine responses" *Immunity* 4:471-481 (1996).

Marks et al., "By-Passing Immunization: Building High Affinity Human Antibodies by Chain Shuffling" *Bio/Technology* 10:779-783 (1992).

Marks et al., "By-Passing Immunization: Human Antibodies From V-gene Libraries Displayed On Phage" *J. Mol. Biol.* 222:581-597 (1991).

Melero et al., "Monoclonal Antibodies Against the 4-1BB T-cell Activation Molecule Eradicate Established Tumors." *Nature Medicine*, 3(6):682-685 (Jun. 1997).

Morrison, S., "Immunology: Success in Specification" *Nature .* 368(6474):812-813 (Apr. 28, 1994).

Neuberger, M., "Generating High-Avidity Human Mabs in Mice" *Nature Biotechnology*, 14(7):826 (Jul. 1996).

Noben-Trauth, N. et al., "An interleukin 4 (IL-4)-independent pathway for CD4+ T cell IL-4 production is revealed in IL-4 receptor-deficient mice" *Proc. Natl. Acad. Sci. USA* 94:10838-10843 (1997).

O'Garra, A., "Cytokines induce the development of functionally heterogeneous T helper cell subsets" *Immunity* 8:275-283 (1998).

Presta, L., "Antibody Engineering" *Curr. Op. Struct. Biol.* 2:593-596 (1992).

Riechmann et al., "Reshaping Human Antibodies for Therapy" *Nature* 332:323-327 (Mar. 24, 1988).

Romagnani, S. et al., "Human Th1 and Th2 cells: functional properties, mechanisms of development and role in diseases" *Allergologie*, Muenchen-DeisenhDE:Dustri Verlag vol. 18(4):175-179 (1996).

Schwartz, R., "Costimulation of T Lymphocytes: The Role of CD28, CTLA-4, and B7/BB1 in Interleukin-2 Production and Immunotherapy." *Cell.* 71(7):1065-1068 (Dec. 24, 1992).

Seder, R.A. et al., "Interleukin 12 acts directly on CD4+ T cells to enhance priming for interferon γ production and diminishes interleukin 4 inhibition of such priming" *Proc. Natl. Acad. Sci. USA* 90:10188-10192 (1993).

Shimoda, K. et al., "Lack of IL-4-induced Th2 response and IgE class switching in mice with disrupted Stat6 gene" *Nature* 380:630-633 (1996).

Sprecher et al., "Cloning and Characterization of a Novel Class 1 Cytokine Receptor" *Biochem. & Biophys. Res. Comm.* 246:82-90 (1998).

Swain et al., "Helper T-cell subsets: phenotype, function and the role of lymphokines in regulating their development" *Immunol. Rev.* 123:115-144 (1991).

Thimmappaya et al., "Adenovirus VAI RNA is required for efficient translation of viral mRNAs at late times after infection" *Cell* 31(3 Pt 2):543-551 (Dec. 1982).

Umetsu and DeKruyff, "Th1 and Th2 CD4+ Cells in the Pathogenesis of Allergic Diseases" *Soc. Exp. Biol. Med.* 215:11-20 (1997).

Urdal, D.L., "Cytokine Receptors" *Ann. Reports Med. Chem.*, Chapter 23, 26:221-228 (1991).

Wells et al., "Cassette Mutagenesis: An Efficient Method for Generation of Multiple Mutations at Defined Sites" *Gene*, 34(2-3):315-323 (1985).

Wells et al., "Importance of Hydrogen-Bond Formation in Stabilizing the Transition State of Subtilisin" *Philos. Trans. Royal Soc. London Ser. A* 317:415-423 (1986).

Wu, C. et al., "Characterization of IL-12 receptor β1 chain (IL-12Rβ1)-deficient mice" *J. Immunol.* 159:1658-1665 (1997).

Zoller and Smith., "Oligonucleotide-Directed Mutagenesis Using M13-Derived Vectors: An Efficient and General Procedure for the Production of Point Mutations in Any Fragment of DNA" *Nucl. Acids Res.* 10(20):6487-6500 (1982).

Benjamini, 2000, *Immunology* -A Short Course, 4$^{th}$ *Ed., Wiley-Liss Pubs*, p. 60.

Heldin et al., 1995, *Cell*, 80(2):213-23 "Dimerization of Cell Surface Receptors in signal transduction".

Huang, 2000, *Pharmacol. Therapeutics*, 86: 201-215 "Structural chemistry and therapeutic intervention of protein-protein interactions in immune response, human immunodeficiency virus entry, and apoptosis".

Huhtaniemi, 2002, *Molecular and Cellular Endocrinology*, 187: 49-56 "Transgenic and knockout mouse models for the study of luteinizing hormone and luteinizing hormone receptor function".

Lederman et al., 1991, *Molecular Immunology*, 28: 1171-1181 "A Single Amino Acid Substitution in a Common African Allele of the CD4 Molecule Ablates Binding of the Monoclonal Antibody, OKT4".

Mak et al., 2001, *Nat. Rev. Immunol*, 1: 11-19 "Knockout Mice: A Paradigm Shift in Modern Immunology".

Merriam-Webster Online Dictionary - Main Entry: Prevent.

NCBI Listing of nucleotide and protein sequences for TCCR, dated Nov. 25, 2002.

O'Shea et al., 2002, *Nat. Rev. Immuno.*, 2:37-45 "Cytokines and Autoimmunity".

Paul, W.E.., 2003, *Fundamental Immunology, 5$^{th}$ Edition*. Lippincott Williams and Wilkins, Pub, pp. 716 and 735.

Proudfoot et al., 2000, *Immunol. Rev.* , 177:246-256 "The strategy of blocking the chemokine system to combat disease".

Rudikoff et al., 1982, *Proc. Natl.Acd Sci. USA* , 79:1979 "Single amino acid substitution altering antigen-binding specificity".

Stewart et al., 1992, *Nature*, 359:76-79 "Blastocyst implantation depends on maternal expression of leukaemia inhibitory factor".

\* cited by examiner

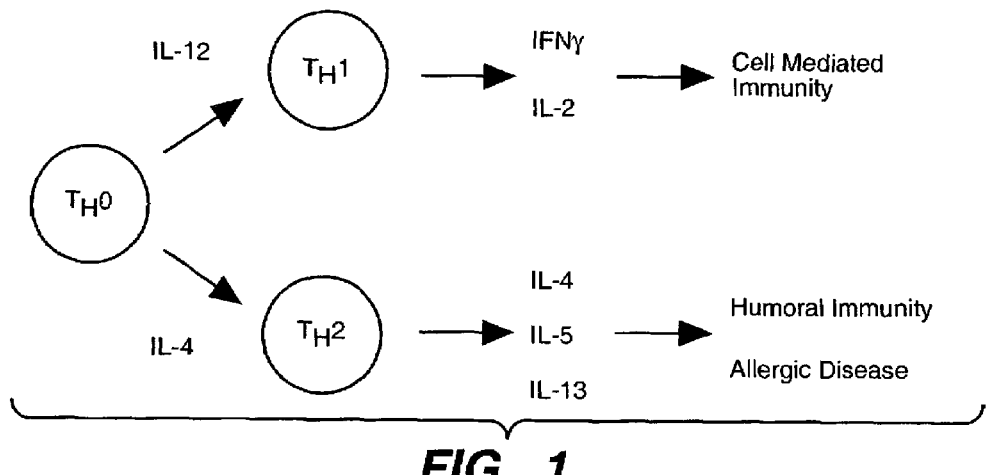
FIG._1
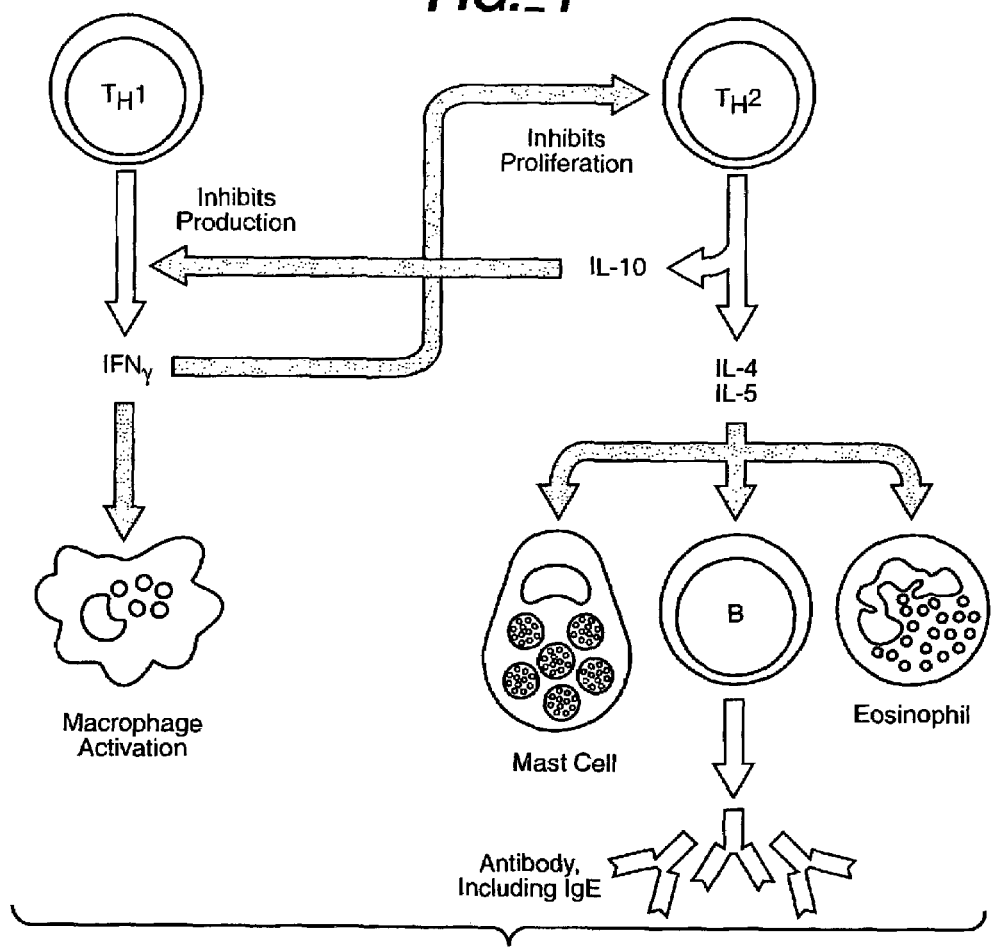
FIG._2

MRGGRGAPFWLWPLPKLALLPLLWVLFQRTRPQGSAGPLQCYGVGPLGDLNCSWEPLGD
LGAPSELHLQSQKYRSNKTQTVAVAAGRSWVAIPREQLTMSDKLLVWGTKAGQPLWPPV
FVNLETQMKPNAPRLGPDVDFSEDDPLEATVHWAPPTWPSHRVLICQFHYRRCQEAAWT
LLEPELKTIPLTPVEIQDLELATGYKVYGRCRMEKEEDLWGEWSPILSFQTPPSAPKDV
WVSGNLCGTPGGEEPLLLWKAPGPCVQVSYKVWFWVGGRELSPEGITCCCSLIPSGAEW
ARVSAVNATSWEPLTNLSLVCLDSASAPRSVAVSSIAGSTELLVTWQPGPGEPLEHVVD
WARDGDPLEKLNWVRLPPGNLSALLPGNFTVGVPYRITVTAVSASGLASASSVWGFREE
LAPLVGPTLWRLQDAPPGTPAIAWGEVPRHQLRGHLTHYTLCAQSGTSPSVCMNVSGNT
QSVTLPDLPWGPCELWVTASTIAGQGPPGPILRLHLPDNTLRWKVLPGILFLWGLFLLG
CGLSLATSGRCYHLRHKVLPRWVWEKVPDPANSSSGQPHMEQVPEAQPLGDLPILEVEE
MEPPPVMESSQPAQATAPLDSGYEKHFLPTPEELGLLGPPRPQVLA

*FIG._3*

MNRLRVARLTPLELLLSLMSLLLGTRPHGSPGPLQCYSVGPLGILNCSWEPLGDLETPPV
LYHQSQKYHPNRVWEVKVPSKQSWVTIPREQFTMADKLLIWGTQKGRPLWSSVSVNLETQ
MKPDTPQIFSQVDISEEATLEATVQWAPPVWPPQKALTCQFRYKECQAEAWTRLEPQLKT
DGLTPVEMQNLEPGTCYQVSGRCQVENGYPWGEWSSPLSFQTPFLDPEDVWVSGTVCETS
GKRAALLVWKDPRPCVQVTYTVWFGAGDITTTQEEVPCCKSPVPAWMEWAVVSPGNSTSW
VPPTNLSLVCLAPESAPCDVGVSSADGSPGIKVTWKQGTRKPLEYVVDWAQDGDSLDKLN
WTRLPPGNLSTLLPGEFKGGVPYRITVTAVYSGGLAAAPSVWGFREELVPLAGPAVWRLP
DDDPPGTPVVAWGEVPRHQLRGQATHYTFCIQSRGLSTVCRNVSSQTQTATLPNLHSGSFK
LWVTVSTVAGQGPPGPDLSLHLPDNRIRWKALPWFLSLWGLLLMGCGLSLASTRCLQARC
LHWRHKLLPQWIWERVPDPANSNSGQPYIKEVSLPQPPKDGPILEVEEVELQPVVESPKA
SAPIYSGYEKHFLPTPEELGLLV

*FIG._4*

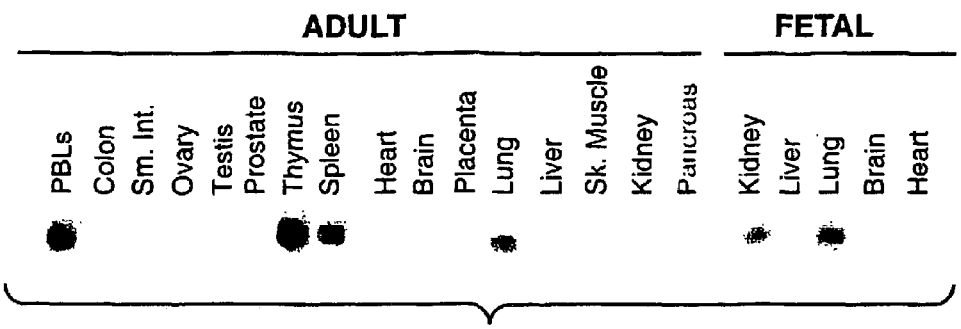

*FIG._6*

| | | |
|---|---|---|
| h-TCCR | 1 | MRGGRGAPFWLWPLPKLALLPLLWVLFQRTRPQGBAGPLQCYGVGPLGDL |
| m-TCCR | 1 | ----MNRLRVARLTPLELLSLMSELLGTRPHGSPGPLQCYSVGPLGLL |
| h-TCCR | 51 | NCSWEPLGDLGAPSELHLQSQKYRSNKTQTVAAAGRSWVAIPREQLTMS |
| m-TCCR | 46 | NCSWEPLGDLETPPVLYHQSQKIHPNRVWEVKVPSKQSWVTIPREQFTMA |
| h-TCCR | 101 | DKLLVWGTKAGQPLWPPVFVNLETQMKRNAPRLGPDVDFSEDDPLEATVH |
| m-TCCR | 96 | DKLLIWGTQKGRPLWSSVSVNLETQMKPDTPQIFSQVDISEATLEATVQ |
| h-TCCR | 151 | WAPPTWPSHKVLICQFHYRRCQEAAWTLLEPELKTIPLTPVEIQDLELAT |
| m-TCCR | 146 | WAPPVWPPQKALTCQFRYKECQAEAWTRLEPQLKTDGLTPVEMQNLEPGT |
| h-TCCR | 201 | GYKVYGRCMEKEEDLWGEWSPILSFQTPPSAPKDVWVSGNLCGTPGGEE |
| m-TCCR | 195 | CYQVSGRCQVENGYP-WGEWSSPLSFQTPFLDPEDVWVSGTVCETSGKRA |
| h-TCCR | 251 | PLLWKAPGPCYQVSYKVNFWVGGRELSPEGITCCCSLIPSGAEWARVSA |
| m-TCCR | 245 | ALLVWKDPRPCVQVTYTVWFGAGDITTTQEEVPCCKSPVPAWMEWAVVSP |
| h-TCCR | 301 | VNATSWEPLTNLSLVCLDSASAPRSVAVSSIAGSTELLIVTWQPGPGEPLE |
| m-TCCR | 295 | GNSTSWVPPTNLSLVCLAPESAPCDVGSSADGSPGIKVTWKQGTRKPLE |
| h-TCCR | 351 | HVVDWARDGDPLEKINWVRLPPGNLSALLPGNFTVGVPYRITVTAVSASG |
| m-TCCR | 345 | YVVDWAQDGDSLDKLNWTRIPPGNLSTLLPGERFKGGVPYRITVTAVYSGG |
| h-TCCR | 401 | LASASVWGFREELAPLVGPTLWRLQDAPPGTPAIAWGEVPRHQLRGHLT |
| m-TCCR | 395 | LAAAPSVWGFREELVPLAGPAVWRLPDDPPGTPVVAWGEVPRHQLRGQAT |
| h-TCCR | 451 | HYTLCAQSGTSPSVCMNVSGNTQSVTLPDLPWGPCELWVTASTIAQGPP |
| m-TCCR | 445 | HYTFCIQSRGLSTVCRNVSSQTQTATLPNLHSGSFKLWVTSVAGQGPP |
| h-TCCR | 501 | GPILRLHLPDNTLRWKVLPGILFLWGLFLLGCGLSLATS----GRCYHLR |
| m-TCCR | 495 | GPDLSLHLPDWRIRWKALPWFLSLWGLLLMGCGLSLASTRCLQARCLEWR |
| | | TM |
| h-TCCR | 547 | HKVLPRWVEKIVPDPANSISSGQPHMEQVPEAQPLGDLPILEVEEMEPPV |
| m-TCCR | 545 | HKLLPQWIWERVPDPANSNSGQPYIKEVSLPQPPKDGPILEVEEVELQPV |
| | | Box 1      TM |
| h-TCCR | 597 | MESSQPAQATAPLDSGYEKHFLPTPEELGLLGPPRPQVLA |
| m-TCCR | 595 | VES----PKASAPIYSGYEKHFLPTPEELGLLV |

FIG._5

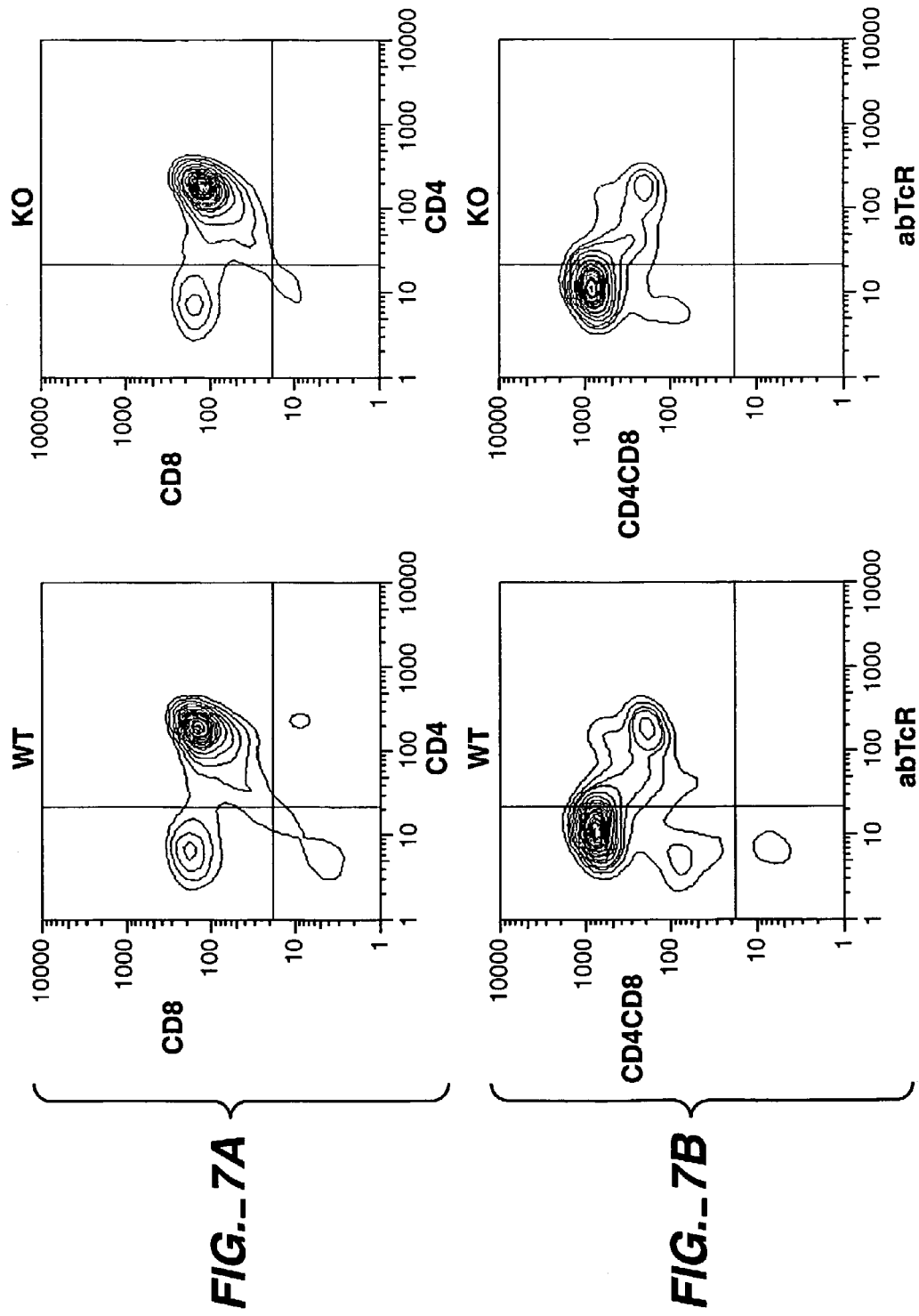
FIG._7A
FIG._7B

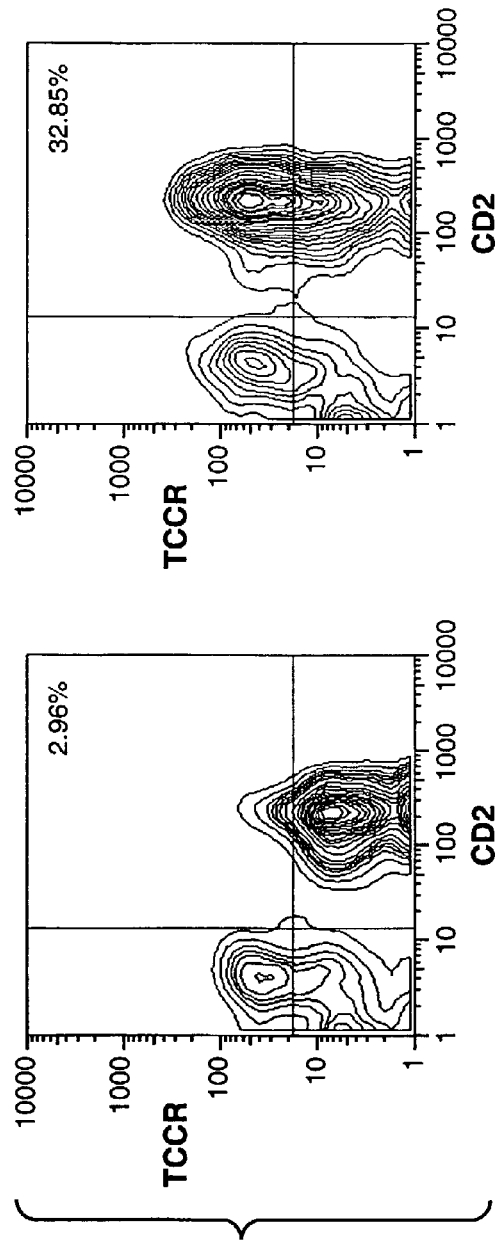
FIG._8A
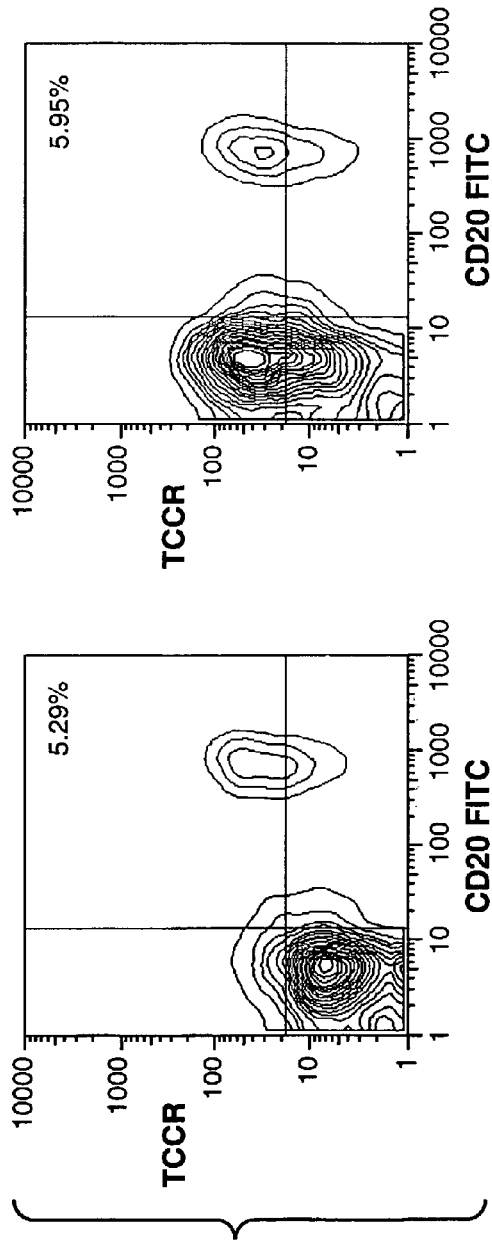
FIG._8B

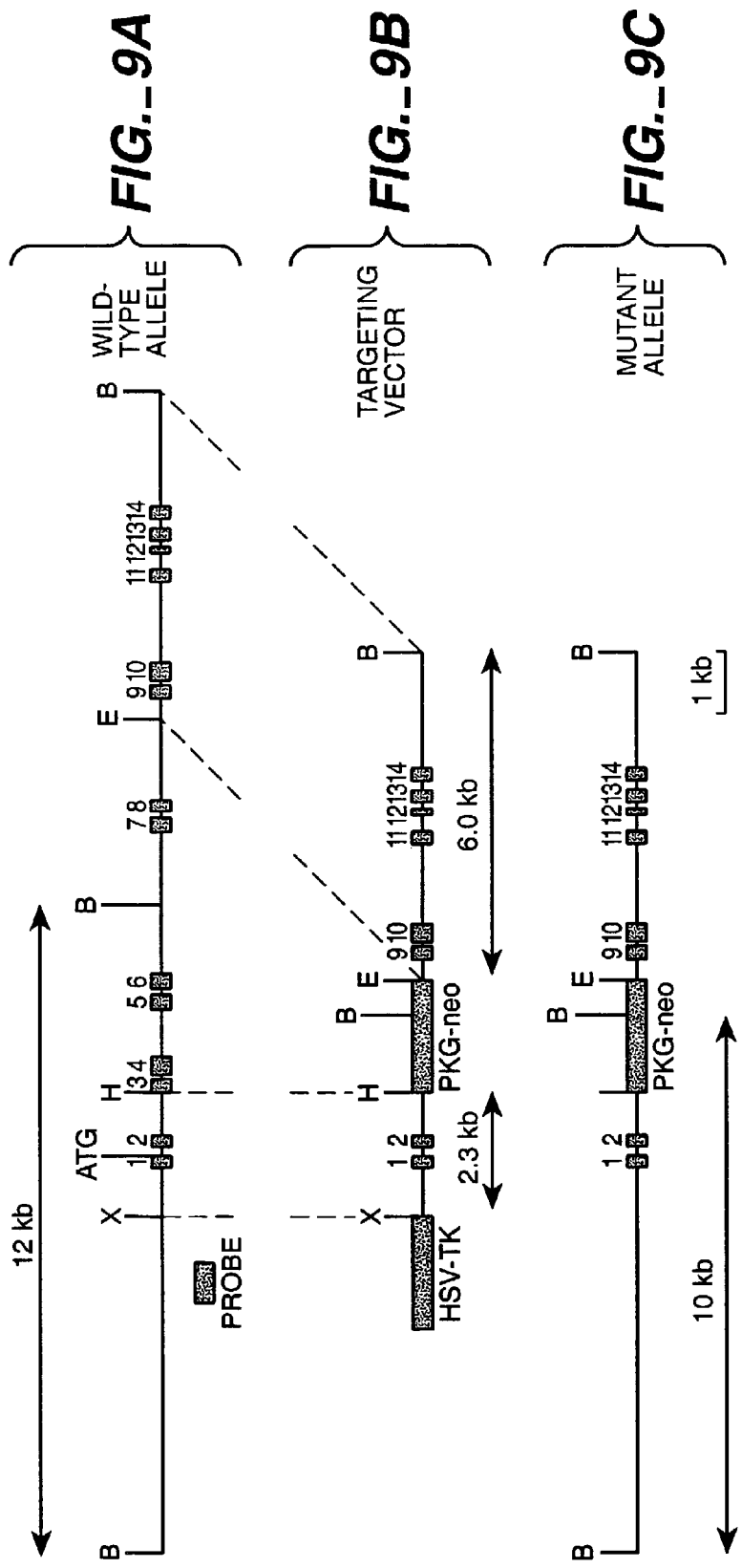

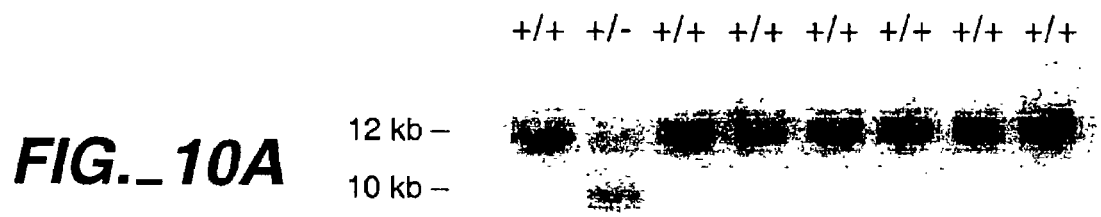
FIG._10A
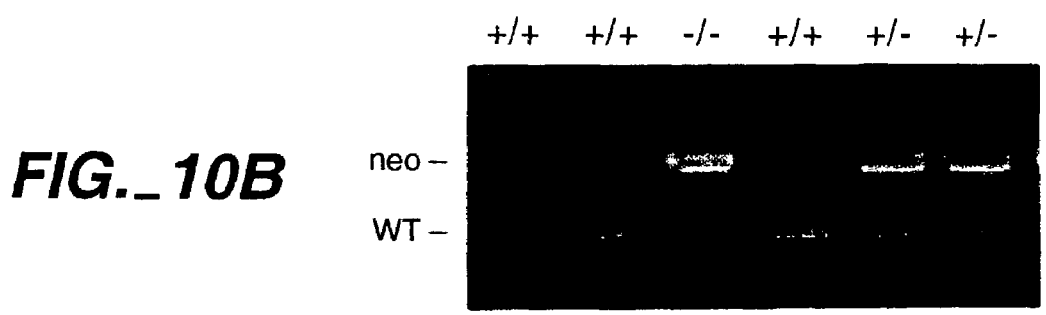
FIG._10B
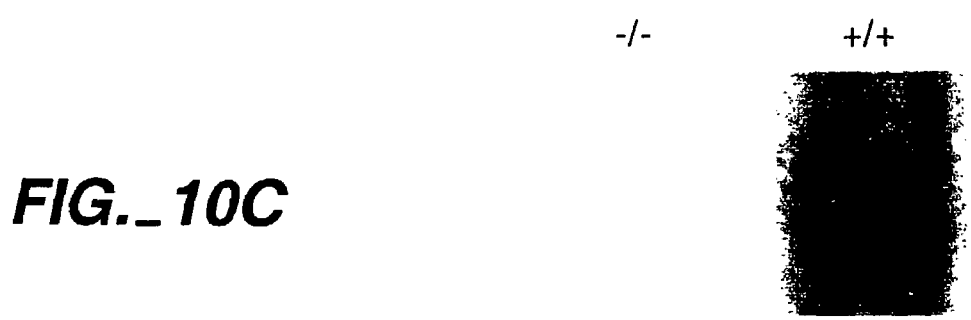
FIG._10C

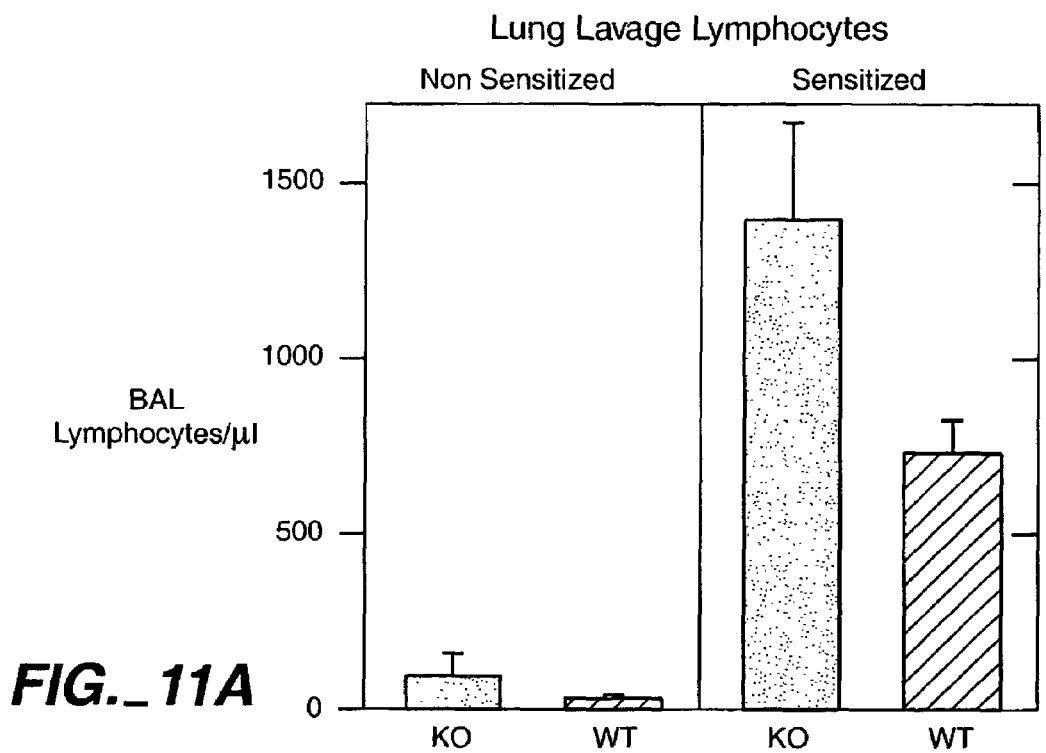
FIG._11A
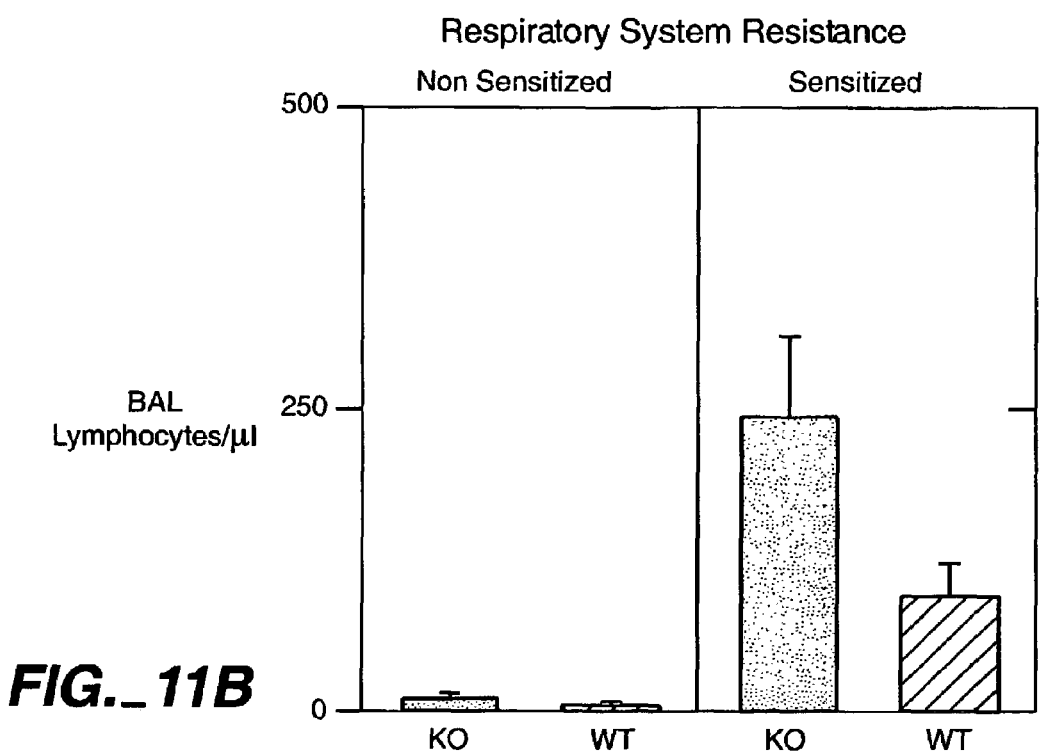
FIG._11B

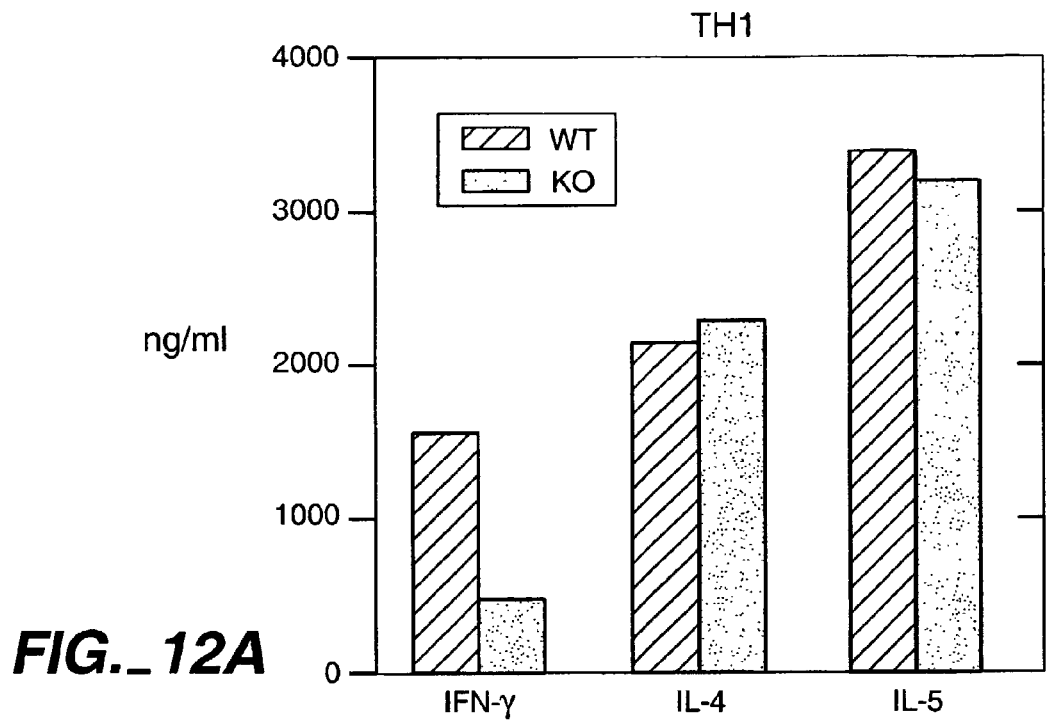
FIG._12A
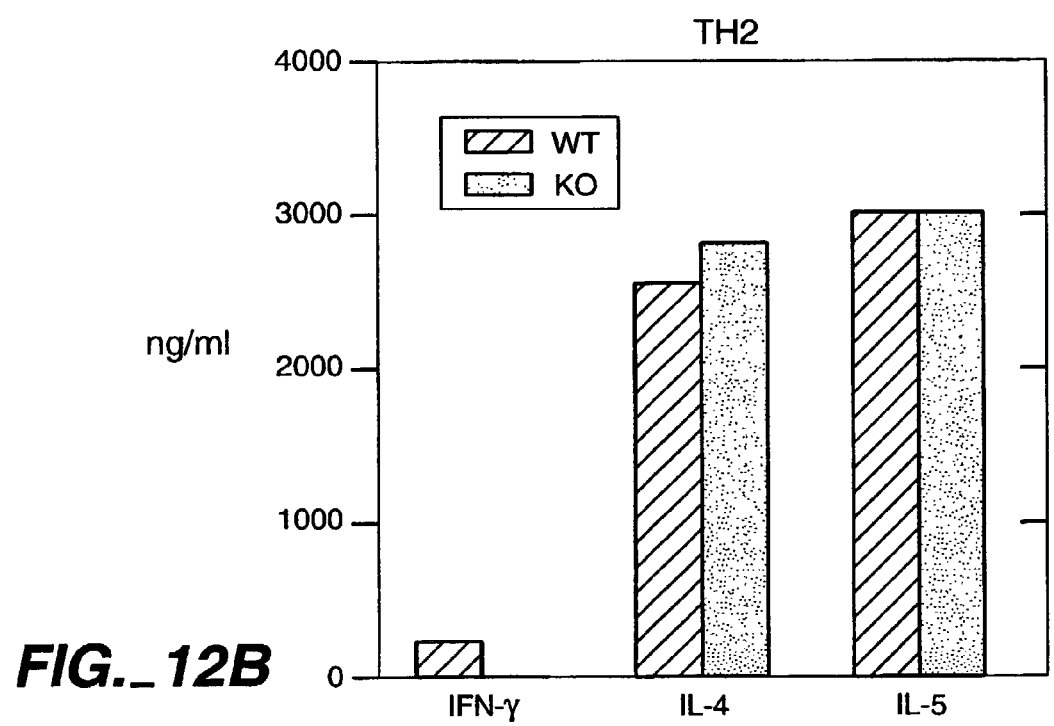
FIG._12B

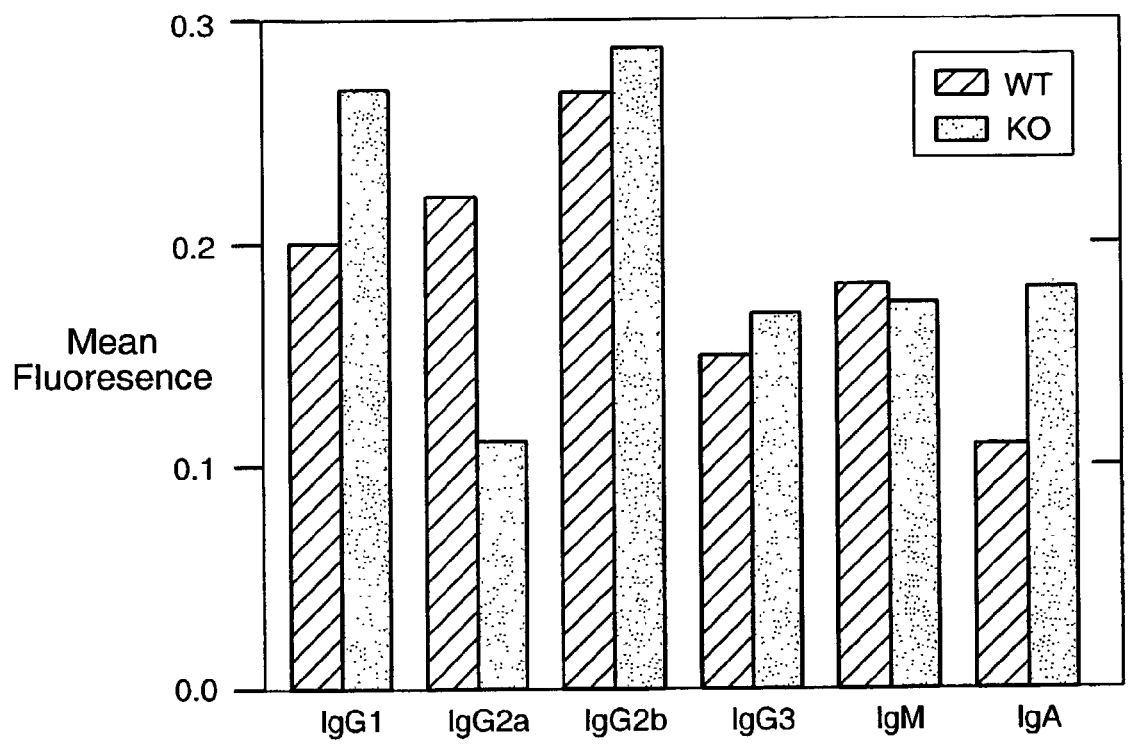
FIG._13
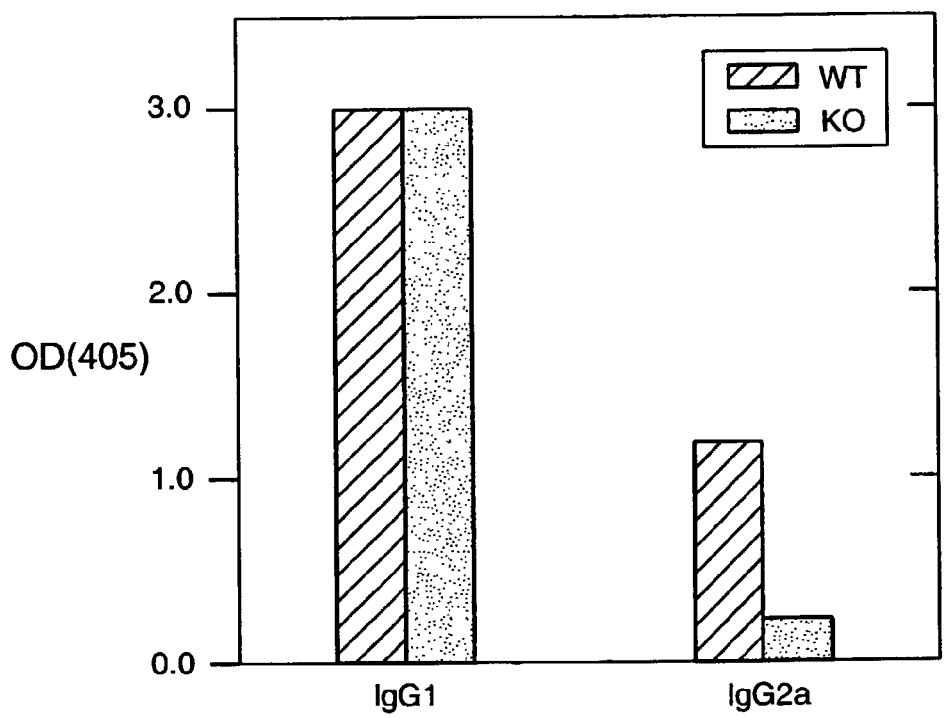
FIG._14

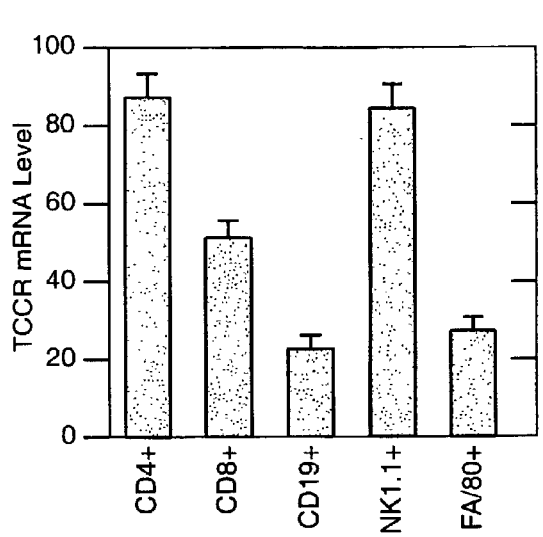
FIG._15A
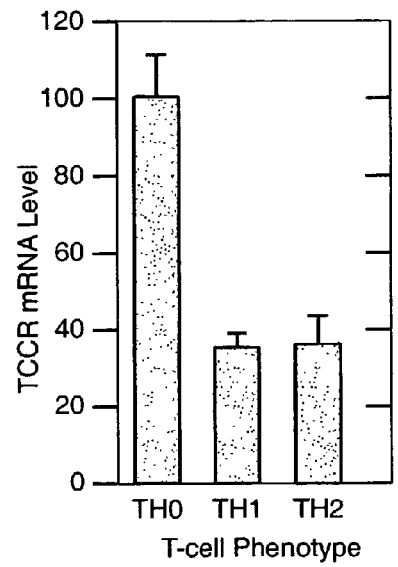
FIG._15B
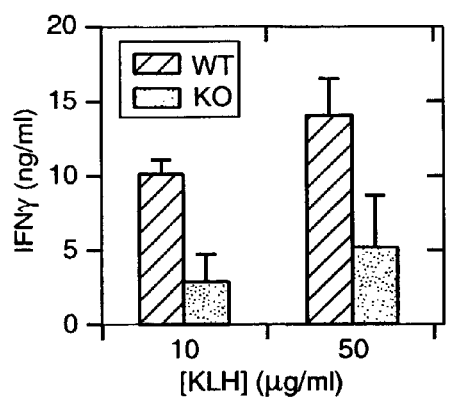
FIG._16A
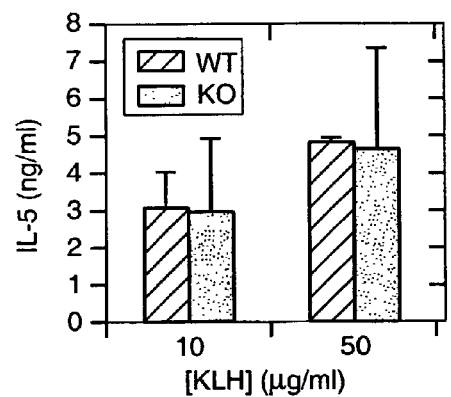
FIG._16C
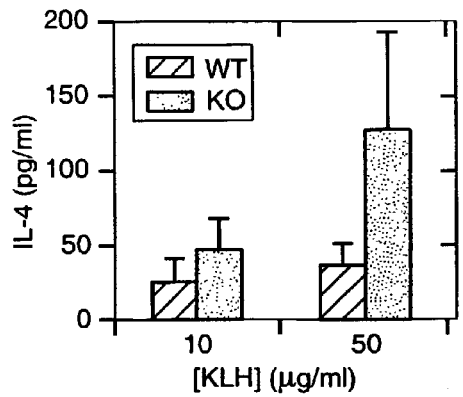
FIG._16B
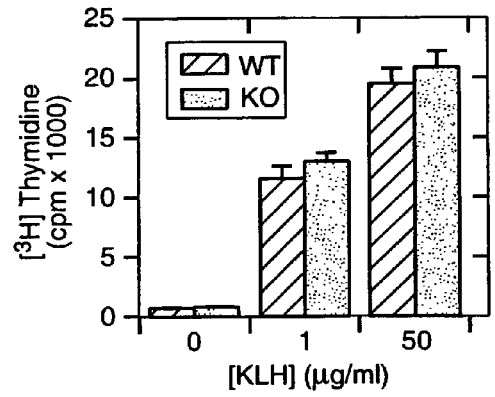
FIG._16D

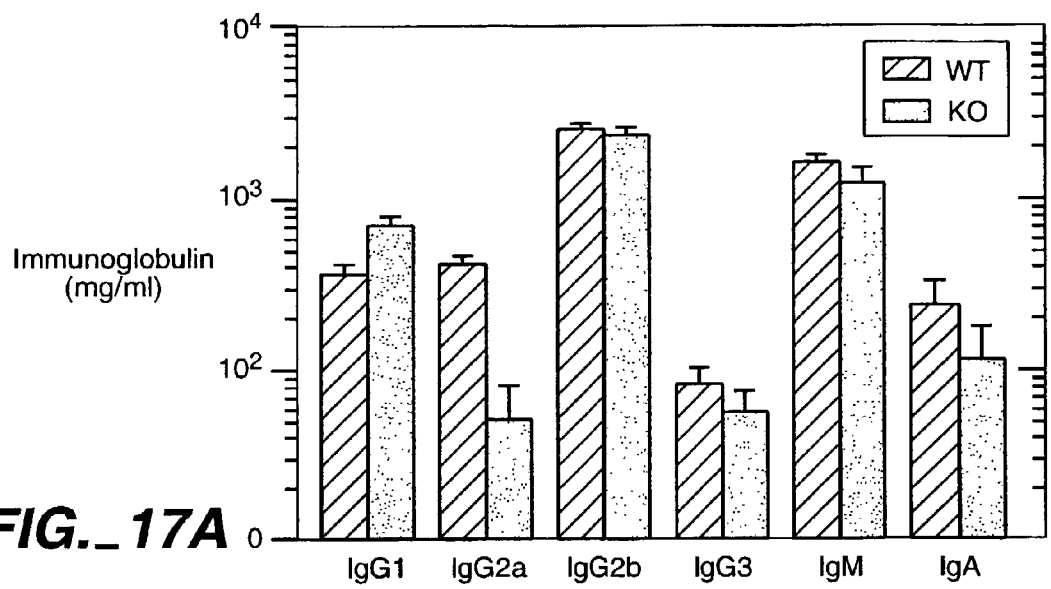
FIG._17A
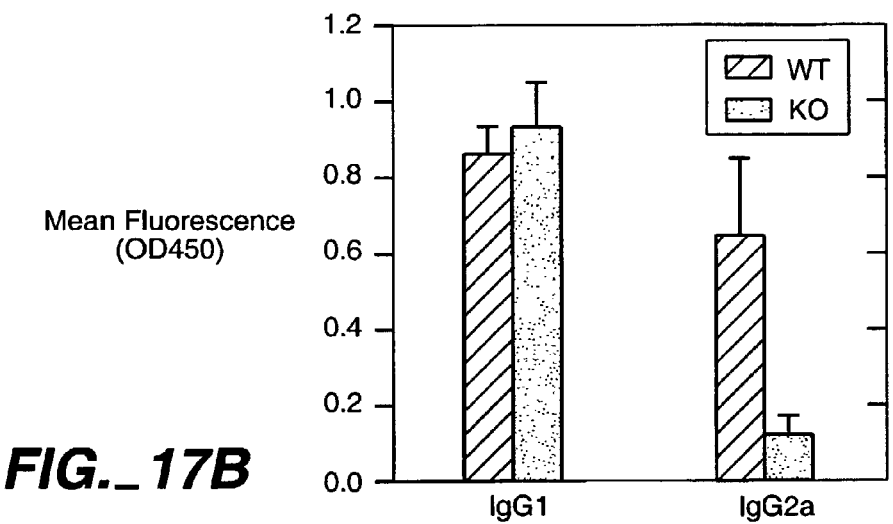
FIG._17B
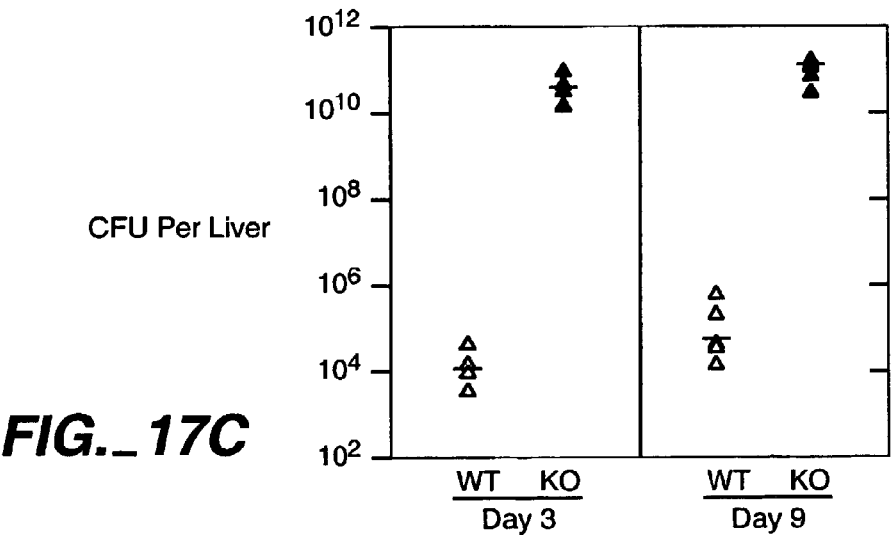
FIG._17C

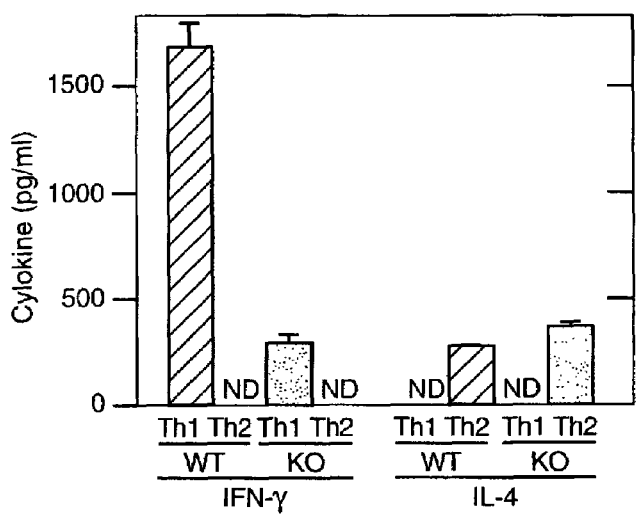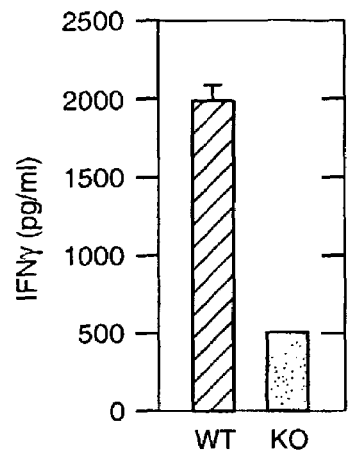
FIG._18A  FIG._18B
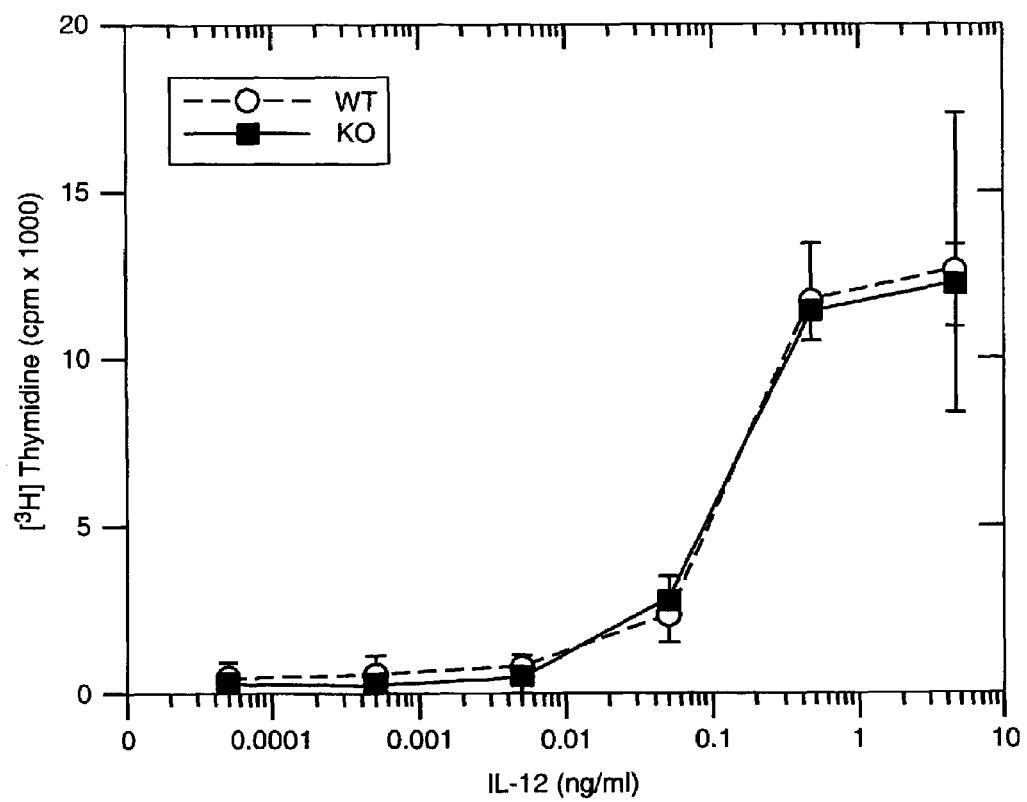
FIG._18C

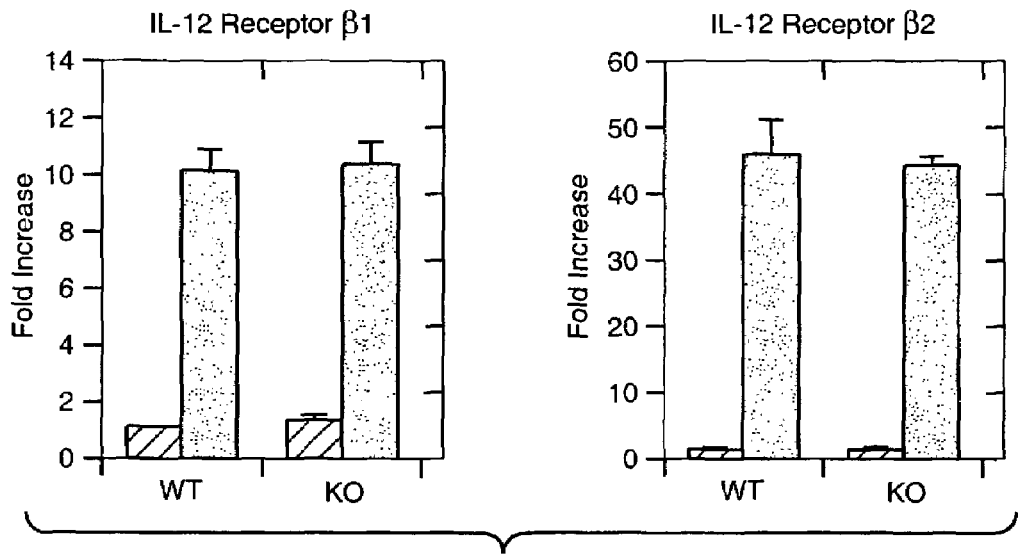

FIG._18D

| Primer / Probe | Sequence | SEQ ID NO: |
|---|---|---|
| mTCCR, sense, Taqman | TGGTCTCTCCTGGCAACAGC | 5 |
| mTCCR, as, Taqman | AGCCAAGCACACCAGAGACA | 6 |
| mTCCR, Taqman probe | CAGCTGGGTGCCTCCCACCAA | 7 |
| mRPL19, sense, Taqman | ATCCGCAAGCCTGTGACTGT | 8 |
| mRPL19, as, Taqman | TCGGGCCAGGGTGTTTTT | 9 |
| mRPL19, Taqman probe | TTCCCGGGCTCGTTGCCG | 10 |
| mIL12Rb1, sense, Taqman | TCGCGTCTCTGGGAAGCT | 11 |
| mIL12Rb1, as, Taqman | TTTAAGCCAATGTATCCGAGACTG | 12 |
| mIL12Rb1, Taqman probe | CGCCAGCGTCCTCCTCGTGG | 13 |
| mIL12Rb2, sense, Taqman | CAAGCATTTGCATCGCTATCA | 14 |
| mIL12Rb2, as, Taqman | AATGCCTTTTGCCGGAAGT | 15 |
| mIL12Rb2, Taqman probe | ACGAATTGAGAACGTGCCCACCGT | 16 |

FIG._19

MODULATION OF T CELL DIFFERENTIATION FOR THE TREATMENT OF T HELPER CELL MEDIATED DISEASES

FIELD OF THE INVENTION

The present invention relates generally to the identification and isolation of novel DNA, the recombinant production of novel polypeptides, and to compositions and methods for the diagnosis and treatment of immune related diseases, specifically to methods of modulating the T-cell differentiation and cytokine release profiles into Th1 subtype and Th2 subtypes, and the host of disorders that are implicated by the release of the cytokine profiles.

BACKGROUND OF THE INVENTION

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e. lymphokines, which play a central role in the activation of B cells, cytotoxic T cells and a variety of other cells which participate in the immune response.

A central event in both humoral and cell mediated immune responses is the activation and clonal expansion of helper T cells. Helper T cell activation is initiated by the interaction of the T cell receptor (TCR)—CD3 complex with an antigen-MHC on the surface of an antigen presenting cell. This interaction mediates a cascade of biochemical events that induce the resting helper T cell to enter a cell cycle (the G0 to G1 transition) and results in the expression of a high affinity receptor for IL-2 and sometimes IL-4. The activated T cell progresses through the cycle proliferating and differentiating into memory cells or effector cells.

The immune system of mammals consists of a number of unique cells that act in concert to defend the host from invading bacteria, viruses, toxins and other non-host substances. The cell type mainly responsible for the specificity of the immune system is called the lymphocyte, of which there are two types, B and T cells. T cells take their designation from being developed in the thymus, while B cells develop in the bone marrow. The T-cell population has several subsets, such as suppressor T cells, cytotoxic T cells and T helper cells. The T-helper cell subsets define 2 pathways of immunity: Th1 and Th2. The Th1 cells, a functional subset of CD4+ cells, are characterized by their ability to boost cell mediated immunity. The Th1 cell produces cytokines Il-2 and interferon-γ, and are identified by the absence of Il-10, Il-4, Il-5 and Il-6.

The Th2 cell is also a CD4+ cell, but is distinct from the Th1 cell. The Th2 cells are responsible for antibody production and produce the cytokines Il-4, Il-5, Il-10 and Il-13. (see FIG. 1). These cytokines play an important role in making the Th1 and Th2 responses mutually inhibitory. The interferon-γ that is produced by the Th1 cells inhibits the proliferation of Th2 cells (FIG. 2) while IL-10 produced by the Th2 cells represses the production of interferon-γ (FIG. 2).

Members of the four helical bundle cytokine family (Bazan, J. F., 1990, *Proc Natl Acad Sci USA*, 87:6934-8) have been found to play a critical role in the expansion and terminal differentiation of T helper cells from a common precursor into distinct populations of Th1 and Th2 effector cells. O'Garra, A., 1998, *Immunity*, 8:275-83. IL-4 influence predominantly the development of Th2 cells while IL-12 is a major factor involved in the differentiation of Th1 cells. Hsieh, C. S., et al., 1993, *Science*, 260:547-9; Seder, R. A., et al., 1993, *Proc Natl Acad Sci USA*, 90:10188-92; Le Gros, G., et al., 1990, *J Exp Med*, 172:921-9; Swain, S. L., et al., 1991, *Immunol Rev*, 123:115-44. Accordingly, mice deficient in IL-4 (Kuhn, R., et al, 1991, *Science*, 254:707-10), IL-4 receptor chain (Noben-Trauth, N., et al., 1997, *Proc Natl Acad Sci USA*, 94:10838-43), or the IL-4 specific transcription factor STAT6 (Shimoda, K., et al., 1996, *Nature*, 380:630-3) are defective in Th2 responses, while mice deficient in IL-12 (Magram, J., et al., 1996, *Immunity*, 4:471-81), IL-12 receptor (IL-12R) 1 chain (Wu, C., et al., 1997, *J Immunol*, 159:1658-65), or the IL-12 specific transcription factor STAT4 (Kaplan, M. H., et al., 1996, *Nature*, 382:174-7) have impaired Th1 responses.

Th-1 and Th-2 cell subtypes are believed to be derived from the common precursor, termed a Th-0 cell. In contrast to the mutually exclusive cytokine production of the Th-1 and Th-2 subtypes, Th-0 cells produce most or all of these cytokines. The release profiles of the different cytokines for the Th-1 and Th-2 subtypes plays an active role in the selection of effector mechanisms and cytotoxic cells. The Il-2 and γ-interferon secreted by Th-1 cells tends to activate macrophages and cytotoxic cells, while the Il-4, Il-5, Il-6 and Il-10 secreted by Th-2 cells tends to increase the production of eosinophils and mast cells as well as enhance the production of antibodies including IgE and decrease the function of cytotoxic cells. Once established, the Th-1 or Th-2 response pattern is maintained by the production of cytokines that inhibit the production of the other subset. The γ-interferon produced by Th-1 cells inhibits production of Th-2 cytokines such as Il-4 and Il-10, while the Il-10 produced by Th-2 cells inhibits the production of Th-1 cytokines such as Il-2 and γ-interferon.

The upset of the delicate balance between the cytokines produced by the Th1 and Th2 cell subsets leads to a host of disorders. For example, the overproduction of Th1 cytokines can lead to autoimmune inflammatory diseases, multiple sclerosis and inflammatory bowel disease (e.g., Crohn's disease, regional enteritis, distal ileitis, granulomatous enteritis, regional ileitis, terminal ileitis). Similarly, overproduction of Th2 cytokines leads to allergic disorders, including anaphylactic hypersensitivity, asthma, allergic rhinitis, atopic dermatitis, vernal conjunctivitis, eczema, urticaria and food allergies. Umetsu et al., *Soc. Exp. Biol. Med.* 215: 11-20 (1997).

WO 97/44455 filed 19 May 1997 and Sprecher et al., *Biochem. Biophys. Res. Commun.* 246: 82-90 (1998) describe cytokine receptor molecules possessing a certain degree of sequence identity with the murine and human TCCR molecules herein. The murine and human prior art cytokine receptors are purported to be expressed in lymphoid tissue, including the thymus, spleen, lymph nodes and peripheral blood leukocytes—and are further indicated to be present on both B- and T-cells and have a function relating to the proliferation, differentiation and/or activation of immune cells, perhaps in the development and regulation of the immune response. However, WO97/44455 and Sprecher et al., supra identify neither the precise role of TCCR and its homologs in the mediation of T-cell differentiation and cytokine release profiles into Th1 subtype and Th2 subtype, nor the host of disorders that are implicated by the release of the cytokine T-cell subtypes.

SUMMARY OF THE INVENTION

The present invention concerns methods for the diagnosis and treatment of immune related disease in mammals, including humans—specifically the physiology (e.g., cytokine release profiles) and diseases resulting from a bias in the T-cell differentiation pathway into the Th1 subtype or the Th2 subtype. The present invention is based on the identification of the gene encoding and amino acid sequence of TCCR (previously known as NPOR), the absence or inactivation of which biases the differentiation of T-cells into the Th2 subtype in mammals. Certain immune diseases can be treated by suppressing or enhancing the differentiation of T-cells into either the Th1 or the Th2 subtype.

The present invention further concerns a method for enhancing, stimulating or potentiating the differentiation of T-cells into the Th2 subtype instead of the Th1 subtype, comprising the administration of an effective amount of a TCCR antagonist. Optionally, the method occurs in a mammal and the effective amount is a therapeutically effective amount. Optionally, the TCCR antagonist induced differentiation of T-cells into Th2 subtype cells further results in a Th2 cytokine release profile upon antigen stimulation (e.g., Il-4, Il-5 Il-10 and Il-13). Diseases which are characterized by an overproduction of Th1 cytokines, and which would be responsive to the equilibrating effect of Th2-subtype stimulation of differentiation and the resulting cytokine release profile, include autoimmune inflammatory diseases (e.g., allergic encephalomyelitis, multiple sclerosis, insulin-dependent diabetes mellitus, autoimmune uveoretinitis, inflammatory bowel disease (e.g., Crohn's disease, ulcerative colitis), autoimmune thyroid disease) and allograft rejection.

The present invention further concerns a method for preventing, inhibiting or attenuating the differentiation of T-cells into the Th2 subtype (i.e., causes differentiation into Th1 subtypes), comprising the administration of an effective amount of a TCCR or agonist. Optionally, the method occurs in a mammal and the effective amount is a therapeutically effective amount. Optionally, this TCCR or agonist induced differentiation results in a Th1 cytokine release profile upon antigen stimulation (e.g., γ-interferon). Diseases which are characterized by an overproduction of Th2 cytokines (or insufficient production of Th1 cytokines), and which would be responsive to the equilibrating effect of Th1-subtype stimulation of differentiation Th2 cytokine overproduction would be expected to be effective in treating infectious diseases (e.g., *Leishmania major, Mycobacterium leprae, Candida albicans, Toxoplasma gondi*, respiratory syncytial virus, human immunodeficiency virus) and allergic disorders (e.g., asthma, allergic rhinitis, atopic dermatitis, vernal conjunctivitis).

In one embodiment, the present invention concerns an isolated antibody which binds a TCCR polypeptide (e.g., anti-TCCR). In one aspect, the antibody mimics the activity of a TCCR polypeptide (an agonist antibody) or conversely the antibody inhibits or neutralizes the activity of a TCCR polypeptide (an antagonist antibody). In another aspect, the antibody is a monoclonal antibody, which preferably has nonhuman complementarity determining region (CDR) residues and human framework region (FR) residues. The antibody may be labeled and may be immobilized on a solid support. In a further aspect, the antibody is an antibody fragment, a single-chain antibody, or an anti-idiotypic antibody.

In another embodiment, the invention concerns the use of the polypeptides and antibodies of the invention to prepare a composition or medicament which has the uses described above.

In a further embodiment, the invention concerns nucleic acid encoding an anti-TCCR antibody, and vectors and recombinant host cells comprising such nucleic acid. In a still further embodiment, the invention concerns a method for producing such an antibody by culturing a host cell transformed with nucleic acid encoding the antibody under conditions such that the antibody is expressed, and recovering the antibody from the cell culture.

The invention further concerns antagonists of a TCCR polypeptide that inhibit one or more functions or activities of the TCCR polypeptide. Alternatively, the invention concerns TCCR agonists that stimulate or enhance one or more functions or activities of the TCCR polypeptide. Preferably such antagonists and/or agonists are TCCR variants, peptide fragments, small molecules, antisense oligonucleotides (DNA or RNA), ribozymes or antibodies (monoclonal, humanized, specific, single-chain, heteroconjugate or fragment of the aforementioned). Additionally, TCCR agonists can include potential TCCR ligands, while potential TCCR antagonists can include soluble TCCR extracellular domains (ECD).

In a further embodiment, the invention concerns isolated nucleic acid molecules that hybridize to the nucleic acid molecules encoding the TCCR polypeptides, or the complement. The nucleic acid preferably is DNA, and hybridization preferably occurs under stringent conditions. Such nucleic acid molecules can act as antisense molecules of the amplified genes identified herein, which, in turn, can find use in the modulation of the respective amplified genes, or as antisense primers in amplification reactions. Furthermore, such sequences can be used as part of ribozyme and/or triple helix sequence which, in turn, may be used in regulation of the amplified genes.

In another embodiment, the invention concerns a method for determining the presence of a TCCR polypeptide comprising exposing a cell suspected of containing the polypeptide to an anti-TCCR antibody and determining the binding of the antibody to the cell.

In yet another embodiment, the present invention concerns a method of diagnosing a Th1-mediated or Th2-mediated disorder in a mammal, comprising detecting the level of expression of a gene encoding a TCCR polypeptide (a) in a test sample of tissue cells obtained from the mammal, and (b) in a control sample of known normal tissue cells of the same cell type, wherein a lower expression level in the test sample versus the control indicates the presence of a Th2-mediated disorder and a higher expression level in the test sample versus the control indicates the presence of a Th1-mediated disorder in the mammal from which the test tissue cells were obtained.

In another embodiment, the present invention concerns a method of diagnosing an immune disease in a mammal, comprising (a) contacting an anti-TCCR antibody with a test sample of tissue cells obtained from the mammal, and (b) detecting the formation of a complex between the antibody and the TCCR polypeptide in the test sample. The detection may be qualitative or quantitative, and may be performed in comparison with monitoring the complex formation in a control sample of known normal tissue cells of the same cell type. A larger quantity of complexes formed in the test sample indicates the presence of TCCR and a Th1-mediated disorder, while a lesser quantity indicates a Th2-mediated disorder in the mammal from which the test tissue cells were obtained. The antibody preferably carries a detectable label. Complex formation can be monitored, for example, by light microscopy, flow cytometry, fluorimetry, or other techniques known in the art. The test sample is usually obtained from an individual suspected of having a deficiency or abnormality of the immune system.

In another embodiment, the present invention concerns a diagnostic kit, containing an anti-TCCR antibody and a carrier (e.g. a buffer) in suitable packaging. The kit preferably contains instructions for using the antibody to detect the TCCR polypeptide.

In a further embodiment, the invention concerns an article of manufacture, comprising:
  a container;
  a label on the container; and
  a composition comprising an active agent contained within the container; wherein the composition is effective for stimulating or inhibiting an immune response in a mammal, the label on the container indicates that the composition can be used to treat an immune related disease, and the active agent in the composition is an agent stimulating or inhibiting the expression and/or activity of the TCCR polypeptide. In a preferred aspect, the active agent is a TCCR polypeptide or an anti-TCCR antibody.

A further embodiment is a method for identifying a compound capable of modulating the expression and/or biological activity of a TCCR polypeptide by contacting a candidate compound with a TCCR polypeptide under conditions and for a time sufficient to allow these two components to interact. In a specific aspect, either the candidate compound or the TCCR polypeptide is immobilized on a solid support. In another aspect, the non-immobilized component carries a detectable label.

BRIEF DESCRIPTION OF THE DRAWINGS

FIG. 1 is a diagrammatic representation of the differentiation of the CD4+ T-cell differentiation into Th1 and Th2 cells, the primary cytokines responsible for effecting the differentiation, the primary cytokines released from the differentiation of the respective subsets upon antigen stimulation and the physiological effects mediated by the cytokine profiles released.

FIG. 2 is a diagrammatic representation of the negative feedback loop describing the interrelationship between the cytokines released by the Th1 and Th2 T-cell subtypes.

FIG. 3 shows the amino acid sequence for human TCCR (hTCCR) (SEQ ID NO:1). The sequence has also been published in WO97/44455 filed on 23 May 1996 and is further available from GenBank under accession number 4759327. This sequence is further described in Sprecher et al., *Biochem. Biophys, Res. Commun.* 246(1): 82-90 (1998). In SEQ ID NO:1, a signal peptide has been identified from amino acid residues 1 to about 32, a transmembrane domain from about amino acid residues 517 to about 538, N-glycosylation sites at about residues 51-54, 76-79, 302-305, 311-314, 374-377, 382-385, 467-470, 563-566, N-myristoylation sites at about residues 107-112, 240-245, 244-249, 281-286, 292-297, 373-378, 400-405, 459-464, 470-475, 531-536 and 533-538, a prokaryotic membrane lipoprotein lipid attachment site at about residues 522-532 and a growth factor and cytokine receptor family signature 1 at about residues 41-54. There is also a region of significant homology with the second subunit of the receptor for human granulocyte-macrophage colony-stimulating factor (GM-CSF) at residues 183-191.

FIG. 4 shows the amino acid sequence for murine TCCR (mTCCR) (SEQ ID NO:2). The sequence has also been published in WO97/44455 filed on 23 May 1996 and is further available from GenBank under accession number 7710109. This sequence is further described in Sprecher et al., *Biochem. Biophys, Res. Commun.* 246(1): 82-90 (1998). In SEQ ID NO:2, a signal peptide has been identified from amino acid residues 1 to about 24, the transmembrane domain from about amino acid residues 514 to about 532, N-glycosylation sites at about residues, 46-49, 296-299, 305-308, 360-361, 368-371 and 461-464, casein kinase II phosphorylation sites at about residues 10-13, 93-96, 130-133, 172-175, 184-187, 235-238, 271-274, 272-275, 323-326, 606-609 and 615-618, a tyrosine kinase phosphorylation site at about residues 202-209, N-myristoylation sites at about residues 43-48, 102-107, 295-300, 321-326, 330-335, 367-342, 393-398, 525-530 and 527-532, an amidation site at about residues 240-243, a prokaryotic membrane lipoprotein lipid attachment at about residues 516-526 and a growth factor and cytokine receptor family signature 1 at about residues 36-49. Region of significant homology exist with: (1) human erythropoietin at about residues 14-51 and (2) murine interleukin-5 receptor at residues 211-219.

FIG. 5 is a comparison of hTCCR (SEQ ID NO:1) and mTCCR (SEQ ID NO:2). Identical amino acids are shaded and gaps introduced for optimal alignment are indicated by dashes. The predicted signal peptidase cleavage site is indicated by an arrowhead. Potential N-glycosylation sites are indicated with an asterisk. The WSX motif, transmembrane domain and box1 motif are boxed.

FIG. 6 is a Northern blot of human TCCR indicating the expression profiles in adult and fetal tissues. In adults, hTCCR is most highly expressed in the thymus, but there is also signal in peripheral blood leukocytes (PBL's), spleen as well as weak expression in the lung. In fetal tissues, TCCR exhibits weak expression in lung and kidney. The expression profile of TCCR indicates that it may be involved in blood cell development and proliferation, especially of thymocytes.

FIGS. 7(A-B) examines the number and phenotype of T-cells in TCCR−/− mice. FIG. 7A is a contour plot of FACS analysis of CD4+/CD8+ T-cells taken from TCCR−/− mice and compared with wild type. FIG. 7B is a contour plot of FACS analysis of CD4+/CD8+/TcR+. The lack of any significant difference between the numbers of T-cells in TCCR−/− mice indicates that T-cell proliferation is not impaired.

FIGS. 8(A-B) examines the expression of TCCR on human T-cells. FIG. 8A is a FACS analysis contour plot of human TCCR and the pan T-cell surface marker CD2 on human T-cells. FIG. 8B is a FACS analysis contour plot of human TCCR and the B-cell maker CD20 on human B-cells. The left-most plot of both figures represent the appropriate fluorochrome conjugated secondary antibody. Cumulatively, FIGS. 8A and 8B indicate that TCCR is found on a subset of human T-cells and is not present in appreciable amounts on B-cells.

FIGS. 9(A-C) is a diagrammatic representation of the TCCR gene targeting methodology using homologous recombination. FIG. 9A represents the wild type allele with the TCCR exons denoted by solid blocks and the introns as intervening lines. "E" and "B" indicate cleavage sites for the endonucleases EcoRI and BamHI, respectively. FIG. 9B represents the targeting vector wherein exons 3-8 of TCCR have been replaced with the neomycin resistance gene from the plasmid vector pGK-neo. The thymidine kinase gene from herpes simplex virus has been inserted 5' to exon 1, a gene which provides resistance to selective pressure from gancyclovir. FIG. 9C is a representation of the final targeted or "knockout" allele after homologous recombination between the endogenous gene and the targeting vector has occurred.

FIGS. 10(A-C) are a Southern blot, gel electrophoresis image of PCR reaction and a Northern blot, respectively confirming transfection with the TCCR targeting vector. In FIG. 10A, genomic DNA was taken from ES cells resistant to the Neomycin/Gancyclovir drug selection and hybridized with a radiolabeled probe specific for TCCR. In the second lane from the left, the existence of both a 10 Kb and a 12 Kb fragment indicates that one of the TCCR alleles has been ablated. FIG. 10B is the reaction product of PCR amplified genomic DNA from TCCR−/− mouse tails. The PCR primers were designed so as differentiate between the wild type TCCR allele and the targeted ("knockout") allele resulting from the recombination event. Lanes 1 and 2 (counted from the left) show a band pattern indicative of TCCR wild type. Lane 3 shows a PCR band from a TCCR−/− mouse and lanes 5 and 6 are indicative of a TCCR heterozygote mouse (+/−). FIG. 10C is a Northern blot that has been hybridized with a probe specific for TCCR. Lane 1 is from a TCCR−/− mouse and lane 2 is a from a wild type mouse. The lack of any signal from the TCCR−/− mouse indicates that the there is no functional full length mRNA of TCCR being produced FIGS. 11(A-B) indicates an enhancement of allergic airway inflammation in TCCR−/− mice. FIG. 11A shows that TCCR−/− mice sensitized with Dust Mite Antigen (DMA) produce a greater Th2 response as measured by the number of lymphocytes that infiltrate the lung.

FIGS. 12(A-B) is a graphical representation of the Th1/Th2 responses in TCCR−/− mice, as measured by production of IFN-γ. In FIG. 12A, T-cells isolated from TCCR−/− mice are incubated with IL-12 which causes differentiation along the Th1 pathway. These cells were assayed for their production of IFN-γ, IL-4 and IL-5. IFN-γ is produced at significantly lower levels in the TCCR−/− mice as indicated by the lighter shaded bars in FIG. 12A. This indicates a greatly weakened Th1 response in the TCCR−/− mice. FIG. 12B is a graphical representation of T-cells that have been incubated with IL-4 which causes differentiation along the Th2 pathway. This indicates no difference in cytokine production between the TCCR−/− mice T-cells and wild type control cells.

FIG. 13 is a graphical representation of Ig levels produced in TCCR−/− mice. Levels of Ig subtypes IgG1, IgG2, IgG2b, IgG3, IgM and IgA were examined. As indicated by the lighter shadowed bars, TCCR−/− mice produced less IgG2a than wild type controls. The rest of the IgG levels did not differ significantly. IgG2a is produced by Th1 cells, and its notable absence in the TCCR−/− mice confirms the reduced Th1 response observed in other assays presented herein.

FIG. 14 is a graphical representation of IgG levels produced in TCCR−/− mice that have been previously immunized with ovalbumin. Mice were injected with 100 μg OVA ip on day 1 and 21 then bled on day 26. Levels of IgG1 and IgG2a were measured in the homozygous knockout mice compared to the wild type. As shown in the left side of the graph, IgG1 levels were equivalent in the wild type and knockout, whereas IgG2a levels were significantly lower in the TCCR−/− knockout compared to the wild type, reflecting a weakened Th1 response in TCCR−/− mice.

FIGS. 15(A-B) is a graphical representation showing which cell types within murine splenocytes express TCCR. FIG. 15A shows expression levels in CD4, CD8, CD19, NK1.1 and F4/80 cells, with highest levels in CD4 T cells and natural killer cells. FIG. 15B shows expression levels within Th0, T1 and Th2 cells, with expression being highest in Th0 cells and down-regulated upon differentiation of CD4 cells in both Th1 and Th2 cells. TCCR expression was detected by real time PCR and normalized to rpl19, a ribosomal housekeeping gene. Heid, C. A., et al., 1996, *Genome Res.*, 6:986-94.

FIGS. 16(A-D) is a graphical representation of antigen induced cytokine production and proliferation by lymph node cells from TCCR-deficient mice. Wild type and TCCR-deficient mice were immunized with KLH in complete Freund's adjuvant (CFA). Lymph nodes were harvested 9 days later and cultured in the presence of KLH as indicated and analyzed for their capacity to produce (FIG. 16A) IFN, (FIG. 16B) IL-4, (FIG. 16C) IL-5 or (FIG. 16D) to proliferate. Data are presented as the mean +/−SD values that were derived from 5 animals in each group. P<0.004 by unpaired T-test for IFN? levels between WT and KO at both KLH concentrations.

FIGS. 17(A-C) is a graphical representation of the effect on IgG subclass concentrations and sensitivity to *L. monocytogenes* infection. Serum was collected from wild type and TCCR-deficient mice, and total IgG subclass concentrations was determined by ELISA (FIG. 17A). OVA-specific IgG1 and IgG2a from OVA/CFA primed mice. Serum was collected from wild type and TCCR-deficient mice that were immunized with OVA in CFA and levels of IgG1 (1:320000 dilution) and IgG2a (1:5000 dilution) were determined by OVA-specific ELISA (FIG. 17B). Five TCCR-deficient mice or wild type littermates were infected subcutaneously with $3 \times 10^4$ CFU of *L. monocytogenes*. Three or nine days later, the livers were harvested and bacterial titers were determined (FIG. 17C). Data are presented as the mean +/−SD values that were derived from 5 animals in each group. P<0.001 by unpaired T-test between WT and KO at both time points.

FIG. 18(A-D) is a graphical representation of the in vitro induction of Th cell differentiation and proliferation. CD4+ T-cells purified from the spleens of wild type or TCCR-deficient mice were differentiated into Th1 or Th2 cells (FIG. 18A) in the presence of ConA and irradiated wild type APC or (FIG. 18B) with anti-CD3 and anti-CD28 as stimuli. Production of IFN and IL-4 was determined by ELISA. Data represent the mean value+/−SD of pools of 5 mice per group. ND, not detected. FIG. 18C represents IL-12 induced proliferation of splenocytes from wild type and TCCR-deficient mice. ConA activated splenocytes were incubated for 24 h in the presence of increasing concentrations of IL-12 as indicated. Proliferation of cells was measured by incorporation of [3H]-thymidine during the final 6 h. FIG. 18D represents IL-12R mRNA levels in unstimulated (white bars) and ConA stimulated (black bars) splenocytes. Splenic T-cells were stimulated with ConA for 72 h and mRNA levels for IL-12R 1 and IL-12R 2 were determined by real time quantitative PCR (Taqman). Fold increase are relative to the levels of RNA present in wild type unstimulated cells.

FIG. 19 shows the sequences of SEQ ID NOS:5-16 which represent the primers and probes that were used with the TAQMAN® analysis.

DETAILED DESCRIPTION OF THE PREFERRED EMBODIMENTS

I. Definitions

The term "immune related disease" means a disease in which a component of the immune system of a mammal causes, mediates or otherwise contributes to a morbidity in the mammal. Also included are diseases in which stimulation or intervention of the immune response has an ameliorative effect on progression of the disease. Included within this term are immune-mediated inflammatory diseases, non-immune-mediated inflammatory diseases, infectious diseases, immunodeficiency diseases, neoplasia, etc.

The term "Th1 mediated disorder" means a disease which is characterized by the overproduction of Th1 cytokines, including those that result from an overproduction or bias in the differentiation of T-cells into the Th1 subtype. Such diseases include, for example, autoimmune inflammatory diseases (e.g., allergic encephalomyelitis, multiple sclerosis, insulin-dependent diabetes mellitus, autoimmune uveoretinitis, thyrotoxicosis, scleroderma, systemic lupus erythematosus, rheumatoid arthritis, inflammatory bowel disease (e.g., Crohn's disease, ulcerative colitis, regional enteritis, distal ileitis, granulomatous enteritis, regional ileitis, terminal ileitis), autoimmune thyroid disease, pernicious anemia) and allograft rejection.

The term "Th2 mediated disorder" means a disease which is characterized by the overproduction of Th2 cytokines, including those that result from an overproduction or bias in the differentiation of T-cells into the Th2 subtype. Such diseases include, for example, exacerbation of infection with infectious diseases (e.g., *Leishmania major, Mycobacterium leprae, Candida albicans, Toxoplasma gondi*, respiratory syncytial virus, human immunodeficiency virus, etc.) and allergic disorders, such as anaphylactic hypersensitivity, asthma, allergic rhinitis, atopic dermatitis, vernal conjunctivitis, eczema, urticaria and food allergies, etc.

Examples of other immune, immune-related and inflammatory diseases, some of which are mediated by the effects (e.g., cytokine release profiles) of differentiation of T-cells into the Th1 and Th2 subtypes, and which can be treated according to the invention include, systemic lupus erythematosis, rheumatoid arthritis, juvenile chronic arthritis, spondyloarthropathies, systemic sclerosis (scleroderma), idiopathic inflammatory myopathies (dermatomyositis, polymyositis), Sjögren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis) autoimmune inflammatory diseases (e.g., allergic encephalomyelitis, multiple sclerosis, insulin-dependent diabetes mellitus, autoimmune uveoretinitis, thyrotoxicosis, scleroderma, systemic lupus erythematosus, rheumatoid arthritis, inflammatory bowel disease (e.g., Crohn's disease, ulcerative colitis, regional enteritis, distal ileitis, granulomatous enteritis, regional ileitis, terminal ileitis), autoimmune thyroid disease, pernicious anemia) and allograft rejection, diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barré syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory bowel disease (ulcerative colitis, Crohn's disease), gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, transplantation associated diseases including graft rejection and graft-versus-host-disease. Infectious diseases including viral diseases such as AIDS (HIV infection), hepatitis A, B, C, D, and E, herpes, etc., bacterial infections, fungal infections, protozoal infections, parasitic infections, and respiratory syncytial virus, human immunodeficiency virus, etc.) and allergic disorders, such as anaphylactic hypersensitivity, asthma, allergic rhinitis, atopic dermatitis, vernal conjunctivitis, eczema, urticaria and food allergies, etc.

"Treatment" is an intervention performed with the intention of preventing the development or altering the pathology of a disorder. Accordingly, "treatment" refers to both therapeutic treatment and prophylactic or preventative measures, wherein the object is to prevent, slow down (lessen) or ameliorate the targeted pathological condition or disorder. Those in need of treatment include those already with the disorder as well as those in which the disorder is to be prevented. In treatment of an immune related disease (e.g., Th1-mediated and Th2-mediated disorder), a therapeutic agent may directly decrease or increase the magnitude of response of a pathological component of the disorder, or render the disease more susceptible to treatment by other therapeutic agents, e.g. antibiotics, antifungals, anti-inflammatory agents, chemotherapeutics, etc.

The term "effective amount" is the minimum concentration of TCCR polypeptide, agonist thereof and/or antagonist thereof which causes, induces or results in either a detectable bias in the differentiation of T-cells into either the Th1 subtype or the Th2 subtype and/or the cytokine release profile which these T-cell subtypes secrete. Furthermore a "therapeutically effective amount" is the minimum concentration (amount) of TCCR polypeptides, agonists thereof and/or antagonist thereof which would be effective in treating either Th1-mediated or Th2-mediated disorders.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

The "pathology" of an immune related disease includes all phenomena that compromise the well-being of the patient. This includes, without limitation, abnormal or uncontrollable cell growth, antibody production, auto-antibody production, complement production and activation, interference with the normal functioning of neighboring cells, release of cytokines or other secretory products at abnormal levels, suppression or aggravation of any inflammatory or immunological response, infiltration of inflammatory cells (neutrophilic, eosinophilic, monocytic, lymphocytic) into tissue spaces, etc.

"Mammal" for purposes of treatment refers to any animal classified as a mammal, including humans, domestic and farm animals, and zoo, sports, or pet animals, such as dogs, horses, cats, cattle, sheeps, pigs, goats, rabbit, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The term "cytotoxic agent" as used herein refers to a substance that inhibits or prevents the function of cells and/or causes destruction of cells. The term is intended to include radioactive isotopes (e.g. $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "growth inhibitory agent" when used herein refers to a compound or composition which inhibits growth of a cell, especially cancer cell overexpressing any of the genes identified herein, either in vitro or in vivo. Thus, the growth inhibitory agent is one which significantly reduces the percentage of cells overexpressing such genes in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxol, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogens, and antineoplastic drugs" by Murakami et al. (WB Saunders: Philadelphia, 1995), especially p. 13.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ, colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

The terms "TCCR polypeptide", "TCCR protein" and "TCCR" when used herein encompass native sequence TCCR and TCCR polypeptide variants (which are further defined herein). The TCCR polypeptide may be isolated from a variety of sources, such as from human tissue types or from another source, or prepared by recombinant and/or synthetic methods.

A "native sequence TCCR" comprises a polypeptide having the same amino acid sequence as a TCCR polypeptide derived from nature. Such native sequence TCCR can be isolated from nature or can be produced by recombinant and/or synthetic means. The term "native sequence TCCR" specifically encompasses naturally-occurring truncated or secreted forms (e.g., an extracellular domain sequence), naturally-occurring truncated forms (e.g., alternatively spliced forms) and naturally-occurring allelic variants of the TCCR. In one embodiment of the invention, the native sequence human TCCR is a mature or full-length native sequence TCCR comprising amino acids 1 to 636 of FIG. 3 (SEQ ID NO: 1). Similarly, the native sequence murine TCCR is a mature or full-length native sequence TCCR comprising amino acid 1 to 623 of FIG. 4 (SEQ ID NO:2). Also, while the TCCR polypeptides disclosed in FIG. 3 (SEQ ID NO:1) and FIG. 4 (SEQ ID NO:2) is shown to begin with the methionine residue designated herein as amino acid position 1, it is conceivable and possible that another methionine residue located either upstream or downstream from amino acid position 1 in FIG. 3 (SEQ ID NO:1) or FIG. 4 (SEQ ID NO:2) may be employed as the starting amino acid residue for the TCCR polypeptide.

The "TCCR polypeptide extracellular domain" or "TCCR ECD" refers to a form of the TCCR polypeptide which is essentially free of the transmembrane and cytoplasmic domains. Ordinarily, a TCCR polypeptide ECD will have less than about 1% of such transmembrane and/or cytoplasmic domains and preferably, will have less than about 0.5% of such domains. It will be understood that any transmembrane domain(s) identified for the TCCR polypeptides of the present invention are identified pursuant to criteria routinely employed in the art for identifying that type of hydrophobic domain. The exact boundaries of a transmembrane domain may vary but most likely be no more than about 5 amino acids at either end of the domain as initially identified. As such, in one embodiment of the present invention, the extracellular domain of a human TCCR polypeptide comprises amino acids 1 or about 33 to $X_1$ wherein $X_1$ is any amino acid residue from residue 512 to residue 522 of FIG. 3 (SEQ ID NO:1). Similarly, the extracellular domain of the murine TCCR polypeptide comprises amino acids 1 or about 25 to $X_2$ wherein $X_2$ is any amino acid residues from residue 509 to residue 519 of FIG. 4 (SEQ ID NO:2).

"TCCR variant polypeptide" means an active TCCR polypeptide as defined below having at least about 80% amino acid sequence identity with the amino acid sequence of: ($a_1$) residue 1 or about 33 to 636 of the human TCCR polypeptide shown in FIG. 3 (SEQ ID NO:1); (a$_2$) residue 1 or about 25 to 623 of the murine TCCR polypeptide shown in FIG. 4 (SEQ ID NO:2); (b$_1$) X$_3$ to 636 of the human TCCR polypeptide shown in FIG. 3 (SEQ ID NO:1), wherein X$_3$ is any amino acid residue 27 to 37 of FIG. 3 (SEQ ID NO:1); (b$_2$) X$_4$ to 623 of the murine TCCR polypeptide shown in FIG. 4 (SEQ ID NO:2), wherein X$_4$ is any amino acid residue from 20 to 30 of FIG. 4 (SEQ ID NO:2); (c$_1$) 1 or about 33 to X$_1$, wherein X$_1$ is any amino acid residue from residue 512 to residue 522 and of FIG. 3 (SEQ ID NO:1); (c$_2$) 1 or about 25 to X$_2$, wherein X$_2$ is any amino acid residue from residue 509 to 519 of FIG. 4 (SEQ ID NO:2); (d$_1$) X$_5$ to 636, wherein X$_5$ is any amino acid from residue 533 to 543 of FIG. 3 (SEQ ID NO:1); (d$_2$) X$_6$ to 623, wherein X$_6$ is any amino acid from residue 527 to 537 of FIG. 4 (SEQ ID NO:2) or (e) another specifically derived fragment of the amino acid sequences shown in FIG. 3 (SEQ ID NO:1) and in FIG. 4 (SEQ ID NO:2).

Such TCCR variant polypeptides include, for instance, TCCR polypeptides wherein one or more amino acid residues are added, or deleted, at the N- and/or C-terminus, as well as within one or more internal domains, of the sequence of FIG. 3 (SEQ ID NO:1) and FIG. 4 (SEQ ID NO:2). Ordinarily, a TCCR variant polypeptide will have at least about 80% amino acid sequence identity, more preferably at least about 81% amino acids sequence identity, more preferably at least about 82% amino acid sequence identity, more preferably at least about 83% amino acid sequence identity, more preferably at least about 84% amino acid sequence identity, more preferably at least about 85% amino acid sequence identity, more preferably at least about 86% amino acid sequence identity, more preferably at least about 87% amino acid sequence identity, more preferably at least about 88% amino acid sequence identity, more preferably at least about 89% amino acid sequence identity, more preferably at least about 90% amino acid sequence identity, more preferably at least about 91% amino acid sequence identity, more preferably at least about 92% amino acid sequence identity, more preferably at least about 93% amino acid sequence identity, more preferably at least about 94% amino acid sequence identity, more preferably at least about 95% amino acid sequence identity, more preferably at least about 96% amino acid sequence identity, more preferably at least about 97% amino acid sequence identity, more preferably at least about 98% amino acid sequence identity, more preferably at least about 99% amino acid sequence identity with: (a$_1$) residue 1 or about 33 to 636 of the human TCCR polypeptide shown in FIG. 3 (SEQ ID NO:1); (a$_2$) residue 1 or about 25 to 623 of the murine TCCR polypeptide shown in FIG. 4 (SEQ ID NO:2); (b$_1$) X$_3$ to 636 of the human TCCR polypeptide shown in FIG. 3 (SEQ ID NO:1), wherein X$_3$ is any amino acid residue 27 to 37 of FIG. 3 (SEQ ID NO:1); (b$_2$) X$_4$ to 623 of the murine TCCR polypeptide shown in FIG. 4 (SEQ ID NO:2), wherein X$_4$ is any amino acid residue from 20 to 30 of FIG. 4 (SEQ ID NO:2); (c$_1$) 1 or about 33 to X$_1$ wherein X$_1$ is any amino acid residue from residue 512 to residue 522 and of FIG. 3 (SEQ ID NO:1); (c$_2$) 1 or about 25 to X$_2$, wherein X$_2$ is any amino acid residue from residue 509 to 519 of FIG. 4 (SEQ ID NO:2); (d$_1$) X$_5$ to 636, wherein X$_5$ is any amino acid from residue 533 to 543 of FIG. 3 (SEQ ID NO:1); (d$_2$) X$_6$ to 623, wherein X$_6$ is any amino acid from residue 527 to 537 of FIG. 4 (SEQ ID NO:2) or (e) another specifically derived fragment of the amino acid sequences shown in FIG. 3 (SEQ ID NO:1) and in FIG. 4 (SEQ ID NO:2).

TCCR variant polypeptides are at least about 10 amino acids in length, often at least about 20 amino acids in length, more often at least about 30 amino acids in length, more often at least about 40 amino acids in length, more often at least about 50 amino acids in length, more often at least about 60 amino acids in length, more often at least about 70 amino acids in length, more often at least about 80 amino acids in length, more often at least about 90 amino acids in length, more often at least about 100 amino acids in length, more often at least about 150 amino acids in length, more often at least about 200 amino acids in length, more often at least about 250 amino acids in length, more often at least about 300 amino acids in length, more often at least about 400 amino acids in length, more often at least about 500 amino acids in length, more often at least about 600 amino acids in length, or more.

"Percent (%) amino acid sequence identity" with respect to the polypeptide sequences identified herein is defined as the percentage of amino acid residues in a candidate sequence that are identical with the amino acid residues in a sequence of the TCCR polypeptides, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are obtained as described below by using the sequence comparison computer program ALIGN-2, wherein the complete source code for the ALIGN-2 program is provided in Table 3(A-Q). The ALIGN-2 sequence comparison computer program was authored by Genentech, Inc. and the source code shown in Table 3(A-Q) has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 3(A-Q). The ALIGN-2 program should be compiled for use on a UNIX operating system, preferably digital UNIX V4.0D. All sequence comparison parameters are set by the ALIGN-2 program and do not vary.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations, Table 2(A-B) demonstrate how to calculate the % amino acid sequence identity of the amino acid sequence designated "Comparison Protein" to the amino acid sequence designated "PRO".

Unless specifically stated otherwise, all % amino acid sequence identity values used herein are obtained as described above using the ALIGN-2 sequence comparison computer program. However, % amino acid sequence identity may also be determined using the sequence comparison program NCBI-BLAST2 (Altschul et al., *Nucleic Acids Res.* 25:3389-3402 (1997)). The NCBI-BLAST2 sequence comparison program may be downloaded from the NCBI website or otherwise obtained from the National Institutes of Health, Bethesda, Md., USA 20892. NCBI-BLAST2 uses several search parameters, wherein all of those search parameters are set to default values including, for example, unmask=yes, stand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

Also included within the term "polypeptides of the invention" are polypeptides which in the context of the amino acid sequence identity comparisons performed as described above, include amino acid residues in the sequences compared that are not only identical, but also those that have similar properties. These polypeptides are termed "positives". Amino acid residues that score a positive value to an amino acid residue of interest are those that are either identical to the amino acid residue of interest or are a preferred substitution (as defined in Table I below) of the amino acid residue of interest. For purposes herein, the % value of positives of a given amino acid sequence A to, with, or against a given amino acid sequence B (which can alternatively be phrased as a given amino acid sequence A that has or comprises a certain % positives to, with, or against a given amino acid sequence B) is calculated as follows:

100 times the fraction X/Y where X is the number of amino acid residues scoring a positive value as defined above by the sequence alignment program ALIGN-2 in that program's alignment of A and B, and where Y is the total number of amino acid residues in B. It will be appreciated that where the length of amino acid sequence A is not equal to the length of amino acid sequence B, the % positives of A to B will not equal the % positives of B to A.

"TCCR variant polynucleotide" or "TCCR variant nucleic acid sequence" means a nucleic acid molecule which encodes an active TCCR polypeptide as defined below and which has at least about 80% nucleic acid sequence identity with a nucleic acid sequence which encodes: ($a_1$) amino acid residues 1 or about 33 to 636 of the human TCCR polypeptide shown in FIG. 3 (SEQ ID NO: 1); ($a_2$) amino acid residues 1 or about 25 to 623 of the murine TCCR polypeptide shown in FIG. 4 (SEQ ID NO:2); ($b_1$) amino acids $X_3$ to 636 of the TCCR polypeptide shown in FIG. 3 (SEQ ID NO: 1), wherein $X_3$ is any amino acid residue from 27 to 37 of FIG. 3 (SEQ ID NO:1); ($b_2$) amino acids $X_4$ to 623 of the TCCR polypeptide shown in FIG. 4 (SEQ ID NO:2), wherein $X_4$ is any amino acid residue from 20 to 30 of FIG. 4 (SEQ ID NO:2); ($c_1$) amino acids 1 or about 33 to $X_1$ wherein $X_1$ is any amino acid residue from residue 512 to residue 522 and of FIG. 3 (SEQ ID NO:1); ($c_2$) amino acids 1 or about 25 to $X_2$, wherein $X_2$ is any amino acid residue from residue 509 to 519 of FIG. 4 (SEQ ID NO:2); ($d_1$) amino acids $X_5$ to 636, wherein $X_5$ is any amino acid from residue 533 to 543 of FIG. 3 (SEQ ID NO:1); ($d_2$) amino acids $X_6$ to 623, wherein $X_6$ is any amino acid from residue 527 to 537 of FIG. 4 (SEQ ID NO:2); or (e) a nucleic acid sequence which encodes another specifically derived fragment of the amino acid sequence shown in FIG. 3 (SEQ ID NO:1) or FIG. 4 (SEQ ID NO:2). Ordinarily, a TCCR variant polynucleotide will have at least about 80% nucleic acid sequence identity, more preferably at least about 81% nucleic acid sequence identity, more preferably at least about 82% nucleic acid sequence identity, more preferably at least about 83% nucleic acid sequence identity, more preferably at least about 84% nucleic acid sequence identity, more preferably at least about 85% nucleic acid sequence identity, more preferably at least about 86% nucleic acid sequence identity, more preferably at least about 87% nucleic acid sequence identity, more preferably at least about 88% nucleic acid sequence identity, more preferably at least about 89% nucleic acid sequence identity, more preferably at least about 90% nucleic acid sequence identity, more preferably at least about 91% nucleic acid sequence identity, more preferably at least about 92% nucleic acid sequence identity, more preferably at least about 93% nucleic acid sequence identity, more preferably at least about 94% nucleic acid sequence identity, more preferably at least about 95% nucleic acid sequence identity, more preferably at least about 96% nucleic acid sequence identity, more preferably at least about 97% nucleic acid sequence identity, more preferably at least about 98% nucleic acid sequence identity and yet more preferably at least about 99% nucleic acid sequence identity with a nucleic acid sequence encoding amino acid residues: ($a_1$) 1 or about 33 to 636 of the human TCCR polypeptide shown in FIG. 3 (SEQ ID NO:1); ($a_2$) 1 or about 25 to 623 of the murine TCCR polypeptide shown in FIG. 4 (SEQ ID NO:2); ($b_1$) $X_3$ to 636 of the human TCCR polypeptide shown in FIG. 3 (SEQ ID NO:1), wherein $X_3$ is any amino acid residue 27 to 37 of FIG. 3 (SEQ ID NO:1); ($b_2$) $X_4$ to 623 of the murine TCCR polypeptide shown in FIG. 4 (SEQ ID NO:2), wherein $X_4$ is any amino acid residue from 20 to 30 of FIG. 4 (SEQ ID NO:2); ($c_1$) 1 or about 33 to $X_1$, wherein $X_1$ is any amino acid residue from residue 512 to residue 522 and of FIG. 3 (SEQ ID NO:1); ($c_2$) 1 or about 25 to $X_2$, wherein $X_2$ is any amino acid residue from residue 509 to 519 of FIG. 4 (SEQ ID NO:2); ($d_1$) $X_5$ to 636, wherein $X_5$ is any amino acid from residue 533 to 543 of FIG. 3 (SEQ ID NO:1); ($d_2$) $X_6$ to 623, wherein $X_6$ is any amino acid from residue 527 to 537 of FIG. 4 (SEQ ID NO:2) or (e) another specifically derived fragment of the amino acid sequences shown in FIG. 3 (SEQ ID NO:1) and in FIG. 4 (SEQ ID NO:2).

Ordinarily, TCCR variant polynucleotides are at least about 30 nucleotides in length, often at least about 60 nucleotides in length, more often at least about 90 nucleotides in length, more often at least about 120 nucleotides in length, more often at least about 150 nucleotides in length, more often at least about 180 nucleotides in length, more often at least about 210 nucleotides in length, more often at least about 240 nucleotides in length, more often at least about 270 nucleotides in length, more often at least about 300 nucleotides in length, more often at least about 450 nucleotides in length, more often at least about 600 nucleotides in length, more often at least about 900 nucleotides in length, or more.

"Percent (%) nucleic acid sequence identity" with respect to the TCCR polypeptide-encoding nucleic acid sequences identified herein is defined as the percentage of nucleotides in a candidate sequence that are identical with the nucleotides in an invention polypeptide-encoding sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % nucleic acid sequence identity values are obtained as described below by using the sequence comparison computer program ALIGN-2, wherein the complete source code for the ALIGN-2 program is provided in Table 3(A-Q). The ALIGN-2 sequence comparison computer program was authored by Genentech, Inc. and the source code shown in Table 3(A-Q) has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 3(A-Q). The ALIGN-2 program should be compiled for use on a UNIX operating system, preferably digital UNIX V4.0D. All sequence comparison parameters are set by the ALIGN-2 program and do not vary.

For purposes herein, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Table 2(C-D) demonstrates how to calculate the % nucleic acid sequence identity of the nucleic acid sequence designated "Comparison DNA" to the nucleic acid sequence designated "PRO-DNA".

Unless specifically stated otherwise, all % nucleic acid sequence identity values used herein are obtained as described above using the ALIGN-2 sequence comparison computer program. However, % nucleic acid sequence identity may also be determined using the sequence comparison program NCBI-BLAST2 (Altschul et al., *Nucleic Acids Res.* 25:3389-3402 (1997)). The NCBI-BLAST2 sequence comparison program may be downloaded from the NCBI website or otherwise obtained from the National Institutes of Health, Bethesda, Md. USA 20892. NCBI-BLAST2 uses several search parameters, wherein all of those search parameters are set to default values including, for example, unmask=yes, strand=all, expected occurrences=10, minimum low complexity length=155, multi-pass e-value=0.01, constant for multi-pass=25, dropoff for final gapped alignment=25 and scoring matrix=BLOSUM62.

In situations where NCBI-BLAST2 is employed for sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program NCBI-BLAST2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

In other embodiments, TCCR variant polynucleotides are nucleic acid molecules that encode an active polypeptide of the invention and which are capable of hybridizing, preferably under stringent hybridization and wash conditions, to nucleotide sequences encoding the full-length invention polypeptide. Invention variant polypeptides include those that are encoded by an invention variant polynucleotide.

The term "positives", in the context of the amino acid sequence identity comparisons performed as described above, includes amino acid residues in the sequences compared that are not only identical, but also those that have similar properties. Amino acid residues that score a positive value to an amino acid residue of interest are those that are either identical to the amino acid residues of interest or are a preferred substitution (as defined in Table I below) of the amino acid residue of interest.

For purposes herein, the % value of positives of a given amino acid sequence A to, with, or against a given amino acid sequence B (which can alternatively be phrased as a given amino acid sequence A that has or comprises a certain % positives to, with, or against a given amino acid sequence B) is calculated as follows:

100 times the fraction X/Y where X is the number of amino acid residues scoring a positive value as defined above by the sequence alignment program ALIGN-2 in that program's alignment of A and B, and where Y is the total number of amino acids residues in B. It will be appreciated that where the length of amino acid sequence A is not equal to the length of amino acid sequence B, the % positives of A to B will not equal the % positives of B to A.

"Isolated," when used to describe the various polypeptides disclosed herein, means polypeptide that has been identified and separated and/or recovered from a component of its natural environment. Preferably, the isolated polypeptide is free of association with all components with which it is naturally associated. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the TCCR natural environment will not be present. Ordinarily, however, isolated polypeptide will be prepared by at least one purification step.

An "isolated" nucleic acid molecule encoding a TCCR polypeptide is a nucleic acid molecule that is identified and separated from at least one contaminant nucleic acid molecule with which it is ordinarily associated in the natural source of the TCCR-encoding nucleic acid. Preferably, the isolated nucleic acid is free of association with all components with which it is naturally associated. An isolated TCCR-encoding nucleic acid molecule is other than in the form or setting in which it is found in nature. Isolated nucleic acid molecules therefore are distinguished from the TCCR-encoding nucleic acid molecule as it exists in natural cells. However, an isolated nucleic acid molecule encoding a TCCR polypeptide includes TCCR-encoding nucleic acid molecules contained in cells that ordinarily express TCCR where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize, for example, promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in the same reading frame. However, enhancers do not have to be contiguous. Linking is accomplished by ligation at convenient restriction sites. If such sites do not exist, synthetic oligonucleotide adaptors or linkers are used in accordance with conventional practice.

The term "antibody" is used in the broadest sense and specifically covers, for example, single anti-TCCR monoclonal antibodies (including agonist, antagonist, and neutralizing antibodies), anti-TCCR antibody compositions with polyepitopic specificity, single chain anti-TCCR antibodies, and fragments of anti-TCCR antibodies (see below). The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 ug/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. In one embodiment, moderately stringent conditions involve overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising a polypeptide of the invention fused to a "tag polypeptide". The tag polypeptide has enough residues to provide an epitope against which an antibody can be made, yet is short enough such that it does not interfere with the activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

"Active" or "activity" for purposes herein refers to form(s) of proteins of the invention which retain the biologic and/or immunologic activities of a native or naturally-occurring TCCR polypeptide, wherein "biological" activity refers to a biological function (either inhibitory or stimulatory) caused by a native or naturally-occurring TCCR other than the ability to serve as an antigen in the production of an antibody against an antigenic epitope possessed by a native or naturally-occurring polypeptide of the invention. Similarly, an "immunological" activity refers to the ability to serve as an antigen in the production of an antibody against an antigenic epitope possessed by a native or naturally-occurring polypeptide of the invention.

"Biological activity" in the context of an antibody or another molecule that can be identified by the screening assays disclosed herein (e.g. an organic or inorganic small molecule, peptide, etc.) is used to refer to the ability of such molecules to induce or inhibit infiltration of inflammatory cells into a tissue, to stimulate or inhibit T-cell proliferation or activation and to stimulate or inhibit cytokine release by cells. Another preferred activity is increased vascular permeability or the inhibition thereof. The most preferred activity is the modulation of the Th1/Th2 response (e.g., a decreased Th1 and/or elevated Th2 response, a decreased Th2 and/or elevated Th1 response).

The term "modulation" or "modulating" means the upregulation, downregulation or alteration of the physiology effected by the differentiation of T-cells into the Th1 and Th2 subsets (e.g., cytokine release profiles). Cellular processes within the intended scope of the term may include, but are not limited to: transcription of specific genes; normal cellular functions, such as metabolism, proliferation, differentiations, adhesion, signal transduction, apoptosis and survival, and abnormal cellular processes such as transformation, blocking of differentiation and metastasis.

The term "antagonist" is used in the broadest sense, and includes any molecule that partially or fully blocks, inhibits, or neutralizes a biological activity of a native sequence TCCR polypeptide of the invention disclosed herein (e.g., downregulation of a Th1/Th2 cellular function). In a similar manner, the term "agonist" is used in the broadest sense and includes any molecule that mimics, enhances or stimulates a biological activity of a native sequence TCCR polypeptide of the invention disclosed herein. Suitable agonist or antagonist molecules specifically include agonist or antagonist antibodies or antibody fragments, fragments or amino acid sequence variants of native polypeptides of the invention, peptides, small organic molecules, etc. Methods for identifying agonists or antagonists of a TCCR polypeptide may comprise contacting a TCCR polypeptide with a candidate agonist or antagonist molecule and measuring a detectable change in one or more biological activities normally associated with the TCCR polypeptide (e.g., upregulation/downregulation of a Th1/Th2 cellular function or effect).

A "small molecule" is defined herein to have a molecular weight below about 500 daltons, and is generally an organic compound.

"Antibodies" (Abs) and "immunoglobulins" (Igs) are glycoproteins having the same general structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas. The term "antibody" is used in the broadest sense and specifically covers, for example, single anti-TCCR monoclonal antibodies (including agonist, antagonist, and neutralizing antibodies), anti-TCCR antibody compositions with polyepitopic specificity, single chain anti-TCCR antibodies, and fragments of anti-TCCR antibodies (see below). The term "monoclonal antibody" as used herein refers to an antibody obtained from a population of substantially homogeneous antibodies, i.e., the individual antibodies comprising the population are identical except for possible naturally-occurring mutations that may be present in minor amounts. The antibody may bind to any domain of the polypeptide of the invention which may be contacted by the antibody. For example, the antibody may bind to any extracellular domain of the polypeptide and when the entire polypeptide is secreted, to any domain on the polypeptide which is available to the antibody for binding.

"Native antibodies" and "native immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three or four segments called "complementarity-determining regions" (CDRs) or "hypervariable regions" in both the light-chain and the heavy-chain variable domains. There are at least two (2) techniques for determining CDRs: (1) an approach based on cross-species sequence variability (i.e., Kabat et al., *Sequences of Proteins of immunological Interest* (National Institute of Health, Bethesda, Md. 1987); and (2) an approach based on crystallographic studies of antigen-antibody complexes (Chothia, C. et al., *Nature* 342: 877 (1989)). However, to the extent that the two techniques describe different residues they can be combined to define a hybrid CDR.

The more highly conserved portions of variable domains are called the framework (FR). The variable domains of native heavy and light chains each comprise four or five FR regions, largely adopting a β-sheet configuration, connected by the CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al., NIH Publ. No. 91-3242, Vol. I, pages 647-669 (1991)). The constant domains are not involved directly in binding an antibody to an antigen, but exhibit various effector functions, such as participation of the antibody in antibody-dependent cellular toxicity.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al., *Protein Eng.* 8(10):1057-1062 [1995]); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of immunoglobulins are called α, δ, ε, γ, and μ, respectively. The subunit structures and three-dimensional configurations of different classes of immunoglobulins are well known.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256:495 [1975], or may be made by recombinant DNA methods (see, e.g., U.S. Pat. No. 4,816,567). The "monoclonal antibodies" may also be isolated from phage antibody libraries using the techniques described in Clackson et al., Nature 352:624-628 (1991) and Marks et al., J. Mol. Biol. 222:581-597 (1991), for example. See also U.S. Pat. Nos. 5,750,373, 5,571,698, 5,403,484 and 5,223,409 which describe the preparation of antibodies using phagemid and phage vectors.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81:6851-6855 [1984]).

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementarity-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues, especially when those particular FR residues impact upon the conformation of the binding site and/or the antibody in three dimensional space. Furthermore, humanized antibodies may comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321:522-525 (1986); Reichmann et al., Nature, 332: 323-329 [1988]; and Presta, Curr. Op. Struct. Biol., 2:593-596 (1992). Optionally, the humanized antibody may also include a "primatized" antibody where the antigen-binding region of the antibody is derived from an antibody produced by immunizing macaque monkeys with the antigen of interest. Antibodies containing residues from Old World monkeys are described, for example, in U.S. Pat. Nos. 5,658,570; 5,693,780; 5,681,722; 5,750,105; and 5,756,096.

Antibodies and fragments thereof in this invention also include "affinity matured" antibodies in which an antibody is altered to change the amino acid sequence of one or more of the CDR regions and/or the framework regions to alter the affinity of the antibody or fragment thereof for the antigen to which it binds. Affinity maturation may result in an increase or in a decrease in the affinity of the matured antibody for the antigen relative to the starting antibody. Typically, the starting antibody will be a humanized, human, chimeric or murine antibody and the affinity matured antibody will have a higher affinity than the starting antibody. During the maturation process, one or more of the amino acid residues in the CDRs or in the framework regions are changed to a different residue using any standard method. Suitable methods include point mutations using well known cassette mutagenesis methods (Wells et al., 1985, Gene 34:315) or oligonucleotide mediated mutagenesis methods (Zoller et al., 1987, Nucleic Acids Res., 10:6487-6504). Affinity maturation may also be performed using known selection methods in which many mutations are produced and mutants having the desired affinity are selected from a pool or library of mutants based on improved affinity for the antigen or ligand. Known phage display techniques can be conveniently used in this approach. See, for example, U.S. Pat. No. 5,750,373; U.S. Pat. No. 5,223,409, etc.

Human antibodies are also with in the scope of the antibodies of the invention. Human antibodies can be produced using various techniques known in the art, including phage display libraries [Hoogenboom and Winter, *J. Mol. Biol.* 227: 381 (1991); Marks et al., *J. Mol. Biol.*, 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985); Boerner et al., *J. Immunol,* 147(1):86-95 (1991); U.S. Pat. No. 5,750,373]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625, 126; 5,633,425; 5,661,016, and in the following scientific publications: Marks et al., *Bio/Technology* 10: 779-783 (1992); Lonberg et al., *Nature* 368:856-859 (1994); Morrison, *Nature* 368:812-13 (1994); Fishwild et al., *Nature Biotechnology* 14: 845-51 (1996); Neuberger, *Nature Biotechnology* 14: 826 (1996); Lonberg and Huszar, *Intern. Rev. Immunol.* 13: 65-93 (1995).

"Single-chain Fv" or "sFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the sFv to form the desired structure for antigen binding. For a review of sFv see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA* 90:6444-6448 (1993).

The term "isolated" when it refers to the various polypeptides of the invention means a polypeptide which has been identified and separated and/or recovered from a component of its natural environment. Contaminant components of its natural environment are materials which would interfere with diagnostic or therapeutic uses for the antibody, and may include enzymes, hormones, and other proteinaceous or non-proteinaceous solutes. In preferred embodiments, the polypeptide of the invention will be purified (1) to greater than 95% by weight of the compound as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated compound, e.g. antibody or polypeptide, includes the compound in situ within recombinant cells since at least one component of the compound's natural environment will not be present. Ordinarily, however, isolated compound will be prepared by at least one purification step.

The word "label" when used herein refers to a detectable compound or composition which is conjugated directly or indirectly to the compound, e.g. antibody or polypeptide, so as to generate a "labelled" compound. The label may be detectable by itself (e.g. radioisotope labels or fluorescent labels) or, in the case of an enzymatic label, may catalyze chemical alteration of a substrate compound or composition which is detectable.

By "solid phase" is meant a non-aqueous matrix to which the compound of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as the anti-ErbB2 antibodies disclosed herein and, optionally, a chemotherapeutic agent) to a mammal. The components of the liposome are commonly arranged in a bilayer formation, similar to the lipid arrangement of biological membranes.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG4 subtypes, IgA (including IgA-1 and IgA-2), IgE, IgD or IgM.

II. Compositions and Methods of the Invention

A. Full-length TCCR Polypeptide

The present invention provides in part a novel method for using TCCR polypeptides to treat immune-related disorders, including the modulation of the differentiation of T-cells into the Th1 and Th2 subtypes and to the treatment of the host of disorders implicated thereby. In particular, cDNAs encoding TCCR polypeptides have been identified, isolated and their use in the treatment of Th1-mediated and Th2-mediated disorders is disclosed in further detail below. It is noted that TCCR defines both the native sequence molecules and variants as provided in the definition section, while the term hTCCR and mTCCR define the singular native sequence polypeptides shown in FIGS. 3 (SEQ ID NO:1) and 4 (SEQ ID NO:2), respectively. However, for the sake of simplicity, in the present specification the protein encoded by DNA41419 (hTCCR) and/or DNA120632 (mTCCR) as well as all further native homologues and variants included in the foregoing definition of TCCR will be referred to as "TCCR", regardless of their origin or mode of preparation.

The predicted amino acid sequence of the proteins encoded by DNA41419 (hTCCR, SEQ ID NO:1) and DNA120632 (mTCCR, SEQ ID NO:2) can be determined from the nucleotide sequence using routine skill. For the TCCR polypeptide and encoding nucleic acid described herein, Applicants have identified what is believed to the reading frame best identifiable with the sequence information available at the time.

Using the ALIGN-2 sequence alignment computer program referenced above, it has been found that the full-length native sequence hTCCR (FIG. 3, SEQ ID NO:1) and mTCCR (FIG. 4, SEQ ID NO:2) sequence have a certain degree of sequence identity with the Dayhoff (GenBank) sequences having accession numbers 475327 and 7710109.

B. TCCR Variants

In addition to the full-length native sequence TCCR polypeptides described herein, it is contemplated that TCCR variants can be prepared. TCCR variants can be prepared by introducing appropriate nucleotide changes into the TCCR DNA, and/or by synthesis of the desired TCCR polypeptide. Those skilled in the art will appreciate that amino acid changes may alter post-translational processes of the TCCR, such as changing the number or position of glycosylation sites or altering the membrane anchoring characteristics.

Variations in the native full-length sequence TCCR or in various domains of the polypeptide of the TCCR described herein, can be made, for example, using any of the techniques and guidelines for conservative and non-conservative mutations set forth, for instance, in U.S. Pat. No. 5,364,934. Variations may be a substitution, deletion or insertion of one or more codons encoding the TCCR that results in a change in the amino acid sequence of the TCCR as compared with the native sequence TCCR. Optionally the variation is by substitution of at least one amino acid with any other amino acid in one or more of the domains of the TCCR. Guidance in determining which amino acid residue may be inserted, substituted or deleted without adversely affecting the desired activity may be found by comparing the sequence of the TCCR with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

TCCR polypeptide fragments of the polypeptides of the invention are also within the scope of the invention. Such fragments may be truncated at the N-terminus or C-terminus, or may lack internal residues, for example, when compared with a full length native protein. Certain fragments lack amino acid residues that are not essential for a desired biological activity of the TCCR polypeptide.

TCCR fragments may be prepared by any of a number of conventional techniques. Desired peptide fragments may be chemically synthesized. An alternative approach involves generating TCCR fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, polypeptide fragments share at least one biological and/or immunological activity with the TCCR polypeptides shown in FIG. 3 (SEQ ID NO:1) and FIG. 4 (SEQ ID NO:2).

In particular embodiments, conservative substitutions of interest are shown in Table I under the heading of preferred substitutions. If such substitutions result in a change in biological activity, then more substantial changes, denominated exemplary substitutions in Table I, or as further described below in reference to amino acid classes, are introduced and the products screened.

TABLE I

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the invention polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;

(2) neutral hydrophilic: cys, ser, thr;

(3) acidic: asp, glu;

(4) basic: asn, gin, his, lys, arg;

(5) residues that influence chain orientation: gly, pro; and (6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene*, 34:315 (1985)], restriction selection mutagenesis [Wells et al., *Philos. Trans. R. Soc. London SerA,* 317:415 (1986)] or other known techniques can be performed on the cloned DNA to produce the variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science,* 244: 1081-1085 (1989)]. Alanine is also typically preferred because it is the most common amino acid. Further, it is frequently found in both buried and exposed positions [Creighton, *The Proteins,* (W.H. Freeman & Co., N.Y.); Chothia, *J. Mol. Biol.,* 150:1 (1976)]. If alanine substitution does not yield adequate amounts of variant, an isosteric amino acid can be used.

C. Modifications of TCCR

Covalent modifications of TCCR are included within the scope of this invention. One type of covalent modification includes reacting targeted amino acid residues of a TCCR polypeptide with an organic derivatizing agent that is capable of reacting with selected side chains or the N- or C-terminal residues of the TCCR. Derivatization with bifunctional agents is useful, for instance, for crosslinking the TCCR to a water-insoluble support matrix or surface for use in the method for purifying anti-TCCR antibodies, and vice-versa. Commonly used crosslinking agents include, e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio] propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties,* W.H. Freeman & Co., San Francisco, pp. 79-86 (1983)], acetylation of the N-terminal amine, and amidation of any C-terminal carboxyl group.

Another type of covalent modification of the invention polypeptide included within the scope of this invention comprises altering the native glycosylation pattern of the polypeptide. "Altering the native glycosylation pattern" is intended for purposes herein to mean deleting one or more carbohydrate moieties found in native sequence polypeptide (either by removing the underlying glycosylation site or by deleting the glycosylation by chemical and/or enzymatic means), and/or adding one or more glycosylation sites that are not present in the native sequence. In addition, the phrase includes qualitative changes in the glycosylation of the native proteins, involving a change in the nature and proportions of the various carbohydrate moieties present.

Addition of glycosylation sites to the polypeptide may be accomplished by altering the amino acid sequence. The alteration may be made, for example, by the addition of, or substitution by, one or more serine or threonine residues to the native sequence polypeptide (for O-linked glycosylation sites). The amino acid sequence may optionally be altered through changes at the DNA level, particularly by mutating the DNA encoding the polypeptide at preselected bases such that codons are generated that will translate into the desired amino acids.

Another means of increasing the number of carbohydrate moieties on the polypeptide of the invention is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.,* pp. 259-306 (1981).

Removal of carbohydrate moieties present on the polypeptide of the invention may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.,* 259:52 (1987) and by Edge et al., *Anal. Biochem.,* 118:131 (1981). Enzymatic cleavage of carbohydrate moieties on polypeptides can be achieved by the use of a variety of endo- and exo-glycosidases as described by Thotakura et al., *Meth. Enzymol.,* 138:350 (1987).

Another type of covalent modification comprises linking the invention polypeptide to one of a variety of nonproteinaceous polymers, e.g., polyethylene glycol (PEG), polypropylene glycol, or polyoxyalkylenes, in the manner set forth in U.S. Pat. No. 4,640,835; 4,496,689; 4,301,144; 4,670,417; 4,791,192 or 4,179,337.

The TCCR polypeptides of the present invention may also be modified in a way to form a chimeric molecule comprising the invention polypeptide fused to another, heterologous polypeptide or amino acid sequence.

In one embodiment, such a chimeric molecule comprises a fusion of the invention polypeptide with a tag polypeptide which provides an epitope to which an anti-tag antibody can selectively bind. The epitope tag is generally placed at the amino- or carboxyl-terminus of the polypeptide of the invention. The presence of such epitope-tagged forms of the polypeptide of the invention can be detected using an antibody against the tag polypeptide. Also, provision of the epitope tag enables the polypeptide of the invention to be readily purified by affinity purification using an anti-tag antibody or another type of affinity matrix that binds to the epitope tag. Various tag polypeptides and their respective antibodies are well known in the art. Examples include polyhistidine (poly-his) or poly-histidine-glycine (poly-his-gly) tags; the flu HA tag polypeptide and its antibody 12CA5 [Field et al., *Mol. Cell. Biol.,* 8:2159-2165 (1988)]; the c-myc tag and the 8F9, 3C7, 6E10, G4, B7 and 9E10 antibodies thereto [Evan et al., *Molecular and Cellular Biology,* 5:3610-3616 (1985)]; and the Herpes Simplex virus glycoprotein D (gD) tag and its antibody [Paborsky et al., *Protein Engineering,* 3(6):547-553 (1990)]. Other tag polypeptides include the Flag-peptide [Hopp et al., *BioTechnology,* 6:1204-1210 (1988)]; the KT3 epitope peptide [Martin et al., *Science,* 255:192-194 (1992)]; an α-tubulin epitope peptide [Skinner et al., *J. Biol. Chem.,* 266:15163-15166 (1991)]; and the T7 gene 10 protein peptide tag [Lutz-Freyermuth et al., *Proc. Natl. Acad. Sci. USA,* 87:6393-6397 (1990)].

In an alternative embodiment, the chimeric molecule may comprise a fusion of the polypeptide of the invention with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of an invention polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

D. Preparation of TCCR

The description below relates primarily to production of TCCR by culturing cells transformed or transfected with a vector containing TCCR nucleic acid. It is, of course, contemplated that alternative methods, which are well known in the art, may be employed to prepare TCCR. For instance, the TCCR sequence, or portions thereof, may be produced by direct peptide synthesis using solid-phase techniques (see, e.g., Stewart et al., Solid-Phase Peptide Synthesis, W.H. Freeman Co., San Francisco, Calif. (1969); Merrifield, *J. Am. Chem. Soc.* 85: 2149-2154 (1963)). In vitro protein synthesis may be performed using manual techniques or by automation. Automated synthesis may be accomplished, for instance, using an Applied Biosystems Peptide Synthesizer (Foster City, Calif.) using the manufacturer's instructions. Automated synthesis may be accomplished, for instance, using an Applied Biosystems Peptide Synthesizer (Foster City, Calif.) using manufacturer's instructions. Various portions of the TCCR may be chemically synthesized separately and combined using chemical or enzymatic methods to produce the full-length TCCR.

1. Isolation of DNA Encoding the Polypeptide of the Invention

DNA encoding TCCR may be obtained from a cDNA library prepared from tissue believed to possess the TCCR mRNA and to express it at a detectable level. Accordingly, human TCCR DNA can be conveniently obtained from a cDNA library prepared from human tissue, such as described in the Examples. The TCCR-encoding gene may also be obtained from a genomic library or by oligonucleotide synthesis.

Libraries can be screened with probes (such as antibodies to the polypeptide of the invention or oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding the polypeptide of the invention is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for TCCR production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: A Practical Approach*, M. Butler, ed. (IRL Press, 1991) and Sambrook et al., supra.

Methods of transfection are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 52:456-457 (1978) can be employed. General aspects of mammalian cell host system transformations have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527-537 (1990) and Mansour et al., *Nature*, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5772 (ATCC 53,635). Other suitable prokaryotic host cells include Enterobacteriaceae such as *Escherichia*, e.g., *E. coli* K12 strain MM294 (ATCC 31,446); *E. coli* X1776 (ATCC 31,537); *E. coli* strain W3110 (ATCC 27,325) and K5772 (ATCC 53,635), *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41P disclosed in DD266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant NDA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E coli* W3110 strain 27C7 (ATCC 55,244), which has the complete genotype tonA ptr3 phoA E15 (argF-lac) 169 degP ompT kan'; *E. coli* W3110 strain 37D6, which has the complete genotype tonA ptr3 phoA E15 (argF-lac) 169 degP ompT rbs7 ilvG kan; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase chain reactions, are suitable.

In addition to prokaryotes, eukaryotic microbes such as filamentous fungi or yeast are suitable cloning or expression hosts for TCCR encoding vectors. *Saccharomyces cerevisiae* is a commonly used lower eukaryotic host microorganism. Others include *Schizosaccharomyces pombe* (Beach and Nurse, *Nature* 290: 140 (1981); EP 139,383 published 2 May 1985); *Kluveromyces* hosts (U.S. Pat. No. 4,943,529; Fleer et al., *Bio/Technology* 9: 968-975 (1991)) such as, e.g., *K. lactis* (MW98-8C, CBS683, CBS4574; Louvencourt et al., *J. Bacteriol.* 154(2): 737 (1983); *K. fragilis* (ATCC 12,424), *K. bulgaricus* (ATCC 16,045), *K. wicheramii* (ATCC 24,178), *K. waltii* (ATCC 56,500), *K. drosopharum* (ATCC 36,906); Van den Berg et al., *Bio/Technology* 8: 135 (1990)), *K. thermotolerans*, and *K. marxianus; yarrowia* (EP 402,226); *Pichia pastoris* (EP 183,070); Sreekrishna et al., *J. Basic Microbiol.* 28: 265-278 (1988); *Candida; Trichoderma reesia* (EP 244,234); *Neurospora crassa* (Case et al., *Proc. Natl. Acad. Sci. USA,* 76:5259-5263 (1979); *Schwanniomyces* such as *Schwanniomyces occidentalis* (EP 394,538 published 31 Oct. 1990); and filamentous fungi such as, e.g., *Neurospora, Peniciliun, Tolypocladium* (WO 91/00357 published 10 Jan. 1991), and *Aspergillus* hosts such as *A. nidulans* (Ballance et al., *Biochem. Biophys. Res. Commun.* 112: 284-289 (1983); Tilburn et al., *Gene* 26: 205-221 (1983); Yelton et al., *Proc. Natl. Acad. Sci. USA* 81: 1470-1474 (1984)) and *A. niger* (Kelly and Hynes, *EMBO J.* 4: 475-479 (1985)). Methylotropic yeasts are suitable herein and include, but are not limited to, yeast capable of growth on methanol selected from the genera consisting of *Hansenula, Cadida, Kloeckera, Pichia, Saccharomyces, Torulopsis*, and *Rhodotorula*. A list of specific species that are exemplary of this class of yeasts may be found in C. Anthony, *The Biochemistry of Methylotrophs* 269 (1982).

Suitable host cells for the expression of glycosylated TCCR polypeptides are derived from multicellular organisms. Examples of invertebrate cells include insect cells such as *Drosophila* S2 and *Spodoptera* Sf9 and high five, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.,* 36:59 (1977)); Chinese hamster ovary cells/–DHFR(CHO, Urlaub and Chasin, *Proc. Natl. Acad. Sci. USA,* 77:4216 (1980)); mouse sertoli cells (Th4, Mather, *Biol. Reprod.,* 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding TCCR may be inserted into a replicable vector for cloning (amplification of the DNA) or for expression. Various vectors are publicly available. The vector may, for example, be in the form of a plasmid, cosmid, viral particle, phagemid or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The TCCR may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the TCCR-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including Saccharomyces and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the nucleic acid encoding the polypeptide of the invention, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA,* 77:4216 (1980). A suitable selection gene for use in yeast is the trp1 gene present in the yeast plasmid YRp7 [Stinchcomb et al., *Nature,* 282:39 (1979); Kingsman et al., *Gene,* 7:141 (1979); Tschemper et al., *Gene,* 10:157 (1980)]. The trp1 gene provides a selection marker for a mutant strain of yeast lacking the ability to grow in tryptophan, for example, ATCC No. 44076 or PEP4-1 [Jones, *Genetics,* 85:12 (1977)].

Expression and cloning vectors usually contain a promoter operably linked to the TCCR-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature,* 275:615 (1978); Goeddel et al., *Nature,* 281:544 (1979)], alkaline phosphatase, a tryptophan (trp) promoter system [Goeddel,

*Nucleic Acids Res.*, 8:4057 (1980); EP 36,776], and hybrid promoters such as the tac promoter [deBoer et al., *Proc. Natl. Acad. Sci. USA*, 80:21-25 (1983)]. Promoters for use in bacterial systems also will contain a Shine-Dalgarno (S.D.) sequence operably linked to the DNA encoding TCCR.

Examples of suitable promoting sequences for use with yeast hosts include the promoters for 3-phosphoglycerate kinase [Hitzeman et al., *J. Biol. Chem.*, 255:2073 (1980)] or other glycolytic enzymes [Hess et al., *J. Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

TCCR transcription of the polypeptide of the invention from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the TCCR by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the TCCR coding sequence of the polypeptide of the invention, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding TCCR.

Still other methods, vectors, and host cells suitable for adaptation to the synthesis of TCCR in recombinant vertebrate cell culture are described in Gething et al., *Nature*, 293:620-625 (1981); Mantei et al., *Nature*, 281:40-46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA*, 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of a duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence TCCR polypeptide or against a synthetic peptide based on the DNA sequences provided herein or against exogenous sequence fused to TCCR DNA encoding the polypeptide of the invention and encoding a specific antibody epitope.

5. Purification of Polypeptide

Forms of TCCR may be recovered from culture medium or from host cell lysates. If membrane-bound, it can be released from the membrane using a suitable detergent solution (e.g. Triton®-X 100) or by enzymatic cleavage. Cells employed in expression of the polypeptide of TCCR can be disrupted by various physical or chemical means, such as freeze-thaw cycling, sonication, mechanical disruption, or cell lysing agents.

It may be desired to purify TCCR from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the polypeptide of the invention. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular TCCR produced.

6. Tissue Distribution

The location of tissues expressing the polypeptides of the invention can be identified by determining mRNA expression in various human tissues. The location of such genes provides information about which tissues are most likely to be affected by the stimulating and inhibiting activities of the polypeptides of the invention. The location of a gene in a specific tissue also provides sample tissue for the activity blocking assays discussed below.

As noted before, gene expression in various tissues may be measured by conventional Southern blotting, Northern blotting to quantitate the transcription of mRNA (Thomas, *Proc. Natl. Acad. Sci. USA*, 77:5201-5205 [1980]), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes.

Gene expression in various tissues, alternatively, may be measured by immunological methods, such as immunohistochemical staining of tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence of a polypeptide of the invention or against a synthetic peptide based on the DNA sequences encoding the polypeptide of the invention or against an exogenous sequence fused to a DNA encoding a polypeptide of the invention and encoding a specific antibody epitope. General techniques for generating antibodies, and special protocols for Northern blotting and in situ hybridization are provided below.

E. Uses of TCCR

1. General Uses

TCCR is of the WS(G)XWS class of cytokine receptors with homology to the IL-12 β-2 receptor, G-CSFR and IL-6 receptor, the highest homology being to the IL-12 β-2 receptor (26% identity). These receptors transduce a signal that can control growth and differentiation of cells, especially cells involved in blood cell growth and differentiation. G-CSF, for example has found wide use in clinical applications for the proliferation of neutrophils after chemotherapy. These types of cytokine receptors and their agonists/antagonists are likely to play important roles in the treatment of hematological and oncological disorders. TCCR has been found to play a role in the T-helper cell response—in particular in the modulation of the differentiation of T-cells into the Th1 and Th2 subsets. As a result, TCCR and its agonists/antagonists may be useful in a therapeutic method to bias the mammalian immune response to either a T-helper 1 response (Th1) or a T-helper-2 (Th2) response depending on the desired therapeutic goal.

CD4+ T cells play a critical role in allergic inflammatory responses by enhancing the recruitment, growth and differentiation of all other cell types involved in the response. CD4+ cells perform this function by secreting several cytokines, including interleukin (IL-4) and IL-13, which enhance the induction of IgE synthesis in B cells, mast cell growth, and the recruitment of lymphocytes, mast cells, and basophils to the sites of inflammation. In addition, CD4+ T cells produce IL-5, which enhances the growth and differentiation of eosinophils and B cells, and IL-10, which enhances the growth and differentiation of mast cells and inhibits the production of γ-interferon. The combination of IL-4, IL-5, IL-10 and IL-13 is produced by a subset of CD4+ T-cells called Th2 cells, which are found in increased abundance in allergic individuals.

Th1 cells secrete cytokines important in the activation of macrophages (IFN-γ, IL-2, tumor necrosis factor-β [TNF-β]) and in inducing cell mediated immunity. Th2 cells secrete cytokines important in humoral immunity and allergic diseases (IL-4, IL-5 and IL-10). While Th1 cytokines inhibit the production of Th2 cytokines, Th2 cytokines inhibit the production of Th1 cytokines. This negative feedback loop accentuates the production of polarized cytokine profiles during immune responses. The maintenance of the delicate balance between the production of these "opposing" cytokines is critical, since overproduction of Th1 cytokines is believed to result in autoimmune inflammatory diseases and allograft rejection. Concomitantly, the overproduction of Th2 cytokines results in allergic inflammatory diseases such as asthma and allergic rhinitis, or ineffective immunity to intracellular pathogens.

Umetsu and DeKruyff, Proc. Soc. Exp. Bio. Med. 215(1): 11-20 (1997) have proposed a model wherein susceptability to infection is explained not as a lack of immunity, but rather to the development of T cells secreting an in appropriate cytokine profile. Allergic disease is caused by the CD4+ T cells inappropriately secreting Th2 cytokines, whereas non-allergic individuals remain asymptomatic because they develop T cells secreting Th1 cytokines, which inhibit IgE synthesis and mast cell and eosinophil differentiation. Stated another way, allergic rhinitis and asthma may represent a pathological aberration or oral/mucosal tolerance, where T cells that would normally develop into "Th2" regulatory/suppressor cells instead develop into "Th2" cells that initiate and intensify allergic inflammation.

Cytokine receptors are generally characterized by a multi-domain structure comprising an extracellular domain, a transmembrane domain and an intracellular domain. The extracellular domain usually functions to bind the ligand, the transmembrane domain anchors the receptor to the cell membrane, and the intracellular domain is usually an effector involved in signal transduction within the cell. However, ligand-binding and effector functions may reside on separate subunits of a multimeric receptor. The ligand-binding domain may itself have multiple domains. Multimeric receptors is a broad term which generally includes: (1) homodimer; (2) heterodimers having subunits with both ligand-binding and effector domains; and (3) multimers having component subunits with disparate functions. Cytokine receptors are further reviewed and classified in Urdahl, Ann. Reports Med. Chem. 26: 221-228 (1991) and Cosman, Cytokine 5: 95-106 (1993).

In addition to specific immune-related uses (e.g., Th1 and Th2 cells mediated physiology), nucleotide sequences (or their complement) encoding TCCR have various applications in the art of molecular biology, including uses as hybridization probes, in chromosome and gene mapping and in the generation of anti-sense RNA and DNA. TCCR nucleic acid will also be useful for the preparation of TCCR polypeptides by the recombinant techniques described herein.

The full-length native sequence TCCR genes encoding the polypeptides described in FIG. 3 (SEQ ID NO: 1) and FIG. 4 (SEQ ID NO:2), or portions thereof, may be used as hybridization probes for a cDNA library to isolate the full-length TCCR cDNA or to isolate still other cDNAs (for instance, those encoding naturally-occurring variants of TCCR or TCCR from other species) which have a desired sequence identity to the TCCR polynucleotide sequence encoding the polypeptides disclosed in FIGS. 3 and 4 (SEQ ID NO:s 1 &2, respectively). Optionally, the length of the probes will be about 20 to 50 bases. The hybridization probes may be derived from regions of the nucleotide sequence encoding the polypeptides of SEQ ID NO: 1&2 wherein those regions may be determined without undue experimentation or from genomic sequences including promoters, enhancer elements and introns of native sequence TCCR. By way of example, a screening method will comprise isolating the coding region of the TCCR gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the TCCR gene of the present invention can be used to screen libraries of human cDNA, genomic DNA or mRNA to determine to which members of such libraries the probe hybridizes. Hybridization techniques are described in further detail in the Examples below. Any EST or other sequence fragments disclosed herein may similarly be employed as probes, using the methods disclosed herein.

Other useful fragments of the TCCR nucleic acids include antisense or sense oligonucleotides comprising a single-stranded nucleic acid sequence (either RNA or DNA) capable of binding to target TCCR mRNA (sense) or TCCR DNA (antisense) sequences. Antisense or sense oligonucleotides, according to the present invention, comprise a fragment of the coding region of TCCR DNA. Such a fragment generally comprises at least about 14 nucleotides, preferably from about 14 to 30 nucleotides. The ability to derive an antisense or a sense oligonucleotide, based upon a cDNA sequence encoding a given protein is described in, for example, Stein and Cohen, Cancer Res. 48: 2659 (1988) and van der Krol et al., BioTechniques 6: 958 (1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. The antisense oligonucleotides thus may be used to block expression of TCCR proteins. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic digestion) but retain sequence specificity to be able to bind to target nucleotide sequences.

Other examples of sense or antisense oligonucleotides include those oligonucleotides which are covalently linked to organic moieties, such as those described in WO 90/10048, and other moieties that increase affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotides to modify binding specificities for the antisense or sense oligonucleotide for the target nucleotide sequence.

Antisense or sense oligonucleotides may be introduced into a cell containing the target nucleic acid sequence by any gene transfer method, including, for example, CaPO$_4$-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

The probes may also be employed in PCR techniques to generate a pool of sequences for identification of closely related TCCR coding sequences.

Nucleotide sequences encoding a TCCR can also be used to construct hybridization probes for mapping the gene which encodes that TCCR and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

Since TCCR is a receptor, the coding sequences for TCCR encode a protein which binds to another protein. As a result, the TCCR proteins of the invention can be used in assays to identify other proteins or molecules involved in the binding interaction. By such methods, inhibitors of the receptor/ligand binding interaction can be identified. Proteins involved in such binding interactions can also be used to screen for peptide or small molecule inhibitors or agonists of the binding interaction. Also, the receptor TCCR can be used to isolate correlative ligand(s). Screening assays can be used to find lead compounds that mimic the biological activity of a native TCCR or a ligand for TCCR. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

The TCCR polypeptides described herein may also be employed as molecular weight markers for protein electrophoresis purposes.

The nucleic acid molecules encoding the TCCR polypeptides or fragments thereof described herein are useful for chromosome identification. In this regard, there exists an ongoing need to identify new chromosome markers, since relatively few chromosome marking reagents, based upon actual sequence data are presently available. Each TCCR nucleic acid molecule of the present invention can be used as a chromosome marker.

The TCCR polypeptides and nucleic acid molecules of the present invention may also be used for tissue typing, wherein the TCCR polypeptides of the present invention may be differentially expressed in one tissue as compared to another. TCCR nucleic acid molecules will find use for generating probes for PCR, Northern analysis, Southern analysis and Western analysis.

2. Antibody Binding Studies

The activity of the TCCR polypeptides of the invention can be further verified by antibody binding studies, in which the ability of anti-TCCR antibodies to inhibit the effect of the TCCR polypeptides on tissue cells is tested. Exemplary antibodies include polyclonal, monoclonal, humanized, bispecific, and heteroconjugate antibodies, the preparation of which will be described hereinbelow.

Antibody binding studies may be carried out in any known assay method, such as competitive binding assays, direct and indirect sandwich assays, and immunoprecipitation assays. Zola, *Monoclonal Antibodies: A Manual of Techniques*, pp. 147-158 (CRC Press, Inc., 1987).

Competitive binding assays rely on the ability of a labeled standard to compete with the test sample analyte for binding with a limited amount of antibody. The amount of target protein in the test sample is inversely proportional to the amount of standard that becomes bound to the antibodies. To facilitate determining the amount of standard that becomes bound, the antibodies preferably are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the tissue sample may be fresh or frozen or may be embedded in paraffin and fixed with a preservative such as formalin, for example.

3. Cell-Based Assays

Cell-based assays and animal models for immune related diseases can be used to further understand the relationship between the genes and polypeptides identified herein and the development and pathogenesis of immune related disease.

In a different approach, cells of a cell type known to be involved in a particular immune related disease are transfected with the cDNAs described herein, and the ability of these cDNAs to stimulate or inhibit immune function is analyzed. Suitable cells can be transfected with the desired gene, and monitored for immune function activity. Such transfected cell lines can then be used to test the ability of poly- or monoclonal antibodies or antibody compositions to inhibit or stimulate immune function, for example to modulate T-cell proliferation or inflammatory cell infiltration. Cells transfected with the coding sequences of the genes identified herein can further be used to identify drug candidates for the treatment of immune related diseases.

In addition, primary cultures derived from transgenic animals (as described below) can be used in the cell-based assays herein, although stable cell lines are preferred. Techniques to derive continuous cell lines from transgenic animals are well known in the art (see, e.g. Small et al., *Mol. Cell. Biol.* 5, 642-648 [1985]).

One suitable cell based assay is the mixed lymphocyte reaction (MLR). *Current Protocols in Immunology*, unit 3.12; edited by J E Coligan, A M Kruisbeek, D H Marglies, E M Shevach, W Strober, National Institutes of Health, Published by John Wiley & Sons, Inc. In this assay, the ability of a test compound to stimulate or inhibit the proliferation of activated T cells is assayed. A suspension of responder T cells is cultured with allogeneic stimulator cells and the proliferation of T cells is measured by uptake of tritiated thymidine. This assay is a general measure of T cell reactivity. Since the majority of T cells respond to and produce IL-2 upon activation, differences in responsiveness in this assay in part reflect differences in IL-2 production by the responding cells. The MLR results can be verified by a standard lymphokine (IL-2) detection assay. *Current Protocols in Immunology*, above, 3.15, 6.3.

A proliferative T cell response in an MLR assay may be due to direct mitogenic properties of an assayed molecule or to external antigen induced activation. Additional verification of the T cell stimulatory activity of the polypeptides of the invention can be obtained by a costimulation assay. T cell activation requires an antigen specific signal mediated through the T-cell receptor (TCR) and a costimulatory signal mediated through a second ligand binding interaction, for example, the B7(CD80, CD86)/CD28 binding interaction. CD28 crosslinking increases lymphokine secretion by activated T cells. T cell activation has both negative and positive controls through the binding of ligands which have a negative or positive effect. CD28 and CTLA-4 are related glycoproteins in the Ig superfamily which bind to B7. CD28 binding to B7 has a positive costimulation effect of T cell activation; conversely, CTLA-4 binding to B7 has a negative T cell deactivating effect. Chambers, C. A. and Allison, J. P., *Curr. Opin. Immunol.* (1997) 9:396. Schwartz, R. H., *Cell* (1992) 71:1065; Linsey, P. S. and Ledbetter, J. A., *Annu. Rev. Immunol.* (1993) 11:191; June, C. H. et al., *Immunol. Today* (1994) 15:321; Jenkins, M. K., *Immunity* (1994) 1:405. In a costimulation assay, the polypeptides of the invention are assayed for T cell costimulatory or inhibitory activity.

Polypeptides of the invention, as well as other compounds of the invention, which are stimulators (costimulators) of T cell proliferation and agonists, e.g. agonist antibodies, thereto as determined by MLR and costimulation assays, for example, are useful in treating immune related diseases characterized by poor, suboptimal or inadequate immune function. These diseases are treated by stimulating the proliferation and activation of T cells (e.g., T cell mediated immunity, Th1 and/or Th2 cytokine production) and enhancing the immune response in a mammal through administration of a stimulatory compound, such as the stimulating polypeptides of the invention. The stimulating polypeptide may, for example, be a TCCR ligand polypeptide or an agonist antibody thereof.

Direct use of a stimulating compound as in the invention has been validated in experiments with 4-1BB glycoprotein, a member of the tumor necrosis factor receptor family, which binds to a ligand (4-1BBL) expressed on primed T cells and signals T cell activation and growth. Alderson, M. E. et al., *J. Immunol.* (1994) 24:2219.

The use of an agonist stimulating compound has also been validated experimentally. Activation of 4-1BB by treatment with an agonist anti-4-1BB antibody enhances eradication of tumors. Hellstrom, I. and Hellstrom, K. E., *Crit. Rev. Immunol.* (1998) 18:1. Immunoadjuvant therapy for treatment of tumors, described in more detail below, is another example of the use of the stimulating compounds of the invention.

An immune stimulating or enhancing effect can also be achieved by antagonizing or blocking the activity of a protein which has been found to be inhibiting in the MLR assay. Negating the inhibitory activity of the compound produces a net stimulatory effect. Suitable antagonists/blocking compounds are antibodies or fragments thereof which recognize and bind to the inhibitory protein, thereby blocking the effective interaction of the protein with its receptor and inhibiting signaling through the receptor. This effect has been validated in experiments using anti-CTLA-4 antibodies which enhance T cell proliferation, presumably by removal of the inhibitory signal caused by CTLA-4 binding. Walunas, T. L. et al., *Immunity* (1994) 1:405.

On the other hand, polypeptides of the invention, as well as other compounds of the invention, which are direct inhibitors of T cell proliferation/activation and/or lymphokine secretion, can be directly used to suppress the immune response. These compounds are useful to reduce the degree of the immune response and to treat immune related diseases characterized by a hyperactive, superoptimal, or autoimmune response. This use of the compounds of the invention may be validated by the experiments described above in which CTLA-4 binding to receptor B7 deactivates T cells. The direct inhibitory compounds of the invention function in an analogous manner.

Alternatively, compounds, e.g. antibodies, which bind to stimulating polypeptides of the invention and block the stimulating effect of these molecules produce a net inhibitory effect and can be used to suppress the T cell mediated immune response by inhibiting T cell proliferation/activation and/or lymphokine secretion. Blocking the stimulating effect of the polypeptides suppresses the immune response of the mammal. This use has been validated in experiments using an anti-IL2 antibody. In these experiments, the antibody binds to IL2 and blocks binding of IL2 to its receptor thereby achieving a T cell inhibitory effect.

4. Animal Models

The results of the cell based in vitro assays can be further verified using in vivo animal models and assays for T-cell function. A variety of well known animal models can be used to further understand the role of the genes identified herein in the development and pathogenesis of immune related disease, and to test the efficacy of candidate therapeutic agents, including antibodies, and other antagonists of the native polypeptides, including small molecule antagonists. The in vivo nature of such models makes them predictive of responses in human patients. Animal models of immune related diseases include both non-recombinant and recombinant (transgenic) animals. Non-recombinant animal models include, for example, rodent, e.g., murine models. Such models can be generated by introducing cells into syngeneic mice using standard techniques, e.g. subcutaneous injection, tail vein injection, spleen implantation, intraperitoneal implantation, implantation under the renal capsule, etc.

Graft-versus-host disease occurs when immunocompetent cells are transplanted into immunosuppressed or tolerant patients. The donor cells recognize and respond to host antigens. The response can vary from life threatening severe inflammation to mild cases of diarrhea and weight loss. Graft-versus-host disease models provide a means of assessing T cell reactivity against MHC antigens and minor transplant antigens. A suitable procedure is described in detail in Current Protocols in Immunology, above, unit 4.3.

An animal model for skin allograft rejection is a means of testing the ability of T cells to mediate in vivo tissue destruction and a measure of their role in transplant rejection. The most common and accepted models use murine tail-skin grafts. Repeated experiments have shown that skin allograft rejection is mediated by T cells, helper T cells and killer-effector T cells, and not antibodies. Auchincloss, H. Jr. and Sachs, D. H., *Fundamental Immunology,* 2nd ed., W. E. Paul ed., Raven Press, NY, 1989, 889-992. A suitable procedure is described in detail in *Current Protocols in Immunology*, above, unit 4.4. Other transplant rejection models which can be used to test the compounds of the invention are the allogeneic heart transplant models described by Tanabe, M. et al., *Transplantation* (1994) 58:23 and Tinubu, S. A. et al., *J. Immunol.* (1994) 4330-4338.

Animal models for delayed type hypersensitivity provides an assay of cell mediated immune function as well. Delayed type hypersensitivity reactions are a T cell mediated in vivo immune response characterized by inflammation which does not reach a peak until after a period of time has elapsed after challenge with an antigen. These reactions also occur in tissue specific autoimmune diseases such as multiple sclerosis (MS) and experimental autoimmune encephalomyelitis (EAE, a model for MS). A suitable procedure is described in detail in *Current Protocols in Immunology*, above, unit 4.5.

EAE is a T cell mediated autoimmune disease characterized by T cell and mononuclear cell inflammation and subsequent demyelination of axons in the central nervous system. EAE is generally considered to be a relevant animal model for MS in humans. Bolton, C., *Multiple Sclerosis* (1995) 1:143. Both acute and relapsing-remitting models have been developed. The compounds of the invention can be tested for T cell stimulatory or inhibitory activity against immune mediated demyelinating disease using the protocol described in *Current Protocols in Immunology*, above, units 15.1 and 15.2. See also the models for myelin disease in which oligodendrocytes or Schwann cells are grafted into the central nervous system as described in Duncan, I. D. et al., *Molec. Med. Today* (1997) 554-561.

Contact hypersensitivity is a simple delayed type hypersensitivity in vivo assay of cell mediated immune function. In this procedure, cutaneous exposure to exogenous haptens which gives rise to a delayed type hypersensitivity reaction which is measured and quantitated. Contact sensitivity involves an initial sensitizing phase followed by an elicitation phase. The elicitation phase occurs when the T lymphocytes encounter an antigen to which they have had previous contact. Swelling and inflammation occur, making this an excellent model of human allergic contact dermatitis. A suitable procedure is described in detail in *Current Protocols in Immunology*, Eds. J. E. Cologan, A. M. Kruisbeek, D. H. Margulies, E. M. Shevach and W. Strober, John Wiley & Sons, Inc., 1994, unit 4.2. See also Grabbe, S. and Schwarz, T, *Immun. Today* 19(1):37-44 (1998).

An animal model for arthritis is collagen-induced arthritis. This model shares clinical, histological and immunological characteristics of human autoimmune rheumatoid arthritis and is an acceptable model for human autoimmune arthritis. Mouse and rat models are characterized by synovitis, erosion of cartilage and subchondral bone. The compounds of the invention can be tested for activity against autoimmune arthritis using the protocols described in *Current Protocols in Immunology*, above, units 15.5. See also the model using a monoclonal antibody to CD18 and VLA-4 integrins described in Issekutz, A. C. et al., *Immunology* (1996) 88:569.

A model of asthma has been described in which antigen-induced airway hyper-reactivity, pulmonary eosinophilia and inflammation are induced by sensitizing an animal with ovalbumin and then challenging the animal with the same protein delivered by aerosol. Several animal models (guinea pig, rat, non-human primate) show symptoms similar to atopic asthma in humans upon challenge with aerosol antigens. Murine models have many of the features of human asthma. Suitable procedures to test the compounds of the invention for activity and effectiveness in the treatment of asthma are described by Wolyniec, W. W. et al., *Am. J. Respir. Cell Mol. Biol.* (1998) 18:777 and the references cited therein.

Additionally, the compounds of the invention can be tested on animal models for psoriasis like diseases. Evidence suggests a T cell pathogenesis for psoriasis. The compounds of the invention can be tested in the scid/scid mouse model described by Schon, M. P. et al., *Nat. Med.* (1997) 3:183, in which the mice demonstrate histopathologic skin lesions resembling psoriasis. Another suitable model is the human skin/scid mouse chimera prepared as described by Nickoloff, B. J. et al., *Am. J. Pathol.* (1995) 146:580.

Recombinant (transgenic) animal models can be engineered by introducing the coding portion of the genes identified herein into the genome of animals of interest, using standard techniques for producing transgenic animals. Animals that can serve as a target for transgenic manipulation include, without limitation, mice, rats, rabbits, guinea pigs, sheep, goats, pigs, and non-human primates, e.g. baboons, chimpanzees and monkeys. Techniques known in the art to introduce a transgene into such animals include pronucleic microinjection (Hoppe and Wanger, U.S. Pat. No. 4,873,191); retrovirus-mediated gene transfer into germ lines (e.g., Van der Putten et al., *Proc. Natl. Acad. Sci. USA* 82: 6148-615 [1985]); gene targeting in embryonic stem cells (Thompson et al., *Cell* 56: 313-321 [1989]); electroporation of embryos (Lo, *Mol. Cel. Biol.* 3, 1803-1814 [1983]); sperm-mediated gene transfer (Lavitrano et al., *Cell* 57, 717-73 [1989]). For review, see, for example, U.S. Pat. No. 4,736,866.

For the purpose of the present invention, transgenic animals include those that carry the transgene only in part of their cells ("mosaic animals"). The transgene can be integrated either as a single transgene, or in concatamers, e.g., head-to-head or head-to-tail tandems. Selective introduction of a transgene into a particular cell type is also possible by following, for example, the technique of Lasko et al., *Proc. Natl. Acad. Sci. USA* 89, 6232-636 (1992).

The expression of the transgene in transgenic animals can be monitored by standard techniques. For example, Southern blot analysis or PCR amplification can be used to verify the integration of the transgene. The level of mRNA expression can then be analyzed using techniques such as in situ hybridization, Northern blot analysis, PCR, or immunocytochemistry.

The animals may be further examined for signs of immune disease pathology, for example by histological examination to determine infiltration of immune cells into specific tissues. Blocking experiments can also be performed in which the transgenic animals are treated with the compounds of the invention to determine the extent of the T cell proliferation stimulation or inhibition of the compounds. In these experiments, blocking antibodies which bind to the polypeptide of the invention, prepared as described above, are administered to the animal and the effect on immune function is determined.

Nucleic acids which encode TCCR or its modified forms can also be used to generate either transgenic animals or "knock out" animals which, in turn, are useful in the development and screening of therapeutically useful reagents. The term "knockout" is used in the art to describe a transgenic animal in which the endogenous gene has been "knocked out" or ablated such as that which results from the use of homologous recombination. Homologous recombination is a term of art used to describe the regions of the targeting vector that are homologous to the endogenous gene. These regions of homology will hybridize to each other and recombine to the host's genome resulting with the replacement of the host endogenous sequence with the vector insert sequence at the location and in the orientation defined by the regions of shared homology. The genotype of a knockout animal is denoted by the name of the gene followed by a "−/−". This distinguishes it from an animal in which only one allele has been "knocked-out" (heterozygous) which is termed "−/+". An endogenous gene that has been "knocked out" is no longer expressed in all cells throughout the animal. Detailed analysis of specific cells can identify the function of the ablated gene.

A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding TCCR can be used to clone genomic DNA encoding TCCR in accordance with established techniques and the genomic sequences used to generate transgenic animals that contain cells which express DNA encoding TCCR. Methods for generating transgenic animals, particularly animals such as mice or rats, have become conventional in the art and are described, for example, in U.S. Pat. Nos. 4,736,866 and 4,870,009. Typically, particular cells would be targeted for TCCR transgene incorporation with tissue-specific enhancers. Transgenic animals that include a copy of a transgene encoding TCCR introduced into the germ line of the animals at an embryonic stage can be used to examine the effect of increased expression of DNA encoding TCCR. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, "knock out" animals can be constructed which have a defective or altered gene encoding a polypeptide identified herein, as a result of homologous recombination between the endogenous gene encoding the polypeptide and altered genomic DNA encoding the same polypeptide introduced into an embryonic cell of the animal. For example, cDNA encoding a particular polypeptide can be used to clone genomic DNA encoding that polypeptide in accordance with established techniques. A portion of the genomic DNA encoding a particular polypeptide can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell,* 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell,* 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the polypeptide.

For the present invention, knockout mice were created in order to study the effect of TCCR agonization/antagonization of the Th1 and/or Th2 immune response and disorders mediated thereby.

5. Chimeric Receptors

Additionally, chimeric receptors can be recreated to determine the effect of signaling by a receptor having an unknown ligand. Chimeric receptors are a proven means of examining the function of a receptor's function without isolation of the ligand. Chang et al., *Mol. Cell Biol.* 18(2): 896-905 (1998).

6. ImmunoAdjuvant Therapy

In one embodiment, the immunostimulating compounds of the invention can be used in immunoadjuvant therapy for the treatment of tumors (cancer). It is now well established that T cells recognize human tumor specific antigens. One group of tumor antigens, encoded by the MAGE, BAGE and GAGE families of genes, are silent in all adult normal tissues, but are expressed in significant amounts in tumors, such as melanomas, lung tumors, head and neck tumors, and bladder carcinomas. DeSmet, C. et al., (1996) *Proc. Natl. Acad. Sci. USA,* 93:7149. It has been shown that costimulation of T cells induces tumor regression and an antitumor response both in vitro and in vivo. Melero, I. et al., *Nature Medicine* (1997) 3:682; Kwon, E. D. et al., *Proc. Natl. Acad. Sci. USA* (1997) 94:8099; Lynch, D. H. et al., *Nature Medicine* (1997) 3:625; Finn, O. J. and Lotze, M. T., *J. Immunol.* (1998) 21:114. The stimulatory compounds of the invention can be administered as adjuvants, alone or together with a growth regulating agent, cytotoxic agent or chemotherapeutic agent, to stimulate T cell proliferation/activation and an antitumor response to tumor antigens. The growth regulating, cytotoxic, or chemotherapeutic agent may be administered in conventional amounts using known administration regimes. Immunostimulating activity by the compounds of the invention allows reduced amounts of the growth regulating, cytotoxic, or chemotherapeutic agents thereby potentially lowering the toxicity to the patient.

7. Screening Assays for Drug Candidates

Screening assays for drug candidates are designed to identify compounds that bind to or complex with the polypeptides encoded by the TCCR nucleic acids identified herein or a biologically active variant thereof, or otherwise interfere with the interaction of the encoded polypeptides with other cellular proteins. Such screening assays will include assays amenable to high-throughput screening of chemical libraries, making them particularly suitable for identifying small molecule drug candidates. Small molecules contemplated include synthetic organic or inorganic compounds, including peptides, preferably soluble peptides, (poly)peptide-immunoglobulin fusions, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments.

The assays can be performed in a variety of formats, including protein-protein binding assays, biochemical screening assays, immunoassays and cell based assays, which are well characterized in the art. All of the drug candidate screening assays identified herein have the property in common that they call for contacting the drug candidate with an TCCR polypeptide under conditions and for a time sufficient to allow these two molecules to interact.

In binding assays, the interaction is binding and the complex formed can be isolated or detected in the reaction mixture. Since the TCCR polypeptides of the present invention are receptors, a TCCR ECD fragment may also be suitably employed for the purpose of identifying drug candidates including TCCR variants, antagonists thereof and/or agonists thereof. In a particular embodiment, the polypeptide encoded by the gene identified herein or the drug candidate is immobilized on a solid phase, e.g. on a microtiter plate, by covalent or non-covalent attachments. Non-covalent attachment generally is accomplished by coating the solid surface with a solution of the polypeptide and drying. Alternatively, an immobilized antibody, e.g. a monoclonal antibody, specific for the polypeptide to be immobilized can be used to anchor it to a solid surface. The assay is performed by adding the non-immobilized component, which may be labeled by a detectable label, to the immobilized component, e.g. the coated surface containing the anchored component. When the reaction is complete, the non-reacted components are removed, e.g. by washing, and complexes anchored on the solid surface are detected. When the originally non-immobilized component carries a detectable label, the detection of label immobilized on the surface indicates that complexing has occurred. Where the originally non-immobilized component does not carry a label, complexing can be detected, for example, by using a labelled antibody specifically binding the immobilized complex.

If the candidate compound interacts with but does not bind to a particular TCCR protein identified herein, its interaction with that protein can be assayed by methods well known for detecting protein-protein interactions. Such assays include traditional approaches, such as, cross-linking, co-immunoprecipitation, and co-purification through gradients or chromatographic columns. In addition, protein-protein interactions can be monitored by using a yeast-based genetic system described by Fields and co-workers [Fields and Song, *Nature* (*London*) 340, 245-246 (1989); Chien et al., *Proc. Natl. Acad. Sci. USA* 88: 9578-9582 (1991)] as disclosed by Chevray and Nathans [*Proc. Natl. Acad. Sci. USA* 89: 5789-5793 (1991)]. Many transcriptional activators, such as yeast GAL4, consist of two physically discrete modular domains, one acting as the DNA-binding domain, while the other one functioning as the transcription activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

In order to find compounds that interfere with the interaction of a TCCR polypeptide identified herein and other intra- or extracellular components can be tested, a reaction mixture is usually prepared containing the product of the gene and the intra- or extracellular component under conditions and for a time allowing for the interaction and binding of the components. To test the ability of a test compound to inhibit the above interactions, the reaction is run in the absence and in the presence of the test compound. In addition, a placebo may be added to a third reaction mixture, to serve as a positive control. The binding (complex formation) between the test compound and the intra- or extracellular component present in the mixture is monitored as described above. The formation of a complex in the control reaction(s) but not in the reaction mixture containing the test compound indicates that the test compound interferes with the interaction of the test compound and its reaction partner.

8. Compositions and Methods for the Treatment of Immune Related Diseases

The compositions useful in the treatment of immune related diseases (e.g., Th1- and/or Th2-mediated disorders) include, without limitation, proteins, antibodies, small organic molecules, peptides, phosphopeptides, antisense and ribozyme molecules, triple helix molecules, etc. that inhibit or stimulate immune function, for example, T cell proliferation/activation, lymphokine release, or immune cell infiltration.

For example, antisense RNA and RNA molecules act to directly block the translation of mRNA by hybridizing to targeted mRNA and preventing protein translation. When antisense DNA is used, oligodeoxyribonucleotides derived from the translation initiation site, e.g. between about –10 and +10 positions of the target gene nucleotide sequence, are preferred.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g. Rossi, *Current Biology* 4: 469-471 (1994), and PCT publication No. WO 97/33551 (published Sep. 18, 1997).

Nucleic acid molecules in triple helix formation used to inhibit transcription should be single-stranded and composed of deoxynucleotides. The base composition of these oligonucleotides is designed such that it promotes triple helix formation via Hoogsteen base pairing rules, which generally require sizeable stretches of purines or pyrimidines on one strand of a duplex. For further details see, e.g. PCT publication No. WO 97/33551, supra.

These molecules can be identified by any or any combination of the screening assays discussed above and/or by any other screening techniques well known for those skilled in the art.

The TCCR polypeptides, agonists and antagonists (TCCR molecules) described herein may also be employed as therapeutic agents. The TCCR molecules of the present invention can be formulated according to known methods to prepare pharmaceutically useful compositions, whereby the TCCR molecule is combined in combination with a pharmaceutically acceptable carrier vehicle. Therapeutic formulations are prepared for storage by mixing the TCCR molecules having the desired degree of purity with optional physiologically acceptable carriers, excipients or stabilizers, *Remington's Pharmaceutical Sciences* 16th edition. Osol. A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose or dextrins; chelating agents such as EDTA; sugar alcohols such as mannitol or sorbitol; salt-forming counterions such as sodium; and/or nonionic surfactants such as TWEEN®, PLURONICS® or PEG.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having as stopper pierceable by a hypodermic injection needle.

The route of administration is in accord with known methods, e.g., injection or infusion by intravenous, intraperitoneal, intracerebral, intramuscular, intraocular, intraarterial or intralesional routes, topical administration, or by sustained release systems.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" in *Toxicokinetics and New Drug Development*, Yacobi et al., Eds., Pergamon Press, New York 1989, pp. 42-96.

When in vivo administration of a TCCR molecules thereof is employed, normal dosage amounts may vary from about 10 ng/kg to up to 100 mg/kg of mammal body weight or more per day, preferably about 1 µg/kg/day to 10 mg/kg/day, depending upon the route of administration. Guidance as to particular dosages and methods of delivery is provided in the literature; see, for example, U.S. Pat. No. 4,657,760; 5,206,344 or 5,225,212. It is anticipated that different formulations will be effective for different treatments and different disorders, and that administration intended to treat a specific organ or tissue, may necessitate delivery in a manner different from that to another organ or tissue.

Where sustained-release administration of TCCR molecules is desired in a formulation with release characteristics suitable for the treatment of any disease or disorder requiring administration of the TCCR molecules, microencapsulation of the TCCR molecules is contemplated. Microencapsulation of recombinant proteins for sustained release has been successfully performed with human growth hormone (rhGH), interferon-α, -β, -γ (rhIFN-α, -β, -γ), interleukin-2, and MN rgp120. Johnson et al., Nat. Med. 2: 795-799 (1996); Yasuda, *Biomed. Ther.* 27: 1221-1223 (1993); Hora et al., *Bio/Technology* 8: 755-758 (1990); Cleland, "Design and Production of Single Immunization Vaccines Using Polylactide Polyglycolide Microsphere Systems" in *Vaccine Design: The Subunit and Adjuvant Approach*, Powell and Newman, eds., (Plenum Press: New York, 1995), pp. 439-462; WO 97/03692, WO 96/40072, WO 96/07399 and U.S. Pat. No. 5,654,010.

The sustained-release formulations of TCCR molecules may be developed using poly-lactic-coglycolic acid (PLGA), a polymer exhibiting a strong degree of biocompatibility and a wide range of biodegradable properties. The degradation products of PLGA, lactic and glycolic acids, are cleared quickly from the human body. Moreover, the degradability of this polymer can be adjusted from months to years depending on its molecular weight and composition. For further information see Lewis, "Controlled Release of Bioactive Agents from Lactide/Glycolide polymer," in *Biogradable Polymers as Drug Delivery Systems* M. Chasin and R. Langeer, editors (Marcel Dekker: New York, 1990), pp. 141.

9. Identification of Agonists and Antagonists of TCCR

The present invention also provides for methods of screening compounds to identify those that mimic or enhances a TCCR polypeptide effect (agonists) or prevent or inhibit one or more functions or activities of an TCCR polypeptide. Preferably such antagonists and agonists are TCCR variants, peptide fragments small molecules, antisense oligonucleotides (DNA or RNA) or antibodies (monoclonal, humanized, specific, single-chain, heteroconjugate or fragment of the aforementioned). Additionally, TCCR antagonists can include potential TCCR ligands, while potential TCCR agonists can include soluble TCCR extracellular domains (ECD).

Screening assays for antagonist and/or agonist drug candidates are designed to identify compounds that bind or complex with the TCCR polypeptides encoded by the genes identified herein, or otherwise interfere with the interaction of the encoded polypeptides with other cellular proteins. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

The screening assays contemplated herein for antagonists have in common the process of contacting the drug candidate with a TCCR polypeptide under conditions and for a time sufficient to allow these two components to interact.

Examples of suitable assays useful to identify TCCR antagonists and agonists have been identified previously above under 7. *Screening Assays for Drug Candidates.*

As an additional example of an antagonists assay, the TCCR polypeptide may be added to a cell along with the compound to be screened for a particular activity and the ability of the compound to inhibit the activity of interest in the presence of the TCCR polypeptide indicates that the compound is an antagonist to the TCCR polypeptide. Alternatively, antagonists may be detected by combining the TCCR polypeptide and a potential antagonist with membrane-bound TCCR polypeptide receptors or recombinant receptors under appropriate conditions for a competitive inhibition assay. The TCCR polypeptide can be labeled, such as by radioactivity, such that the number of TCCR polypeptide molecules bound to the receptor can be used to determine the effectiveness of the potential antagonist. The gene encoding the receptor can be identified by numerous methods known to those of skill in the art, for example, ligand panning and FACS sorting. Coligan et al., *Current Protocols in Immunol.* 1(2): Ch 5 (1991). Preferably, expression cloning is employed wherein polyadenylated RNA is prepared from a cell responsive to the TCCR polypeptide and a cDNA library created from this RNA is divided into pools and used to transfect COS cells or other cells that are not responsive to the TCCR polypeptide. Transfected cells that are grown on glass slides are exposed to labeled TCCR polypeptide. The TCCR polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

In another assay for antagonists, mammalian cells or a membrane preparation expressing the receptor would be incubated with labeled TCCR polypeptide in the presence of the candidate compound. The ability of the compound to enhance or block this interaction could then be measured.

More specific examples of potential antagonists include an oligonucleotide that binds to the fusions of immunoglobulin with TCCR polypeptide, and in particular, antibodies including, without limitation, poly- and monoclonal antibodies and antibody fragments, single chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the TCCR polypeptide that recognized the ligand but imparts no effect, thereby competitively inhibiting the action of the TCCR polypeptide. Finally, another potential TCCR antagonist is a TCCR ECD which can compete for available ligand, effectively leaving the native TCCR receptor signal free.

Another potential TCCR polypeptide antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA.

For example, the 5' coding portion of the polynucleotide sequence, which encodes the mature TCCR polypeptides herein, is used to design an antisense RNA oligonucleotide from about 10 to 40 base pairs in length. A DNA oligonucleotide is designed to be complementary to a region of the gene involved in transcription (triple helix—see Lee et al., *Nucl. Acids. Res.* 6: 3073 (1979); Cooney et al. *Science* 241: 456 (1988); Dervan et al., *Science,* 251: 1360 (1991)), thereby preventing transcription and the production of the TCCR polypeptide. The antisense RNA oligonucleotide hybridizes to the mRNA in vivo and blocks translation of the mRNA molecule into the TCCR polypeptide (antisense—Okano, *Nerochem.* 56: 560 (1991); Oligodeoxynucleotides as Antisense Inhibitors of Gene. Expression (CRC Press: Boca Raton, Fla., 1988). The oligonucleotides described above can also be delivered to cells such that the antisense RNA or DNA may be expressed in vivo to inhibit production of the TCCR polypeptide. When antisense DNA is used, oligodeoxyribonucleotides derived from the translation-initiation site, e.g., between about −10 and +10 positions of the target gene nucleotide sequence are preferred.

Potential antagonists include small molecules that bind to the active site, the receptor binding site, or growth factor or other relevant binding site of the TCCR polypeptide, thereby blocking the normal biological activity of the TCCR polypeptide. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details, see, e.g. Rossi, *Current Biology,* 4: 469-471 (1994), and PCR publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details, see, e.g., PCT publication No. WO 97/33551, supra.

These molecules can be identified by any one or more of the screening assays used hereinabove and/or by any other screening techniques well known for those skilled in the art.

10. TCCR and Gene Therapy

Nucleic acid encoding the TCCR polypeptides may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective amount of DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. Zamecnik et al., *Proc. Natl. Acad. Sci. USA* 83:4143-4146 (1986)). The oligonucleotides can be modified to enhance their uptake, e.g., by substituting their negatively charged phosphodiester groups by uncharged groups.

There are a variety of techniques available for introducing nucleic acids into viable cells. The techniques vary depending upon whether the nucleic acid is transferred into cultured cells in vitro, or in viva in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in viva gene transfer techniques include transfection with viral (typically retroviral) vectors and viral coat protein-liposome mediated transfection (Dzau et al., *Trends in Biotechnology* 11: 205-210 (1993)). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g., capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Bio. Chem.* 262: 4429-4432 (1987); and Wagner et al., *Proc. Natl. Acad. Sci. USA* 87: 3410-3414 (1990). For review of gene marking and gene therapy protocols see Anderson et al., *Science* 256: 808-813 (1992).

11. Antibodies

The present invention further provides anti-TCCR antibodies. Exemplary antibodies include polyclonal, monoclonal, humanized, bispecific, and heteroconjugate antibodies, including antibody fragments which may inhibit (antagonists) or stimulate (agonists) T cell proliferation, eosinophil infiltration, etc.

i. Polyclonal Antibodies

The anti-TCCR antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the TCCR polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

ii. Monoclonal Antibodies

The anti-TCCR antibodies may, alternatively, be monoclonal antibodies. Monoclonal antibodies may be prepared using hybridoma methods, such as those described by Kohler and Milstein, *Nature,* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the TCCR polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies [Kozbor, *J. Immunol,* 133:3001 (1984); Brodeur et al., *Monoclonal Antibody Production Techniques and Applications*, Marcel Dekker, Inc., New York, (1987) pp. 51-63].

The culture medium in which the hybridoma cells are cultured can then be assayed for the presence of monoclonal antibodies directed against TCCR. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.* 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxyapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

iii. Human and Humanized Antibodies

The anti-TCCR antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature,* 321:522-525 (1986); Riechmann et al., *Nature,* 332:323-329 (1988); and Presta, *Curr. Op. Struct. Biol.,* 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and coworkers [Jones et al., *Nature,* 321:522-525 (1986); Riechmann et al., *Nature,* 332:323-327 (1988); Verhoeyen et al., *Science,* 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.,* 227:381 (1991); Marks et al., *J. Mol. Biol.* 222:581 (1991)]. The techniques of Cole et al. and Boerner et al. are also available for the preparation of human monoclonal antibodies (Cole et al., *Monoclonal Antibodies and Cancer Therapy,* Alan R. Liss, p. 77 (1985); Boerner et al., *J. Immunol.,* 147(1):86-95 (1991); U.S. Pat. No. 5,750,373]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10, 779-783 (1992); Lonberg et al., *Nature* 368: 856-859 (1994); Morrison, *Nature* 368: 812-13 (1994); Fishwild et al., *Nature Biotechnology* 14: 845-51 (1996); Neuberger, *Nature Biotechnology* 14: 826 (1996); Lonberg and Huszar, *Intern. Rev. Immunol.* 13: 65-93 (1995).

The antibodies may also be affinity matured using known selection and/or mutagenesis methods as described above. Preferred affinity matured antibodies have an affinity which is five times, more preferably 10 times, even more preferably 20 or 30 times greater than the starting antibody (generally murine, humanized or human) from which the matured antibody is prepared.

iv. Bispecific Antibodies

Bispecific antibodies are monoclonal, preferably human or humanized, antibodies that have binding specificities for at least two different antigens. In the present case, one of the binding specificities may be for the polypeptide of the invention, the other one is for any other antigen, and preferably for a cell-surface protein or receptor or receptor subunit.

Methods for making bispecific antibodies are known in the art. Traditionally, the recombinant production of bispecific antibodies is based on the coexpression of two immunoglobulin heavy-chain/light-chain pairs, where the two heavy chains have different specificities (Milstein and Cuello, *Nature,* 305:537-539 [1983]). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., *EMBO J.,* 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are cotransfected into a suitable host organism. For further details of generating bispecific antibodies see, for example, Suresh et al., *Methods in Enzymology,* 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains form the interface of the first antibody molecule are replaced with larger side chains (e.g., tryosine or tryptophan). Compensatory "cavities" of identical or similar size to the large chain(s) are created on the interface of the second antibody molecule by replacing large amino acid side chains with small ones (e.g., alanine or threonine). This provides a mechanism for increasing the yield of the heterodimer over other unwanted end-products such as homodimers.

Bispecific antibodies can be prepared as full length antibodies or antibody fragments (e.g., F(ab')$_2$ bispecific antibodies). Techniques for generating bispecific antibodies from antibody fragments have been described in the literature. For example, bispecific antibodies can be prepared using chemical linkage. Brennan et al., *Science* 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby et al., *J. Exp. Med.* 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques are known for making and isolating bispecific antibody fragments directly from recombinant cell culture. For example, bispecific antibodies have been produced using leucine zippers. Kostelny et al., *J. Immunol.* 148(5): 1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444-6448 (1993) has provided as alternative mechanism for making bispecific antibody fragments. The fragments comprise a heavy-chain variable domain (VH) connected to a light-chain variable domain (VL) by a linker which it too short to allow paring between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See, Gruger et al., *J. Immunol.* 152:5368 (1994). Antibodies with more than two valencies are contemplated. For example, trispecific antibodies can be prepared. Tutt et al., *J. Immunol.* 147: 60 (1991).

Exemplary bispecific antibodies may bind to two different epitopes on a given TCCR polypeptide. Alternatively, an anti-TCCR polypeptide arm may be combined with an arm which binds to a triggering molecule on a leukocyte such as a T-cell receptor molecule (e.g., CD2, CD3, CD28 or B7), or Fc receptors for IgG (FcγR), such as FcγRI (CD64), FcγRII (CD32) and FcγRIII (CD6) so as to focus cellular defense mechanisms to the cell expressing the particular TCCR polypeptide. Bispecific antibodies may also be used to localize cytotoxic agents to cells which express a particular TCCR polypeptide. These antibodies possess a TCCR-binding arm and an arm which binds a cytotoxic agent or a radionucleotide chelator, such as EOTUBE, DPTA, DOTA, or TETA. Another bispecific antibody of interest binds the TCCR polypeptide and further binds tissue factor (TF).

v. Heteroconjugate Antibodies

Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

vi. Effector Function Engineering

It may be desirable to modify the antibody of the invention with respect to effector function, so as to enhance the effectiveness of the antibody in treating an immune related disease, for example. For example cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al. *Cancer Research* 53:2560-2565 (1993). Alternatively, an antibody can be engineered which has dual Fc regions and may thereby have enhanced complement lysis and ADCC capabilities. See Stevenson et al., *Anti-Cancer Drug Design* 3:219-230 (1989).

vii. Immunoconjugates

The invention also pertains to immunoconjugates comprising an antibody conjugated to a cytotoxic agent such as a chemotherapeutic agent, toxin (e.g. an enzymatically active toxin of bacterial, fungal, plant or animal origin, or fragments thereof), or a radioactive isotope (i.e., a radioconjugate).

Chemotherapeutic agents useful in the generation of such immunoconjugates have been described above. Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. A variety of radionuclides are available for the production of radioconjugated antibodies. Examples include $^{212}$Bi, $^{131}$I, $^{131}$In, $^{90}$Y and $^{186}$Re.

Conjugates of the antibody and cytotoxic agent are made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody may be conjugated to a "receptor" (such as streptavidin) for utilization in tissue pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

viii. Immunoliposomes

The proteins, antibodies, etc. disclosed herein may also be formulated as immunoliposomes. Liposomes containing the antibody are prepared by methods known in the art, such as described in Epstein et al., *Proc. Natl. Acad. Sci. USA* 82:3688 (1985); Hwang et al., *Proc. Natl Acad. Sci. USA* 77:4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.* 257: 28&288 (1982) via a disulfide interchange reaction. A chemotherapeutic agent (such as doxorubicin) may be optionally contained within the liposome. See Gabizon et al., *J. National Cancer Inst.* 81(19):1484 (1989).

ix. Uses for Anti-TCCR Antibodies

The anti-TCCR antibodies of the present invention have various utilities. For example, anti-TCCR antibodies may be used in diagnostic assays for TCCR, e.g., detecting its expression in specific cells, tissues, or serum. Various diagnostic assay techniques known in the art may be used, such as competitive binding assays, direct or indirect sandwich assays and immunoprecipitation assays conducted in either heterogeneous or homogenous phases [Zola, *Monoclonal Antibodies: A Manual of Techniques*, CRC Press, Inc. (1987) pp. 147-158]. The antibodies used in the diagnostic assays can be labeled with a detectable moiety. The detectable moiety should be capable of producing, either directly or indirectly, a detectable signal. For example, the detectable moiety may be a radioisotope, such as $^3$H, $^{14}$C, $^{32}$P, $^{35}$S or $^{125}$I, a fluorescent or chemiluminescent compound, such as fluorescein isothiocynate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature* 144: 945 (1962); David et al., *Biochemistry* 13: 1014 (1974); Pain et al., *J. Immunol. Meth.* 40: 219 (1981) and Nygren, *J. Histochem. Cytochem.* 30: 407 (1982).

Anti-TCCR antibodies also are useful for the affinity purification of TCCR from recombinant cell culture or natural sources. In this process, the antibodies against TCCR are immobilized on a suitable support, such a Sephadex resin or filter paper, using methods well known in the art. The immobilized antibody then is contacted with a sample containing the TCCR to be purified, and thereafter the support is washed with a suitable solvent that will remove substantially all the material in the sample except the TCCR, which is bound to the immobilized antibody. Finally, the support is washed with another suitable solvent that will release the TCCR from the antibody.

10. Pharmaceutical Compositions

The active molecules of the invention, polypeptides and antibodies, as well as other molecules identified by the screening assays disclosed above, can be administered for the treatment of immune related diseases, in the form of pharmaceutical compositions.

In order to target the intracellular portion of TCCR or to target TCCR while it is still intracellular, internalizing antibodies may be used. Additionally, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA* 90: 7889-7893 (1993).

Therapeutic formulations of the active molecule, preferably a polypeptide or antibody of the invention, are prepared for storage by mixing the active molecule having the desired degree of purity with optional pharmaceutically acceptable carriers, excipients or stabilizers (*Remington's Pharmaceutical Sciences* 16th edition, Osol, A. Ed. [1980]), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or nonionic surfactants such as TWEEN™, PLURONICS™ or polyethylene glycol (PEG).

Compounds identified by the screening assays of the present invention can be formulated in an analogous manner, using standard techniques well known in the art.

The formulation herein may also contain more than one active compound as necessary for the particular indication being treated, preferably those with complementary activities that do not adversely affect each other. Alternatively, or in addition, the composition may comprise a cytotoxic agent, cytokine or growth inhibitory agent. Such molecules are suitably present in combination in amounts that are effective for the purpose intended.

The active molecules may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S-S bond formation through thio-disulfide interchange, stabilization may be achieved by modifying sulfhydryl residues, lyophilizing from acidic solutions, controlling moisture content, using appropriate additives, and developing specific polymer matrix compositions.

11. Methods of Treatment

It is contemplated that the polypeptides, antibodies and other active compounds of the present invention may be used to treat various immune related diseases and conditions, such as T cell mediated diseases, including those characterized by infiltration of inflammatory cells into a tissue, stimulation of T-cell proliferation, inhibition of T-cell proliferation, increased or decreased vascular permeability or the inhibition thereof.

Exemplary conditions or disorders to be treated with the polypeptides, antibodies and other compounds of the invention, include, but are not limited to systemic lupus erythematosis, rheumatoid arthritis, juvenile chronic arthritis, osteoarthritis, spondyloarthropathies, systemic sclerosis (scleroderma), idiopathic inflammatory myopathies (dermatomyositis, polymyositis), Sjögren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Háshimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barré syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory bowel disease (ulcerative colitis: Crohn's disease), gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, transplantation associated diseases including graft rejection and graft-versus-host-disease.

In systemic lupus erythematosus, the central mediator of disease is the production of auto-reactive antibodies to self proteins/tissues and the subsequent generation of immune-mediated inflammation, antibodies either directly or indirectly mediate tissue injury. Though T lymphocytes have not been shown to be directly involved in tissue damage, T lymphocytes are required for the development of auto-reactive antibodies. The genesis of the disease is thus T lymphocyte dependent. Multiple organs and systems are affected clinically including kidney, lung, musculoskeletal system, mucocutaneous, eye, central nervous system, cardiovascular system, gastrointestinal tract, bone marrow and blood.

Rheumatoid arthritis (RA) is a chronic systemic autoimmune inflammatory disease that mainly involves the synovial membrane of multiple joints with resultant injury to the articular cartilage. The pathogenesis is T lymphocyte dependent and is associated with the production of rheumatoid factors, auto-antibodies directed against self IgG, with the resultant formation of immune complexes that attain high levels in joint fluid and blood. These complexes in the joint may induce the marked infiltrate of lymphocytes and monocytes into the synovium and subsequent marked synovial changes; the joint space/fluid if infiltrated by similar cells with the addition of numerous neutrophils. Tissues affected are primarily the joints, often in symmetrical pattern. However, extra-articular disease also occurs in two major forms. One form is the development of extra-articular lesions with ongoing progressive joint disease and typical lesions of pulmonary fibrosis, vasculitis, and cutaneous ulcers. The second form of extra-articular disease is the so called Felty's syndrome which occurs late in the RA disease course, sometimes after joint disease has become quiescent, and involves the presence of neutropenia, thrombocytopenia and splenomegaly. This can be accompanied by vasculitis in multiple organs with formations of infarcts, skin ulcers and gangrene. Patients often also develop rheumatoid nodules in the subcutis tissue overlying affected joints; the nodules late stage have necrotic centers surrounded by a mixed inflammatory cell infiltrate. Other manifestations which can occur in RA include: pericarditis, pleuritis, coronary arteritis, intestinal pneumonitis with pulmonary fibrosis, keratoconjunctivitis sicca, and rheumatoid nodules.

Juvenile chronic arthritis is a chronic idiopathic inflammatory disease which begins often at less than 16 years of age. Its phenotype has some similarities to RA; some patients which are rheumatoid factor positive are classified as juvenile rheumatoid arthritis. The disease is sub-classified into three major categories: pauciarticular, polyarticular, and systemic. The arthritis can be severe and is typically destructive and leads to joint ankylosis and retarded growth. Other manifestations can include chronic anterior uveitis and systemic amyloidosis.

Spondyloarthropathies are a group of disorders with some common clinical features and the common association with the expression of HLA-B27 gene product. The disorders include: ankylosing spondylitis, Reiter's syndrome (reactive arthritis), arthritis associated with inflammatory bowel disease, spondylitis associated with psoriasis, juvenile onset spondyloarthropathy and undifferentiated spondyloarthropathy. Distinguishing features include sacroileitis with or without spondylitis; inflammatory asymmetric arthritis; association with HLA-B27 (a serologically defined allele of the HLA-B locus of class I MHC); ocular inflammation, and absence of autoantibodies associated with other rheumatoid disease. The cell most implicated as key to induction of the disease is the CD8+ T lymphocyte, a cell which targets antigen presented by class I MHC molecules. CD8+ T cells may react against the class I MHC allele HLA-B27 as if it were a foreign peptide expressed by MHC class I molecules. It has been hypothesized that an epitope of HLA-B27 may mimic a bacterial or other microbial antigenic epitope and thus induce a CD8+ T cells response.

Systemic sclerosis (scleroderma) has an unknown etiology. A hallmark of the disease is induration of the skin; likely this is induced by an active inflammatory process. Scleroderma can be localized or systemic; vascular lesions are common and endothelial cell injury in the microvasculature is an early and important event in the development of systemic sclerosis; the vascular injury may be immune mediated. An immunologic basis is implied by the presence of mononuclear cell infiltrates in the cutaneous lesions and the presence of antinuclear antibodies in many patients. ICAM-1 is often upregulated on the cell surface of fibroblasts in skin lesions suggesting that T cell interaction with these cells may have a role in the pathogenesis of the disease. Other organs involved include: the gastrointestinal tract: smooth muscle atrophy and fibrosis resulting in abnormal peristalsis/motility; kidney: concentric subendothelial intimal proliferation affecting small arcuate and interlobular arteries with resultant reduced renal cortical blood flow, results in proteinuria, azotemia and hypertension; skeletal muscle: atrophy, interstitial fibrosis; inflammation; lung: interstitial pneumonitis and interstitial fibrosis; and heart: contraction band necrosis, scarring/fibrosis.

Idiopathic inflammatory myopathies including dermatomyositis, polymyositis and others are disorders of chronic muscle inflammation of unknown etiology resulting in muscle weakness. Muscle injury/inflammation is often symmetric and progressive. Autoantibodies are associated with most forms. These myositis-specific autoantibodies are directed against and inhibit the function of components, proteins and RNA's, involved in protein synthesis.

Sjögren's syndrome is due to immune-mediated inflammation and subsequent functional destruction of the tear glands and salivary glands. The disease can be associated with or accompanied by inflammatory connective tissue diseases. The disease is associated with autoantibody production against Ro and La antigens, both of which are small RNA-protein complexes. Lesions result in keratoconjunctivitis sicca, xerostomia, with other manifestations or associations including bilary cirrhosis, peripheral or sensory neuropathy, and palpable purpura.

Systemic vasculitis are diseases in which the primary lesion is inflammation and subsequent damage to blood vessels which results in ischemia/necrosis/degeneration to tissues supplied by the affected vessels and eventual end-organ dysfunction in some cases. Vasculitides can also occur as a secondary lesion or sequelae to other immune-inflammatory mediated diseases such as rheumatoid arthritis, systemic sclerosis, etc., particularly in diseases also associated with the formation of immune complexes. Diseases in the primary systemic vasculitis group include: systemic necrotizing vasculitis: polyarteritis nodosa, allergic angiitis and granulomatosis, polyangiitis; Wegener's granulomatosis; lymphomatoid granulomatosis; and giant cell arteritis. Miscellaneous vasculitides include: mucocutaneous lymph node syndrome (MLNS or Kawasaki's disease), isolated CNS vasculitis, Behet's disease, thromboangiitis obliterans (Buerger's disease) and cutaneous necrotizing venulitis. The pathogenic mechanism of most of the types of vasculitis listed is believed to be primarily due to the deposition of immunoglobulin complexes in the vessel wall and subsequent induction of an inflammatory response either via ADCC, complement activation, or both.

Sarcoidosis is a condition of unknown etiology which is characterized by the presence of epitheloid granulomas in nearly any tissue in the body; involvement of the lung is most common. The pathogenesis involves the persistence of activated macrophages and lymphoid cells at sites of the disease with subsequent chronic sequelae resultant from the release of locally and systemically active products released by these cell types.

Autoimmune hemolytic anemia including autoimmune hemolytic anemia, immune pancytopenia, and paroxysmal nocturnal hemoglobinuria is a result of production of antibodies that react with antigens expressed on the surface of red blood cells (and in some cases other blood cells including platelets as well) and is a reflection of the removal of those antibody coated cells via complement mediated lysis and/or ADCC/Fc-receptor-mediated mechanisms.

In autoimmune thrombocytopenia including thrombocytopenic purpura, and immune-mediated thrombocytopenia in other clinical settings, platelet destruction/removal occurs as a result of either antibody or complement attaching to platelets and subsequent removal by complement lysis, ADCC or FC-receptor mediated mechanisms.

Thyroiditis including Grave's disease, Hashimoto's thyroiditis, juvenile lymphocytic thyroiditis, and atrophic thyroiditis, are the result of an autoimmune response against thyroid antigens with production of antibodies that react with proteins present in and often specific for the thyroid gland. Experimental models exist including spontaneous models: rats (BUF and BB rats) and chickens (obese chicken strain); inducible models: immunization of animals with either thyroglobulin, thyroid microsomal antigen (thyroid peroxidase).

Type I diabetes mellitus or insulin-dependent diabetes is the autoimmune destruction of pancreatic islet β cells; this destruction is mediated by auto-antibodies and auto-reactive T cells. Antibodies to insulin or the insulin receptor can also produce the phenotype of insulin-non-responsiveness.

Immune mediated renal diseases, including glomerulonephritis and tubulointerstitial nephritis, are the result of antibody or T lymphocyte mediated injury to renal tissue either directly as a result of the production of autoreactive antibodies or T cells against renal antigens or indirectly as a result of the deposition of antibodies and/or immune complexes in the kidney that are reactive against other, non-renal antigens. Thus other immune-mediated diseases that result in the formation of immune-complexes can also induce immune mediated renal disease as an indirect sequelae. Both direct and indirect immune mechanisms result in inflammatory response that produces/induces lesion development in renal tissues with resultant organ function impairment and in some cases progression to renal failure. Both humoral and cellular immune mechanisms can be involved in the pathogenesis of lesions.

Demyelinating diseases of the central and peripheral nervous systems, including multiple sclerosis; idiopathic demyelinating polyneuropathy or Guillain-Barré syndrome; and Chronic Inflammatory Demyelinating Polyneuropathy, are believed to have an autoimmune basis and result in nerve demyelination as a result of damage caused to oligodendrocytes or to myelin directly. In MS there is evidence to suggest that disease induction and progression is dependent on T lymphocytes. Multiple Sclerosis is a demyelinating disease that is T lymphocyte-dependent and has either are lapsing-remitting course or a chronic progressive course. The etiology is unknown; however, viral infections, genetic predisposition, environment, and autoimmunity all contribute. Lesions contain infiltrates of predominantly T lymphocyte mediated, microglial cells and infiltrating macrophages; CD4+ T lymphocytes are the predominant cell type at lesions. The mechanism of oligodendrocyte cell death and subsequent demyelination is not known but is likely T lymphocyte driven.

Inflammatory and Fibrotic Lung Disease, including Eosinophilic Pneumonias; Idiopathic Pulmonary Fibrosis, and Hypersensitivity Pneumonitis may involve a disregulated immune-inflammatory response. Inhibition of that response would be of therapeutic benefit.

Autoimmune or Immune-mediated Skin Disease including Bullous Skin Diseases, Erythema Multiforme, and Contact Dermatitis are mediated by auto-antibodies, the genesis of which is T lymphocyte-dependent.

Psoriasis is a T lymphocyte-mediated inflammatory disease. Lesions contain infiltrates of T lymphocytes, macrophages and antigen processing cells, and some neutrophils.

Allergic diseases, including asthma; allergic rhinitis; atopic dermatitis; food hypersensitivity; and urticaria are T lymphocyte dependent. These diseases are predominantly mediated by T lymphocyte induced inflammation, IgE mediated-inflammation or a combination of both.

Transplantation associated diseases, including Graft rejection and Graft-Versus-Host-Disease (GVHD) are T lymphocyte-dependent; inhibition of T lymphocyte function is ameliorative.

Other diseases in which intervention of the immune and/or inflammatory response have benefit are infectious disease including but not limited to viral infection (including but not limited to AIDS, hepatitis A, B, C, D, E and herpes) bacterial infection, fungal infections, and protozoal and parasitic infections (molecules (or derivatives/agonists) which stimulate the MLR can be utilized therapeutically to enhance the immune response to infectious agents), diseases of immunodeficiency (molecules/derivatives/agonists) which stimulate the MLR can be utilized therapeutically to enhance the immune response for conditions of inherited, acquired, infectious induced (as in HIV infection), or iatrogenic (i.e. as from chemotherapy) immunodeficiency, and neoplasia.

It has been demonstrated that some human cancer patients develop an antibody and/or T lymphocyte response to antigens on neoplastic cells. It has also been shown in animal models of neoplasia that enhancement of the immune response can result in rejection or regression of that particular neoplasm. Molecules that enhance the T lymphocyte response in the MLR have utility in vivo in enhancing the immune response against neoplasia. Molecules which enhance the T lymphocyte proliferative response in the MLR (or small molecule agonists or antibodies that affect the same receptor in an agonistic fashion) can be used therapeutically to treat cancer. Molecules that inhibit the lymphocyte response in the MLR also function in vivo during neoplasia to suppress the immune response to a neoplasm; such molecules can either be expressed by the neoplastic cells themselves or their expression can be induced by the neoplasm in other cells. Antagonism of such inhibitory molecules (either with antibody, small molecule antagonists or other means) enhances immune-mediated tumor rejection.

Additionally, inhibition of molecules with proinflammatory properties may have therapeutic benefit in reperfusion injury; stroke; myocardial infarction; atherosclerosis; acute lung injury; hemorrhagic shock; burn; sepsis/septic shock; acute tubular necrosis; endometriosis; degenerative joint disease and pancreatis.

The compounds of the present invention, e.g. polypeptides or antibodies, are administered to a mammal, preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation (intranasal, intrapulmonary) routes. Intravenous or inhaled administration of polypeptides and antibodies is preferred.

In immunoadjuvant therapy, other therapeutic regimens, such administration of an anti-cancer agent, may be combined with the administration of the proteins, antibodies or compounds of the instant invention. For example, the patient to be treated with an immunoadjuvant of the invention may also receive an anti-cancer agent (chemotherapeutic agent) or radiation therapy. Preparation and dosing schedules for such chemotherapeutic agents may be used according to manufacturers' instructions or as determined empirically by the skilled practitioner. Preparation and dosing schedules for such chemotherapy are also described in *Chemotherapy Service* Ed., M. C. Perry, Williams & Wilkins, Baltimore, Md. (1992). The chemotherapeutic agent may precede, or follow administration of the immunoadjuvant or may be given simultaneously therewith. Additionally, an anti-oestrogen compound such as tamoxifen or an anti-progesterone such as onapristone (see, EP 616812) may be given in dosages known for such molecules.

It may be desirable to also administer antibodies against other immune disease associated or tumor associated antigens, such as antibodies which bind to CD20, CD11a, CD18, ErbB2, EGFR, ErbB3, ErbB4, or vascular endothelial factor (VEGF). Alternatively, or in addition, two or more antibodies binding the same or two or more different antigens disclosed herein may be coadministered to the patient. Sometimes, it may be beneficial to also administer one or more cytokines to the patient. In one embodiment, the polypeptides of the invention are coadministered with a growth inhibitory agent. For example, the growth inhibitory agent may be administered first, followed by a polypeptide of the invention. However, simultaneous administration or administration first is also contemplated. Suitable dosages for the growth inhibitory agent are those presently used and may be lowered due to the combined action (synergy) of the growth inhibitory agent and the polypeptide of the invention.

For the treatment or reduction in the severity of immune related disease, the appropriate dosage of an a compound of the invention will depend on the type of disease to be treated, as defined above, the severity and course of the disease, whether the agent is administered for preventive or therapeutic purposes, previous therapy, the patient's clinical history and response to the compound, and the discretion of the attending physician. The compound is suitably administered to the patient at one time or over a series of treatments.

For example, depending on the type and severity of the disease, about 1 µg/kg to 15 mg/kg (e.g. 0.1-20 mg/kg) of polypeptide or antibody is an initial candidate dosage for administration to the patient, whether, for example, by one or more separate administrations, or by continuous infusion. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

12. Articles of Manufacture

In another embodiment of the invention, an article of manufacture containing materials useful for the diagnosis or treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for diagnosing or treating the condition and may have a sterile access port (for example the container may be an intravenous solution bag or a vial having a stopper pierceable by a hypodermic injection needle). The active agent in the composition is usually a polypeptide or an antibody of the invention. The label on, or associated with, the container indicates that the composition is used for diagnosing or treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

13. Diagnosis and Prognosis of Immune Related Disease

Cell surface proteins, such as proteins which are overexpressed in certain immune related diseases, are excellent targets for drug candidates or disease treatment. The same proteins along with secreted proteins encoded by the genes amplified in immune related disease states find additional use in the diagnosis and prognosis of these diseases. For example, antibodies directed against the protein products of genes amplified in multiple sclerosis, rheumatoid arthritis, or another immune related disease, can be used as diagnostics or prognostics.

For example, antibodies, including antibody fragments, can be used to qualitatively or quantitatively detect the expression of proteins encoded by amplified or overexpressed genes ("marker gene products"). The antibody preferably is equipped with a detectable, e.g. fluorescent label, and binding can be monitored by light microscopy, flow cytometry, fluorimetry, or other techniques known in the art. These techniques are particularly suitable, if the overexpressed gene encodes a cell surface protein Such binding assays are performed essentially as described above.

In situ detection of antibody binding to the marker gene products can be performed, for example, by immunofluorescence or immunoelectron microscopy. For this purpose, a histological specimen is removed from the patient, and a labeled antibody is applied to it, preferably by overlaying the antibody on a biological sample. This procedure also allows for determining the distribution of the marker gene product in the tissue examined. It will be apparent for those skilled in the art that a wide variety of histological methods are readily available for in situ detection.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va. Unless otherwise noted, the present invention uses standard procedures of recombinant DNA technology, such as those described hereinabove and in the following textbooks: Sambrook et al., *Molecular Cloning: A Laboratory Manual*, Cold Spring Harbor Press N.Y., 1989; Ausubel et al., *Current Protocols in Molecular Biology*, Green Publishing Associates and Wiley Interscience, N.Y., 1989; Innis et al., *PCR Protocols: A Guide to Methods and Applications*, Academic Press, inc., N.Y., 1990; Harlow et al., Antibodies: A Laboratory Manual, Cold Spring Harbor Press, Cold Spring Harbor, 1988; Gait, M. J., *Oligonucleotide Synthesis*, IRL Press, Oxford, 1984; R. I. Freshney, *Animal Cell Culture*, 1987; Coligan et al., *Current Protocols in Immunology*, 1991.

Example 1

Isolation and Cloning of TCCR

Cytokine receptors and/or receptor characterized by a WS(G)XWS domain were used to search public EST databases and resulted in the isolation of hTCCR (SEQ ID NO:1) and mTCCR (mTCCR).

Alternatively, the murine TCCR depicted in FIG. 4 (SEQ ID NO:2) has been published in WO97/44455 filed on 23 May 1996 as well as in GenBank as accession number 7710109. The prior art molecule is also described in Sprecher et al., *Biochem. Biophys, Res. Commun.* 246(1): 82-90 (1998). In FIG. 4 (SEQ ID NO:2), a signal peptide has been identified from amino acid residues 1 to about 24, the transmembrane domain from about amino acid residues 514 to about 532, N-glycosylation sites at about residues, 46-49, 296-299, 305-308, 360-361, 368-371 and 461-464, casein kinase II phosphorylation sites at about residues 10-13, 93-96, 130-133, 172-175, 184-187, 235-238, 271-274, 272-275, 323-326, 606-609 and 615-618, a tyrosine kinase phosphorylation site at about residues 202-209, N-myristoylation sites at about residues 43-48, 102-107, 295-300, 321-326, 330-335, 367-342, 393-398, 525-530 and 527-532, an amidation site at about residues 240-243, a prokaryotic membrane lipoprotein lipid attachment at about residues 516-526 and a growth factor and cytokine receptor family signature 1 at about residues 36-49. Region of significant homology exist with: (1) human erythropoietin at about residues 14-51 and (2) murine interleukin-5 receptor at residues 211-219.

A polypeptide having high homology to the human TCCR depicted in FIG. 3 (SEQ ID NO:1) has been published in WO 97/44455 filed on 23 May 1996 which is also available from GenBank as accession number 4759327. The prior art molecule is also described in Sprecher et al., *Biochem. Biophys, Res. Commun.* 246(1): 82-90 (1998). In FIG. 3 (SEQ ID NO:1), a signal peptide has been identified from amino acid residues 1 to about 32, the transmembrane domain from about amino acid residues 517 to about 538, N-glycosylation sites at about residues 51-54, 76-79, 302-305, 311-314, 374-377, 382-385, 467-470, 563-566, N-myristoylation sites at about residues 107-112, 240-245, 244-249, 281-286, 292-297, 373-378, 400-405, 459-464, 470-475, 531-536 and 533-538, a prokaryotic membrane lipoprotein lipid attachment site at about residues 522-532 and a growth factor and cytokine receptor family signature 1 at about residues 41-54. There is also a region of significant homology with the second subunit of the receptor for human granulocyte-macrophage colony-stimulating factor (GM-CSF) at residues 183-191.

A comparison of the human TCCR (SEQ ID NO:1) and murine TCCR (SEQ ID NO:2) sequences is shown in FIG. 5. The comparison reveals about 62% sequence identity between the human and the murine sequences.

Example 2

TCCR "Knockout" Mice

1. Preparation of the Targeting Vector

The term "targeting vector" is a term of art referring to a nucleic acid sequence that is constructed for gene ablation.

FIG. 9A describes the targeting vector used for the TCCR molecule isolated in this example. Specifically, the targeting vector was constructed using a 2.4 kb XhoI-HindIII fragment containing the first two exons and a 6.0 kb Eco RI-Bam HI fragment containing exons 9 through 14. The specific TCCR gene isolated contains 14 exons and 13 introns. In this targeting vector, the pGK-neo gene conferring gentamycin resistance has been used to replace exons 3-8, leaving exons 1 and 2 intact. The herpes simplex virus thymidine kinase (HSV-TK) coding region has been placed 5' of exon one, allowing for selection with gancyclovir. Such drug selectable makers, such as gancyclovir permit for selection of stable transfected cell lines containing the targeting vector and further allow for polymerase chain reaction (PCR) primers to be made which will amplify a fragment of nucleic acid unique to the targeting construct that will distinguish it from the endogenous gene. This construct was inserted into the vector pBluescript (Stratagene, La Jolla, Calif.) and transformed into DH10B bacteria. Single colonies were harvested and used to prepare larger quantities of targeting vector.

2. Preparation of TCCR-/- Stem Cells

The targeting vector was linearized by digestion with the restriction endonuclease NotI and transfected into embryonic stem (ES) cells. ES cells are chosen for their ability to integrate into the germ line of developing embryos so as to transmit the targeting vector to their progeny. The preferred ES line of choice is the ESGS line but the D3 line (ATCC CRL-1934) may also be used. Electroporation is done by using 2-5 million ES cells resuspended in 0.8 ml PBS. The linearized targeting vector (20 µg) is added to the cells and this is placed in a sterile electroporation cuvette (0.4 cm Bio-Rad, Hercules, Calif.). Electroporation is performed using the Bio-Rad electroporation apparatus set at 500 µF, 240 volts. The contents of the cuvette are transferred into 410 ml of ES media. ES media is composed of: High glucose DMEM (Gibco 11960-010), 10% FBS (ES cell tested Gibco 16141-061) and 1000 units/ml ESGRO murine LIF (Gibco 13275-0290). These cells are then aliquoted into 20 96 well dishes. After transfection of the targeting vector the ES cells are selected for by using a lethal concentration of previously mentioned drugs. In the instance of G418, 400 µg/ml is used. Only those ES cells carrying the targeting vector will have the antibiotic resistance markers necessary for survival. The selected ES cell colonies are then screened for correct integration of the vector via southern blotting (FIG. 10A), PCR (FIG. 10B), lack of endogenous target gene mRNA expression (FIG. 10C). ES clones that pass the above criteria are then used for microinjection into embryos.

3. Injection and Screening of TCCR-/- Mice

Selected and screened ES cell colonies from the previous step are transferred into a developing embryo by any suitable technique in art, preferably by microinjection. Suitable microinjection techniques are described in Hogan et al., *Manipulating the mouse embryo: A Laboratory Manual*, Cold Spring Harbor Laboratory Press, Cold Spring Harbor, N.Y. 1986. While any embryo may be used provided that it can be later identified, preferably the embryos selected for microinjection are male and have a coat color that is opposite of the coat color encoded by the genes of the ES cell containing the targeting vector. For example, ES cells from an animal with white fur would be injected into an embryo that will develop brown/black fur. In this manner successfully microinjected embryos can be selected as matured adults on the basis of a mosaic coat color. The resulting mosaic animals (founders) are TCCR-/+ and are then backcrossed (mated with other TCCR-/+progeny) to create TCCR-/- mice. To confirm the TCCR-/- genotype, DNA is extracted from tail clippings which is effected by incubating tail tissue at 60° C. overnight in 0.5 ml of lysis buffer. The lysis buffer consists of 0.5% SDS, 100 mM NaCl, 50 mM Tric-HCL (pH 8.0), 7.5 mM EDTA (pH 8.0) and 1 mg/ml proteinase K (Boehringer-Mannheim). After overnight incubation, an aliquots of 75 µl of 8M potassium acetate, 600 ml of $CHCl_3$ are mixed in the entire reaction is centrifuged for 10 minutes at room temperature. The aqueous layer is removed and placed in a separate eppendorf tube, to which is added 600 ml of 100% ethanol and the DNA is precipitated by centrifugation for 5 minutes. The DNA pellet is washed with 70% ethanol and allowed to air dry. After removal of residual ethanol the DNA pellet is resuspended in 150-200 µl of water. This DNA can then be used for Southern blotting and for PCR analysis. For the Southern blot, the neo gene may be used as a probe; for the PCR, the primers used for screening the ES cells are employed.

The results are reported in FIGS. 10A, 10B and 10C indicating a successful ablation of the TCCR gene. TCCR-deficient mice were viable, fertile and displayed no overt abnormalities. Detailed histological examination did not reveal any obvious defects. Flow cytometry analysis of cells obtained from thymus, spleen, lymph nodes and peyer's patches of multiple wild-type and knockout mice stained with antibodies to CD3, CD4, CD8, CD25, CD19, B220, CD40, NK1.1, DX5, F4/80, CD14, CD16, MHC II and CD45 did not reveal any gross differences between the two genotypes.

Example 3

Enhanced Allergic Airway Inflammation in TCCR-/- Mice

Asthma is a complex disease resulting from the interaction of a multitude of allergic and non-allergenic factors that elicit bronchial obstruction and inflammation. One of the key aspects of airway inflammation is the infiltration of the airway wall by Th2 cells. Because the TCCR-/- mice produce herein have a greater Th2 response, they are a useful model to study allergic airway inflammation.

Animals: Twelve TCCR-/- mice and eleven wild type littermate (WT) randomly divided into the following four groups: Group 1—Non-sensitized TCCR-/-; Group 2—Non sensitized TCCR WT (n=4); Group 3—Sensitized TCCR-/- (n=8); and Group 4—sensitized TCCR WT (n=7).

Sensitization: 15 mice (male and female) were sensitized with 300 units/ml of dust mite antigen (Bayer Pharmaceutical) adsorbed to 1 mg/ml Alum given IP at day 0 in 0.1 ml volume. The non sensitized control mice (n=8) received 0.1 ml of 0.9% NaCl and 1 mg/ml Alum IP. Both groups of mice were boosted on day 7 with an IP injection of antigen (sensitized groups) or NaCl (non sensitized groups) as described above.

Inhalation Challenges: After sensitization and boost, four DMA inhalation challenges were administered starting on day 16. For aerosolization, the final concentration of dust mite in the nebulizer was 6000 units/ml after being diluted with Dulbecco's PBS and 0.1% of TWEEN®-20. All inhalation challenges were administered in a PLEXIGLAS® pie exposure chamber. DMA was aerosolized for 20 minutes using a PARI IS-2 nebulizer initially and then refilled with 1.5 ml, 10 minutes into the exposure. Total deposited dose in the lung was ~6.5 AU of DMA.

AHR (paralyzed): On day 24, approximately 18 hours after the last DMA aerosol challenge the mice were anesthetized with a mixture of pentobarbital (25 mg/kg) and urethane (1.8 g/kg) and catheterized with a 1 cm incision over the right jugular vein. The jugular vein was dissected free and a catheter (PE-10 connected to PE-50) was inserted and tied into place. Additionally, the mice were tracheotomized (1 cm neck incision, trachea dissected free and a cannula inserted and tied into place). The mice were then loaded into a PLEXIGLAS® flow plethysmograph for measurement of thoracic expansion and airway pressure. The mice were ventilated using 100% oxygen at a frequency of 170 bpm and Vt equal to 9 µl/gm. Breathing mechanics (lung resistance and dynamic compliance) were continuously monitored using a computerized (Buxco Electronics) data acquisition program. After baseline measurements, the mice received a one-time 10-second dose of the methacholine (MCH dose of 500 µg/kg) using 200 µg/ml MCH as the stock concentration.

Sacrifice: After completion of the airway reactivity measurement EDTA tubes were used to collect blood via the retro-orbital sinus to obtain serum. The abdomen was opened, the descending aorta severed and the diaphragm cut. After time elapsed for the animals to exsanguinate, bronchioalveolar lavage (BAL) was performed. The lungs were lavaged three times with the same bolus of sterile saline (30 µg/g mouse weight) through the previously inserted tracheal cannula. The bolus filled the lung to approximately 70% total lung capacity. The samples of BAL (return averaged 80%) were centrifuged at 1000×g and 40° C. for 10 minutes. The supernatants were decanted and immediately frozen at −80° C. The cell pellets were resuspended in 250 ml of PBS with 2% BSA (Sigman, St. Louis, Mo.), then enumerated using an automated counter (Baker Instruments, Allentown, Pa.), and recorded as total number of BAL cells/µl. The cell suspension was then adjusted to 200 cells/µl and 100 ml was centrifuged onto coated SUPERFROST PLUS™ microscope slides (Baxter Diagnostics, Deerfield, Ill.) at 800×g for 10 minutes using a cytospin (Shandon, Inc., Pittsburgh, Pa.). Slides were air dried, fixed for 1 minute in 100% methanol, and stained with DIFF-OUIK™ (Baxter Health Care, Miami, Fla.). At least 200 cells were evaluated per slide to obtain a differential leukocyte count.

After BAL, the right lung, spleen and trachea bronchial lymph nodes were removed and frozen in liquid nitrogen for mRNA analysis (and then placed on dry ice). Tail cuts were taken and frozen on dry ice for later genotyping. The remaining left lungs of the mice were removed to evaluate and compare the severity and character of pathologic changes in lungs between experimental groups. This was accomplished by initial fixing of the lung tissue in 10% neutral-buffered formalin, embedded in paraffin, and 3 µm sections were stained with hemotoxilin and eosin. Lung sections were taken along the primary bronchus and the entire section was evaluated blindly and scored based on the severity of the inflammation around the airways and blood vessels. The extent of airway epithelial cell hypertrophy using a scale from 0 (no inflammation and airway changes) to 4 (marked inflammation and airway changes).

IgE ELISA: For the total IgE sandwich ELISA, the BAL fluid or serum sample was used either undiluted or diluted 1:2 to 1:20 (BAL) and 1:25 to 1:200 (serum) in ELISA buffer. The capture antibody was rabbit anti-mouse IgE (2 µg/ml PBS) and plates were coated for 24-48 hours at 4 C. The standard was murine IgE (PharMingen, San Diego, Calif.) which was diluted serially 1:2, starting with 100 ng/ml concentration. The detection antibody, biotinylated FcεRI-IgG was used at a dilution of 1:2000 for 1-1.5 hours. HRP-SA and enzyme development steps were identical to those used for the cytokine assays.

The results demonstrate a significant increase in lymphocyte infiltration into the lung in the TCCR−/− mice than in the wild type (FIG. 11).

Example 4

Expression of TCCR in *E. coli*

This example illustrates preparation of an unglycosylated form of TCCR by recombinant expression in *E. coli*. The DNA sequence encoding TCCR is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli*; see Bolivar et al., *Gene*, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the TCCR coding region, lambda transcriptional terminator, and an argU gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized TCCR protein can then be purified using a metal chelating column under conditions that allow tight binding of the protein. TCCR may also be expressed in *E. coli* in a poly-His tagged form, using the following procedure. The DNA encoding TCCR is initially amplified using selected PCR primers. The primers contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an *E. coli* host based on strain 52 (W3110 fuhA(tonA) lon galE rpoHts(ht-pRts) clpP(lacIq). Transformants are first grown in LB containing 50 mg/ml carbenicillin at 30° C. with shaking until an O.D.600 of 3-5 is reached. Cultures are then diluted 50-100 fold into CRAP media (prepared by mixing 3.57 g $(NH_4)_2SO_4$, 0.71 g sodium citrate $2H_2O$, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20-30 hours at 30° C. with shaking. Samples are removed to verify expression by SDS-PAGE analysis, and the bulk culture is centrifuged to pellet the cells. Cell pellets are frozen until purification and refolding.

*E. coli* paste from 0.5 to 1 L fermentations (6-10 g pellets) is resuspended in 10 volumes (w/v) in 7 M guanidine, 20 mM Tris, pH 8 buffer. Solid sodium sulfite and sodium tetrathionate is added to make final concentrations of 0.1M and 0.02 M, respectively, and the solution is stirred overnight at 4° C. This step results in a denatured protein with all cysteine residues blocked by sulfitolization. The solution is centrifuged at 40,000 rpm in a Beckman Ultracentifuge for 30 min. The supernatant is diluted with 3-5 volumes of metal chelate column buffer (6 M guanidine, 20 mM Tris, pH 7.4) and filtered through 0.22 micron filters to clarify. Depending on condition, the clarified extract is loaded onto a 5 ml Qiagen Ni-NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein was pooled and stored at 4° C. Protein concentration is estimated by its absorbance at 280 nm using the calculated extinction coefficient based on its amino acid sequence.

The proteins are refolded by diluting sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes are chosen so that the final protein concentration is between 50 to 100 micrograms/ml. The refolding solution is stirred gently at 4 C for 12-36 hours. The refolding reaction is quenched by the addition of TFA to a final concentration of 0.4% (pH of approximately 3). Before further purification of the protein, the solution is filtered through a 0.22 micron filter and acetonitrile is added to 2-10% final concentration. The refolded protein is chromatographed on a Poros R1/H reversed phase column using a mobile buffer of 0.1% TFA with elution with a gradient of acetonitrile from 10 to 80%. Aliquots of fractions with A280 absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded TCCR proteins, respectively, are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

Example 5

Expression of TCCR in Mammalian Cells

This example illustrates preparation of a potentially glycosylated form of TCCR by recombinant expression in mammalian cells.

The vector, pRK5 (see EP 307,247, published Mar. 15, 1989), is employed as the expression vector. Optionally, the TCCR DNA is ligated into pRK5 with selected restriction enzymes to allow insertion of the TCCR DNA using ligation methods such as described in Sambrook et al., supra. The resulting vector is called, for example, pRK5-TCCR.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-TCCR DNA is mixed with about 1 μg DNA encoding the VA RNA gene [Thimmappaya et al., *Cell*, 31:543 (1982)] and dissolved in 500 mL of 1 mM Tris-HCl, 0.1 mM EDTA, 0.227 M $CaCl_2$. To this mixture is added, dropwise, 500 μL of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 uCi/ml $^{35}$S-cysteine and 200 μCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of TCCR polypeptide. The cultures containing transfected cells may undergo further incubation (in serum free medium) and the medium is tested in selected bioassays.

In an alternative technique, TCCR may be introduced into 293 cells transiently using the dextran sulfate method described by Somrparyrac et al., *Proc. Natl. Acad. Sci.*, 12:7575 (1981). 293 cells are grown to maximal density in a spinner flask and 700 μg pRK5-TCCR DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 μg/ml bovine insulin and 0.1 μg/ml bovine transferrin. After about four days, the conditioned media is centrifuged and filtered to remove cells and debris. The sample containing expressed TCCR can then be concentrated and purified by any selected method, such as dialysis and/or column chromatography.

In another embodiment, TCCR can be expressed in CHO cells. The pRK5-TCCR can be transfected into CHO cells using known reagents such as $CaPO_4$ or DEAE-dextran. As described above, the cell cultures can be incubated, and the medium replaced with culture medium (alone) or medium containing a radiolabel such as S-methionine. After determining the presence of TCCR, the culture medium may be replaced with serum free medium. Preferably, the cultures are incubated for about 6 days, and then the conditioned medium is harvested. The medium containing the expressed TCCR can then be concentrated and purified by any selected method.

Epitope-tagged TCCR may also be expressed in host CHO cells. The TCCR may be subcloned out of the pRK5 vector. The subclone insert can undergo PCR to fuse in frame with a selected epitope tag such as a poly-his tag into a Baculovirus expression vector. The poly-his tagged TCCR insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged TCCR can then be concentrated and purified by any selected method, such as by $Ni^{2+}$-chelate affinity chromatography.

TCCR may also be expressed in CHO and/or COS cells by a transient expression procedure or in CHO cells by another stable expression procedure.

Stable expression in CHO cells may be performed using the procedure outlined below. The proteins may be expressed, for example, either (I) as an IgG construct (immunoadhesin), in which the coding sequences for the soluble forms (e.g., extracellular domains) of the respective proteins are fused to an IgG constant region sequence containing the hinge CH2 domain and/or (2) a poly-His tagged form.

Following PCR amplification, the respective DNAs are subcloned in a CHO expression vector using standard techniques as described in Ausubel et al., *Current Protocols of Molecular Biology*, Unit 3.16, John Wiley and Sons (1997). CHO expression vectors are constructed to have compatible restriction sites 5' and 3' of the DNA of interest to allow the convenient shuttling of cDNAs. The vector used expression in CHO cells is as described in Lucas et al., *Nucl. Acids Res.* 24:9 (1774-1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available transfection reagents SUPERFECT® (Quiagen), DOSPER® or FUGENE® (Boehringer Mannheim). The cells are grown as described in Lucas et al., supra. Approximately $3\times10^{-7}$ cells are frozen in an ampule for further growth and production as described below.

The ampules containing the plasmid DNA are thawed by placement into water bath and mixed by vortexing. The contents are pipetted into a centrifuge tube containing 10 mLs of media and centrifuged at 1000 rpm for 5 minutes. The supernatant is aspirated and the cells are resuspended in 10 mL of selective media (0.2 μm filtered PS20 with 5% 0.2 μm diafiltered fetal bovine serum). The cells are then aliquoted into a 100 mL spinner containing 90 mL of selective media. After 1-2 days, the cells are transferred into a 250 mL spinner filled with 150 mL selective growth medium and incubated at 37° C. After another 2-3 days, 250 mL, 500 mL and 2000 mL spinners are seeded with $3\times10^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3 L production spinner is seeded at $1.2\times10^6$ cells/mL. On day 0, the cell number pH is determined. On day 1, the spinner is sampled and sparging with filtered air is commenced. On day 2, the spinner is sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion) taken. Throughout the production, the pH is adjusted as necessary to keep it at around 7.2. After 10 days, or until the viability dropped below 70%, the cell culture is harvested by centrifugation and filtering through a 0.22 μm filter. The filtrate was either stored at 4° C. or immediately loaded onto columns for purification.

For the poly-His tagged constructs, the proteins are purified using a Ni-NTA column (Qiagen). Before purification, imidazole is added to the conditioned media to a concentration of 5 mM. The conditioned media is pumped onto a 6 ml Ni-NTA column equilibrated in 20 mM Hepes, pH 7.4, buffer containing 0.3 M NaCl and 5 mM imidazole at a flow rate of 4-5 ml/min. at 4° C. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc-containing) constructs are purified from the conditioned media as follows. The conditioned medium is pumped onto a 5 ml Protein A column (Pharmacia) which had been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 µL of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

Example 6

Expression of TCCR in Yeast

The following method describes recombinant expression of TCCR in yeast.

First, yeast expression vectors are constructed for intracellular production or secretion of TCCR from the ADH2/GAPDH promoter. DNA encoding TCCR and the promoter is inserted into suitable restriction enzyme sites in the selected plasmid to direct intracellular expression of TCCR. For secretion, DNA encoding TCCR can be cloned into the selected plasmid, together with DNA encoding the ADH2/GAPDH promoter, a native TCCR signal peptide or other mammalian signal peptide, or, for example, a yeast alpha-factor or invertase secretory signal/leader sequence, and linker sequences (if needed) for expression of TCCR.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant TCCR can subsequently be isolated and purified by removing the yeast cells from the fermentation medium by centrifugation and then concentrating the medium using selected cartridge filters. The concentrate containing TCCR may further be purified using selected column chromatography resins.

Example 7

Expression of TCCR in Baculovirus-Infected Insect Cells

The following method describes recombinant expression of TCCR in Baculovirus-infected insect cells.

The sequence coding for TCCR is fused upstream of an epitope tag contained within a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the sequence encoding TCCR or the desired portion of the coding sequence of TCCR [such as the sequence encoding the extracellular domain of a transmembrane protein or the sequence encoding the mature protein if the protein is extracellular] is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BACULOGOLD™ virus DNA (Pharmingen) into Spodoptera frugiperda ("Sf9") cells (ATCC CRL 1711) using lipofectin (commercially available from GIBCO-BRL). After 4-5 days of incubation at 28° C., the released viruses are harvested and used for further amplifications. Viral infection and protein expression are performed as described by O'Reilley et al., Baculovirus expression vectors: A Laboratory Manual, Oxford: Oxford University Press (1994).

Expressed poly-his tagged TCCR can then be purified, for example, by $Ni^{2+}$-chelate affinity chromatography as follows. Extracts are prepared from recombinant virus-infected Sf9 cells as described by Rupert et al., Nature, 362: 175-179 (1993). Briefly, Sf9 cells are washed, resuspended in sonication buffer (25 mL Hepes, pH 7.9; 12.5 mM $MgCl_2$; 0.1 mM EDTA; 10% glycerol; 0.1% NP40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 µm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged TCCR are pooled and dialyzed against loading buffer.

Alternatively, purification of the IgG tagged (or Fc tagged) TCCR can be performed using known chromatography techniques, including for instance, Protein A or Protein G column chromatography.

Alternatively still, the TCCR molecules of the invention may be expressed using a modified baculovirus procedure employing Hi-5 cells. In this procedure, the DNA encoding the desired sequence was amplified with suitable systems, such as Pfu (Stratagene), or fused upstream (5'-of) an epitope tag contained within a baculovirus expression vector. Such epitope tags include poly-His tags and immunoglobulin tags (like Fc regions of IgG). A variety of plasmids may be employed, including plasmids derived from commercially available plasmids such as pIE1-1 (Novagen). The pIE1-1 and pIE1-2 vectors are designed for constitutive expression of recombinant proteins from the baculovirus ie1 promoter in stably transformed insect cells. The plasmids differ only in the orientation of the multiple cloning sites and contain all promoter sequences known to be important for ie1-mediated gene expression in uninfected insect cells as well as the hr5 enhancer element. pIE1-1 and pIE1-2 include the ie1 translation initiation site and can be used to produce fusion proteins. Briefly, the desired sequence or the desired portion of the sequence (such as the sequence encoding the extracellular domain of the transmembrane protein) is amplified by PCR with primers complementary to the 5' and 3' regions. The 5' primer may incorporate flanking (selected) restriction enzyme sites. The product was then digested with those selected restriction enzymes and subcloned into the expression vector. For example, derivatives of pIE1-1 can include the Fc region of human IgG (pb.PH.IgG) or an 8 histidine (pb.PH.His) tag downstream (3'-of) the desired sequence. Preferably, the vector construct is sequenced for confirmation.

Hi5 cells are grown to a confluency of 50% under the conditions of 27° C., no $CO_2$, no pen/strep. For each 150 mm plate, 30 µg of pIE based vector containing the sequence was mixed with 1 ml EX-CELL™ medium (Media: EX-CELL™ 401+1/100 L-Glu JRH Biosciences #14401-78P (note: this media is light sensitive)). Separately, 100 µl of CELLFECTIN™ (CELLFECTIN™, Gibco BRL +10362-010, pre-vortexed) is mixed with 1 ml of EX-CELL™ medium. The two solutions are combined and incubated at room temperature for 15 minutes. 8 ml of EX-CELL™ media is added to the 2 ml of DNA/CELLFECTIN™ mix and this is layered on Hi5 cells that have been washed once with EX-CELL™ media. The plate is then incubated in darkness for 1 hour at room temperature. The DNA/CELLFECTIN™ mix is then aspirated, and the cells are washed once with EX-CELL™ to remove excess CELLFECTIN™. 30 ml of fresh EX-CELL™ media is added and the cells are incubated for 3 days at 28° C. The supernatant is harvested and the expression of the sequence in the baculovirus expression vector is determined by batch binding of 1 ml of supernatant to 25 ml of Ni-NTA beads (QIAGEN) for histidine tagged proteins of Protein-A SEPHAROSE™CL-4B beads (Pharmacia) for IgG tagged proteins followed by SDS-PAGE analysis comparing to a known concentration of protein standard by Coomassie blue staining.

The conditioned media from the transfected cells (0.5 to 3 L) was harvested by centrifugation to remove the cells and filtered through 0.22 micron filters. For the poly-His tagged constructs, the protein comprising the sequence is purified using a Ni-NTA column (Qiagen). Before purification, imidazole at a flow rate of 4-5 ml/min. at 48° C. After loading, the column is washed with additional equilibrium buffer and the protein eluted with equilibrium buffer containing 0.25M imidazole. The highly purified protein was then subsequently desalted into a storage buffer containing 10 mM Hepes, 0.14 M NaCl and 4% mannitol, pH 6.8 with a 25 ml G25 Superfine (Pharmacia) column and stored at -80° C.

Immunoadhesion (Fc-containing) constructs may also be purified from the conditioned media as follows: The conditioned media is pumped onto a 5 ml Protein A column (Pharmacia) which had been previously equilibrated in 20 mM sodium phosphate buffer, pH 6.8. After loading, the column is washed extensively with equilibrium buffer before elution with 100 mM citric acid, pH 3.5. The eluted protein is immediately neutralized by collecting 1 ml fractions into tubes containing 275 µl of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

Example 8

Preparation of Antibodies that Bind TCCR

This example illustrates preparation of monoclonal antibodies which can specifically bind TCCR.

Techniques for producing the monoclonal antibodies are known in the art and are described, for instance, in Goding, supra. Immunogens that may be employed include purified TCCR, fusion proteins containing TCCR, and cells expressing recombinant TCCR on the cell surface. Selection of the immunogen can be made by the skilled artisan without undue experimentation.

Mice, such as Balb/c, are immunized with the TCCR immunogen emulsified in complete Freund's adjuvant and injected subcutaneously or intraperitoneally in an amount from 1-100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-TCCR antibodies.

After a suitable antibody titer has been detected, the animals "positive" for antibodies can be injected with a final intravenous injection of TCCR. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597.

The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells are screened in an ELISA for reactivity against TCCR. Determination of "positive" hybridoma cells secreting the desired monoclonal antibodies against TCCR is within the skill in the art.

The positive hybridoma cells can be injected intraperitoneally into syngeneic Balb/c mice to produce ascites containing the anti-TCCR monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 9

Purification of TCCR Polypeptides Using Specific Antibodies

Native or recombinant TCCR polypeptides may be purified by a variety of standard techniques in the art of protein purification. For example, pro-TCCR polypeptide, mature TCCR polypeptide, or pre-TCCR polypeptide can be purified by immunoaffinity chromatography using antibodies specific for the TCCR polypeptide of interest. In general, an immunoaffinity column is constructed by covalently coupling the anti-TCCR polypeptide antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared form mouse ascites fluid by ammonium sulfate precipitation or chromatography on immobilized Protein A. Partially purified immunoglobulin is covalently attached to a chromatographic resin such as CnBr-activated SEPHAROSE™ (Pharmacia LKB Biotechnology). The antibody is coupled to the resin, the resin is blocked, and the derivative resin is washed according to the manufacturer's instructions.

Such an immunoaffinity column is utilized in the purification of TCCR polypeptide by preparing a fraction from cells containing TCCR polypeptide in a soluble form. This preparation is derived by solubilization of the whole cell or of a subcellular fraction obtained via differential centrifugation by the addition of detergent or by other methods well known in the art. Alternatively, soluble TCCR polypeptide containing a signal sequence may be secreted in useful quantity into the medium in which the cells are grown.

A soluble TCCR polypeptide-containing preparation is passed over the immunoaffinity column, and the column is washed under conditions that allow the preferential absorbance of TCCR polypeptide (e.g., high ionic strength buffers in the presence of detergent). Then, the column is eluted under conditions that disrupt antibody/TCCR polypeptide binding (e.g., a low pH buffer such as approximately pH 2-3, or a high concentration of a chaotrope such as urea or thiocyanate ion), and TCCR polypeptide is collected.

Example 10

Drug Screening

Methods may be employed which are particularly useful for screening compounds by using TCCR polypeptides or binding fragments thereof in any of a variety of drug screening techniques. The TCCR polypeptide or fragment employed in such a test may either be free in solution, affixed to a solid support, borne on a cell surface, or located intracellularly. One method of drug screening utilizes eukaryotic or prokaryotic host cells which are stably transformed with recombinant nucleic acids expressing the TCCR polypeptide or fragment. Drugs are screened against such transformed cells in competitive binding assays. Such cells, either in viable or fixed form, can be used for standard binding assays. One may measure, for example the formation of complexes between TCCR polypeptide or a fragment thereof and the agent being tested. Alternatively, one can examine the diminution in complex formation between the TCCR polypeptide and its target cell or target receptors caused by the agent being tested.

Thus, the present invention provides methods of screening for drugs or any other agents which can affect a TCCR polypeptide-associated disease or disorder. These methods comprise contacting such an agent with a TCCR polypeptide or fragment thereof and assaying (i) for the presence of a complex between the agent and the TCCR polypeptide or fragment, or (ii) for the presence of a complex between the TCCR polypeptide or fragment and the cell, by methods well known in the art. In such competitive binding assays, the TCCR polypeptide or fragment is typically labeled. After suitable incubation, free TCCR polypeptide or fragment thereof is separated from that present in bound form, and the amount of free or uncomplexed label is a measure of the ability of the particular agent to bind to TCCR polypeptide or to interfere with the TCCR polypeptide/cell complex.

Another technique for drug screening provides high throughput screening for compounds having suitable binding affinity to a polypeptide and is described in detail in WO 84/03564, published on Sep. 13, 1984. Briefly, large numbers of different small peptide test compounds are synthesized on a solid substrate, such as plastic pins or some other surface. As applied to a TCCR polypeptide, the peptide test compounds are reacted with TCCR polypeptide and washed. Bound TCCR polypeptide is detected by methods well known in the art. Purified TCCR polypeptide can also be coated directly onto plates for use in the aforementioned drug screening techniques. In addition, non-neutralizing antibodies can be used to capture the peptide an immobilize it on the solid support.

This invention also contemplated the use of competitive drug screening assays in which neutralizing antibodies capable of binding TCCR binding polypeptide specifically compete with a test compound for binding to TCCR polypeptide or fragments thereof. In this manner, the antibodies can be used to detect the presence of any peptide which shares one or more antigenic determinants with TCCR polypeptide.

Example 11

Rational Drug Design

The goal of rational drug design is to produce structural analogs of biologically active polypeptide of interest (i.e., a TCCR polypeptide) or of small molecules with which they interact, e.g., agonists, antagonists, or inhibitors. Any of these examples can be used to fashion drugs which are more active or stable forms of the TCCR polypeptide or which enhance or interfere with the function of the TCCR polypeptide in vivo (c.f., Hodgson, *Bio/Technology* 9: 19-21 (1991)).

In one approach, the three-dimensional structure of the TCCR polypeptide, or of a TCCR polypeptide-inhibitor complex, is determined by x-ray crystallography, by computer modeling, or most typically, by a combination of these approaches. Both the shape and charges of the TCCR polypeptide must be ascertained to elucidate the structure and to determine active site(s) of the molecule. Less often, useful information regarding the structure of the TCCR polypeptide may be gained by modeling based on the structure of homologous proteins. In both cases, relevant structural information is used to design analogous TCCR polypeptide-like molecules or to identify efficient inhibitors. Useful examples of rational drug design may include molecules which have improved activity or stability as shown by Braxton and Wells, *Biochemistry* 31: 7796-7801 (1992) or which act as inhibitors, agonists, or antagonists of native peptides as shown by Athauda et al., *J. Biochem.* 113: 742-746 (1993).

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amounts of the TCCR polypeptide may be made available to perform such analytical studies as X-ray crystallography. In addition, knowledge of the TCCR polypeptide amino acid sequence provided herein will provide guidance to those employing computer modeling techniques in place of or in addition to x-ray crystallography.

Table 2(A-D) show hypothetical exemplifications for using the below described method to determine % amino acid sequence identity (Table 2(A-B)) and % nucleic acid sequence identity (Table 2(C-D)) using the ALIGN-2 sequence comparison computer program, wherein "PRO" represents the amino acid sequence of a hypothetical polypeptide of the invention of interest, "Comparison Protein" represents the amino acid sequence of a polypeptide against which the "PRO" polypeptide of interest is being compared, "PRO-DNA" represents a hypothetical "PRO"-encoding nucleic acid sequence of interest, "Comparison DNA" represents the nucleotide sequence of a nucleic acid molecule against which the "PRO-DNA" nucleic acid molecule of interest is being compared, "X, "Y" and "Z" each represent different hypothetical amino acid residues and "N", "L" and "V" each represent different hypothetical nucleotides.

Example 12

Role of TCCR in Generation of an Immune Response

T cell responses: For anti-KLH responses, mice were immunized with 100 μg KLH in saline, in a 1:1 emulsion with CFA, containing 1 mg/ml *Mycobacterium tuberculosis* strain H37Ra, (Difco Laboratories, Detroit, Mich.) in the hind footpads. After 9 days, the popliteal lymph nodes were removed and cell suspensions were prepared. The lymph node cells were cultured ($5 \times 10^5$ per well) in various concentration of KLH in DMEM medium supplemented with 5% FCS. Proliferation was measured by addition of 1 μCi of [$^3$H]-thymidine (ICN, Irvine, Calif.) for the last 18 h of a 5-day culture, and incorporation of radioactivity was assayed by liquid scintillation counting. Assays for cytokine production by T cells were conducted by culturing $5 \times 10^5$ draining lymph node cells either from KLH-primed wild type or TCCR-deficient mice in the presence of indicated amounts of the KLH in 96 well plates in final volume of 200 ml. After 96 hr of culture, 150 μl of culture supernatant was removed from each well and cytokine levels were determined by ELISA using antibodies from Pharmingen (San Diego, Calif.), in the recommended conditions.

In vitro induction of T cell differentiation: $CD4^+T$ cells from spleen and lymph nodes from wild type or TCCR-deficient littermates were purified with anti-CD4 magnetic beads (MACS). Purified T cells ($10^6$ cells/ml) were activated in the presence of irradiated (3000 rad) syngeneic wild-type or knockout APC ($10^6$/ml) and ConA (2.5 μg/ml, Boehringer, Mannheim, Germany), or by plating on plates coated with 5 μg/ml anti-CD3 and 1 μg/ml anti-CD28 antibodies. The culture medium was supplemented with IL-2 (20 U/ml), IL-12 (3.5 ng/ml, R&D Systems) and 500 ng/ml anti-HL-4 antibody (Pharmingen) for Th1 differentiation, and with IL-2 (20 U/ml), IL-4 ($10^3$ U/ml, R&D Systems) and 500 ng/ml of anti-IFN antibody (Pharmingen) for Th2 differentiation. After three days, cells were either lysed for RNA extraction, or were extensively washed, counted, and restimulated at $10^6$ cells/ml, either in the presence of ConA (2.5 μg/ml) or on plates coated with 5 μg/ml anti-CD3 antibody. After 24 hours, supernatants were harvested and analyzed for the presence of cytokines.

Total and OVA-specific immunoglobulin levels: Unimmunized mice at 12 weeks of age or older were bled and serum was analyzed for the presence of various isotypes of immunoglobulins by ELISA. For anti-OVA specific antibodies, 6 wk old wild type or TCCR-deficient mice were immunized with 100 μg of OVA in complete Freund's adjuvant (i.p.) and 21 day later challenged with 100 μg of OVA in incomplete Freund's adjuvant (i.p.). Seven days after challenge mice were bled and serum was analyzed for presence of OVA-specific antibodies.

Real time PCR analysis: Murine splenocytes were separated into T helper cells (CD4 positive, F4/80 negative, 97% pure), B cells (CD19 positive, 97% pure), natural killer cells (NK1.1 positive, 99% pure), and macrophages (F4/80 positive, >95% pure) by FACS, and into cytotoxic T cells (CD8 positive, 85% pure) by MACS. Total RNA was extracted with Qiagen RNeasy columns and digested with DNAse I to remove contaminating DNA. RNA was probed for TCCR using Taqman 18. All reactions were made in duplicates and normalized to rpl19, a ribosomal housekeeping gene. A no RT control reaction was included and showed that all samples were free of contaminating DNA. The sequence of all primers and probes is described in FIG. 19.

Wild type and TCCR-deficient mice were immunized with keyhole limpet hemocyanin (KLH), and draining lymph nodes harvested 9 days later were assessed for cytokine production after in vitro stimulation in vitro with KLH (FIGS. 16A and B). The ability of TCCR-deficient cells to produce IFN was significantly impaired when challenged with KLH, while the production of IL-4 was markedly enhanced. Production of IL-5 and antigen induced proliferation of TCCR-deficient in vivo primed lymph node cells were normal (FIGS. 16C and D). Normal levels of IFN production were measured upon LPS stimulation of TCCR-deficient mice indicating that there seemed to be no intrinsic defects in IFN production in these mice. These results indicate that TCCR-deficient mice are impaired in their ability to mount a Th1 response. The loss of Th1 response is accompanied by an enhanced Th2 response similar to what has been observed in mice deficient in Th1 cytokines such as IL-12 (Magram, J., et al., 1996, *Immunity*, 4:471-81; Wu, C., et al., 1997, *J Immunol.*, 159: 1658-65).

In addition to its role in regulating the cellular immune response, IFN is also involved in immunoglobulin (Ig) isotype regulation. In particular, IFN is known to enhance the production of IgG2a antibodies and, to a lesser extent, of IgG3 antibodies (Snapper, C. M., & Paul, W. E., 1987, *Science*, 236:944-7; Huang, S., et al., 1993, *Science*, 259:1742-5). Consistent with a diminished production of IFN by Th1 cells, TCCR-deficient mice had decreased total serum IgG2a concentrations while the levels of all other immunoglobulin isotypes were normal (FIG. 17A). Furthermore, upon in vivo challenge with ovalbumin (OVA), TCCR-deficient mice had severely reduced titers of OVA-specific IgG2a (~20% of controls; FIG. 17B).

Th1 response is crucial in the defense against intracellular pathogens such as Listeria monocytogenes (*L. monocytogenes*). To further establish the in vivo role of TCCR in the control of Th1 response, TCCR-deficient mice and control littermates were infected with a sublethal dose of *L. monocytogenes* ($3 \times 10^4$ colony forming units (CFU)). Bacterial titers were determined 3 days or nine days after infection and found to be up to $10^6$-fold higher in the livers of TCCR-deficient mice (FIG. 17C).

The role of TCCR in mediating the differentiation of a Th1 response in vitro was next investigated. CD4+ T cells from wild type and TCCR-deficient mice were differentiated in vitro in the presence of irradiated APC under conditions that favor either Th1 or Th2 cell development. After 34 days in culture, cells were washed and restimulated with ConA, and 24 h later, supernatants were analyzed for the presence of cytokines. When differentiated into Th1 cells, TCCR-deficient lymphocytes produced 80% less IFN—than their wild type littermates (FIG. 18A). In contrast, TCCR-deficient lymphocytes grown in the presence of IL4 and anti-IFN-antibodies produced slightly more IL-4. Similar results were obtained with CD4+ CD45Rb$^{high}$ naïve T cells. This effect is intrinsic to the T cells for 2 reasons: First, similar results were obtained when T cells were differentiated in the presence of APC derived from wild type or TCCR-deficient mice. Second, the effect was reproducible in an APC free system where T cell differentiation was carried out using plate-immobilized anti-CD3/CD28 (FIG. 18B). The reduction in IFN production also correlates with a decrease in the number of IFN producing cells as measured by intracellular FACS staining. The observed Th1 deficiency did not appear to be the result of a defect in the IL-12 receptor as both subunits of the receptor were expressed normally in activated T-cells. Since IL-12 could still promote the proliferation of ConA stimulated T cells from wild type and TCCR-deficient mice, there seems to be no defect in the IL-12 signaling pathway in these mice (FIGS. 18C and D).

Table 3(A-Q) provides the complete source code for the ALIGN-2 sequence comparison computer program. This source code may be routinely compiled for use on a UNIX operating system to provide the ALIGN-2 sequence comparison computer program.

TABLE 2A

| PRO | XXXXXXXXXXXXXXX | (Length = 15 amino acids) |
|---|---|---|
| Comparison Protein | XXXXXYYYYYYY | (Length = 12 amino acids) |

% amino acid sequence identity =
(the number of identically matching amino acid residues between the two polypeptide sequences as determined by ALIGN-2) divided by (the total number of amino acid residues of the PRO polypeptide) = 5 divided by 15 = 33.3%

TABLE 2B

| PRO | XXXXXXXXXX | (Length = 10 amino acids) |
|---|---|---|
| Comparison Protein | XXXXXYYYYYYZZYZ | (Length = 15 amino acids) |

% amino acid sequence identity =
(the number of identically matching amino acid residues between the two polypeptide sequences as determined by ALIGN-2) divided by (the total number of amino acid residues of the PRO polypeptide) = 5 divided by 10 = 50%

TABLE 2C

| PRO-DNA | NNNNNNNNNNNNNN | (Length = 14 nucleotides) |
|---|---|---|
| Comparison DNA | NNNNNNLLLLLLLLLL | (Length = 16 nucleotides) |

% nucleic acid sequence identity =
(the number of identically matching nucleotides between the two nucleic acid sequences as determined by ALIGN-2) divided by (the total number of nucleotides of the PRO-DNA nucleic acid sequence) = 6 divided by 14 = 42.9%

TABLE 2D

| PRO-DNA | NNNNNNNNNNNN | (Length = 12 nucleotides) |
|---|---|---|
| Comparison DNA | NNNNLLLVV | (Length = 9 nucleotides) |

% nucleic acid sequence identity =
(the number of identically matching nucleotides between the two nucleic acid sequences as determined by ALIGN-2) divided by (the total number of nucleotides of the PRO-DNA nucleic acid sequence) = 4 divided by 12 = 33.3%

Table 3A

```
/*
 *
 * C-C increased from 12 to 15
 * Z is average of EQ
 * B is average of ND
 * match with stop is _M; stop-stop = 0; J (joker) match = 0
 */
define  _M    -8       /* value of a match with a stop */ int    _day[26][26] = {
/*     A B C D E F G H I J K L M N O P Q R S T U V W X Y Z */
/* A */  { 2, 0,-2, 0, 0,-4, 1,-1,-1, 0,-1,-2,-1, 0,_M, 1, 0,-2, 1, 1, 0, 0,-6, 0,-3, 0},
/* B */  { 0, 3,-4, 3, 2,-5, 0, 1,-2, 0, 0,-3,-2, 2,_M,-1, 1, 0, 0, 0, 0,-2,-5, 0,-3, 1},
/* C */  {-2,-4,15,-5,-5,-4,-3,-3,-2, 0,-5,-6,-5,-4,_M,-3,-5,-4, 0,-2, 0,-2,-8, 0, 0,-5},
/* D */  { 0, 3,-5, 4, 3,-6, 1, 1,-2, 0, 0,-4,-3, 2,_M,-1, 2,-1, 0, 0, 0,-2,-7, 0,-4, 2},
/* E */  { 0, 2,-5, 3, 4,-5, 0, 1,-2, 0, 0,-3,-2, 1,_M,-1, 2,-1, 0, 0, 0,-2,-7, 0,-4, 3},
/* F */  {-4,-5,-4,-6,-5, 9,-5,-2, 1, 0,-5, 2, 0,-4,_M,-5,-5,-4,-3,-3, 0,-1, 0, 0, 7,-5},
/* G */  { 1, 0,-3, 1, 0,-5, 5,-2,-3, 0,-2,-4,-3, 0,_M,-1,-1,-3, 1, 0, 0,-1,-7, 0,-5, 0},
/* H */  {-1, 1,-3, 1, 1,-2,-2, 6,-2, 0, 0,-2,-2, 2,_M, 0, 3, 2,-1,-1, 0,-2,-3, 0, 0, 2},
/* I */  {-1,-2,-2,-2,-2, 1,-3,-2, 5, 0,-2, 2, 2,-2,_M,-2,-2,-2,-1, 0, 0, 4,-5, 0,-1,-2},
/* J */  { 0, 0, 0, 0, 0, 0, 0, 0, 0, 0, 0, 0, 0, 0,_M, 0, 0, 0, 0, 0, 0, 0, 0, 0, 0, 0},
/* K */  {-1, 0,-5, 0, 0,-5,-2, 0,-2, 0, 5,-3, 0, 1,_M,-1, 1, 3, 0, 0, 0,-2,-3, 0,-4, 0},
/* L */  {-2,-3,-6,-4,-3, 2,-4,-2, 2, 0,-3, 6, 4,-3,_M,-3,-2,-3,-3,-1, 0, 2,-2, 0,-1,-2},
/* M */  {-1,-2,-5,-3,-2, 0,-3,-2, 2, 0, 0, 4, 6,-2,_M,-2,-1, 0,-2,-1, 0, 2,-4, 0,-2,-1},
/* N */  { 0, 2,-4, 2, 1,-4, 0, 2,-2, 0, 1,-3,-2, 2,_M,-1, 1, 0, 1, 0, 0,-2,-4, 0,-2, 1},
/* O */  {_M,_M,_M,_M,_M,_M,_M,_M,_M,_M,_M,_M,_M,_M, 0,_M,_M,_M,_M,_M,_M,_M,_M,_M,_M,_M},
/* P */  { 1,-1,-3,-1,-1,-5,-1, 0,-2, 0,-1,-3,-2,-1,_M, 6, 0, 0, 1, 0, 0,-1,-6, 0,-5, 0},
/* Q */  { 0, 1,-5, 2, 2,-5,-1, 3,-2, 0, 1,-2,-1, 1,_M, 0, 4, 1,-1,-1, 0,-2,-5, 0,-4, 3},
/* R */  {-2, 0,-4,-1,-1,-4,-3, 2,-2, 0, 3,-3, 0, 0,_M, 0, 1, 6, 0,-1, 0,-2, 2, 0,-4, 0},
/* S */  { 1, 0, 0, 0, 0,-3, 1,-1,-1, 0, 0,-3,-2, 1,_M, 1,-1, 0, 2, 1, 0,-1,-2, 0,-3, 0},
/* T */  { 1, 0,-2, 0, 0,-3, 0,-1, 0, 0, 0,-1,-1, 0,_M, 0,-1,-1, 1, 3, 0, 0,-5, 0,-3, 0},
/* U */  { 0, 0, 0, 0, 0, 0, 0, 0, 0, 0, 0, 0, 0, 0,_M, 0, 0, 0, 0, 0, 0, 0, 0, 0, 0, 0},
/* V */  { 0,-2,-2,-2,-2,-1,-1,-2, 4, 0,-2, 2, 2,-2,_M,-1,-2,-2,-1, 0, 0, 4,-6, 0,-2,-2},
/* W */  {-6,-5,-8,-7,-7, 0,-7,-3,-5, 0,-3,-2,-4,-4,_M,-6,-5, 2,-2,-5, 0,-6,17, 0, 0,-6},
/* X */  { 0, 0, 0, 0, 0, 0, 0, 0, 0, 0, 0, 0, 0, 0,_M, 0, 0, 0, 0, 0, 0, 0, 0, 0, 0, 0},
/* Y */  {-3,-3, 0,-4,-4, 7,-5, 0,-1, 0,-4,-1,-2,-2,_M,-5,-4,-4,-3,-3, 0,-2, 0, 0,10,-4},
/* Z */  { 0, 1,-5, 2, 3,-5, 0, 2,-2, 0, 0,-2,-1, 1,_M, 0, 3, 0, 0, 0, 0,-2,-6, 0,-4, 4}
};
```

Table 3B

```c
/*
*/
#include <stdio.h>
include <ctype.h> define   MAXJMP   16      /* max jumps in a diag */
define   MAXGAP   24      /* don't continue to penalize gaps larger than this */
#define   JMPS     1024    /* max jmps in an path */
define   MX       4       /* save if there's at least MX-1 bases since last jmp */ define   DMAT     3       /* value of matching bases */
define   DMIS     0       /* penalty for mismatched bases */
#define   DINS0    8       /* penalty for a gap */
#define   DINS1    1       /* penalty per base */
#define   PINS0    8       /* penalty for a gap */
define   PINS1    4       /* penalty per residue */ struct jmp {
        short           n[MAXJMP];      /* size of jmp (neg for dely) */
        unsigned short  x[MAXJMP];      /* base no. of jmp in seq x */
};                                      /* limits seq to 2^16 -1 */ struct diag {
        int         score;      /* score at last jmp */
        long        offset;     /* offset of prev block */
        short       ijmp;       /* current jmp index */
        struct jmp  jp;         /* list of jmps */
};

struct path {
        int     spc;            /* number of leading spaces */
        short   n[JMPS];        /* size of jmp (gap) */
        int     x[JMPS];        /* loc of jmp (last elem before gap) */
};
char            *ofile;         /* output file name */
char            *namex[2];      /* seq names: getseqs() */
char            *prog;          /* prog name for err msgs */
char            *seqx[2];       /* seqs: getseqs() */
int             dmax;           /* best diag: nw() */
int             dmax0;          /* final diag */
int             dna;            /* set if dna: main() */
int             endgaps;        /* set if penalizing end gaps */
int             gapx, gapy;     /* total gaps in seqs */
int             len0, len1;     /* seq lens */
int             ngapx, ngapy;   /* total size of gaps */
int             smax;           /* max score: nw() */
int             *xbm;           /* bitmap for matching */
long            offset;         /* current offset in jmp file */
struct diag     *dx;            /* holds diagonals */
struct path     pp[2];          /* holds path for seqs */
char            *calloc(), *malloc(), *index(), *strcpy();
char            *getseq(), *g_calloc();
```

Page 1 of nw.h

Table 3C

```
/* Needleman-Wunsch alignment program
 *
 * usage: progs file1 file2
 *   where file1 and file2 are two dna or two protein sequences.
 *   The sequences can be in upper- or lower-case an may contain ambiguity
 *   Any lines beginning with ';', '>' or '<' are ignored
 *   Max file length is 65535 (limited by unsigned short x in the jmp struct)
 *   A sequence with 1/3 or more of its elements ACGTU is assumed to be DNA
 *   Output is in the file "align.out"
 *
 * The program may create a tmp file in /tmp to hold info about traceback.
 * Original version developed under BSD 4.3 on a vax 8650
 */
#include "nw.h"
#include "day.h"

static    _dbval[26] = {
          1,14,2,13,0,0,4,11,0,0,12,0,3,15,0,0,0,5,6,8,8,7,9,0,10,0
};

static    _pbval[26] = {
          1, 2|(1<<('D'-'A'))|(1<<('N'-'A')), 4, 8, 16, 32, 64,
          128, 256, 0xFFFFFFF, 1<<10, 1<<11, 1<<12, 1<<13, 1<<14,
          1<<15, 1<<16, 1<<17, 1<<18, 1<<19, 1<<20, 1<<21, 1<<22,
          1<<23, 1<<24, 1<<25|(1<<('E'-'A'))|(1<<('Q'-'A'))
};

main(ac, av)                                                                    main
          int       ac;
          char      *av[];
{
          prog = av[0];
          if (ac != 3) {
                    fprintf(stderr,"usage: %s file1 file2\n", prog);
                    fprintf(stderr,"where file1 and file2 are two dna or two protein sequences.\n");
                    fprintf(stderr,"The sequences can be in upper- or lower-case\n");
                    fprintf(stderr,"Any lines beginning with ';' or '<' are ignored\n");
                    fprintf(stderr,"Output is in the file \"align.out\"\n");
                    exit(1);
          }
          namex[0] = av[1];
          namex[1] = av[2];
          seqx[0] = getseq(namex[0], &len0);
          seqx[1] = getseq(namex[1], &len1);
          xbm = (dna)? _dbval : _pbval;
          endgaps = 0;                  /* 1 to penalize endgaps */
          ofile = "align.out";          /* output file */
          nw();                         /* fill in the matrix, get the possible jmps */
          readjmps();                   /* get the actual jmps */
          print();                      /* print stats, alignment */
          cleanup(0);                   /* unlink any tmp files */
}
```

Page 1 of nw.c

Table 3D

```
/* do the alignment, return best score: main()
 * dna: values in Fitch and Smith, PNAS, 80, 1382-1386, 1983
 * pro: PAM 250 values
 * When scores are equal, we prefer mismatches to any gap, prefer
 * a new gap to extending an ongoing gap, and prefer a gap in seqx
 * to a gap in seq y.
 */
nw()                                                                            nw
{
        char            *px, *py;        /* seqs and ptrs */
        int             *ndely, *dely;   /* keep track of dely */
        int             ndelx, delx;     /* keep track of delx */
        int             *tmp;            /* for swapping row0, row1 */
        int             mis;             /* score for each type */
        int             ins0, ins1;      /* insertion penalties */
        register        id;              /* diagonal index */
        register        ij;              /* jmp index */
        register        *col0, *col1;    /* score for curr, last row */
        register        xx, yy;          /* index into seqs */ dx = (struct diag *)g_calloc("to get diags", len0+len1+1, sizeof(struct diag));
        ndely = (int *)g_calloc("to get ndely", len1+1, sizeof(int));
        dely = (int *)g_calloc("to get dely", len1+1, sizeof(int));
        col0 = (int *)g_calloc("to get col0", len1+1, sizeof(int));
        col1 = (int *)g_calloc("to get col1", len1+1, sizeof(int));
        ins0 = (dna)? DINS0 : PINS0;
        ins1 = (dna)? DINS1 : PINS1;
        smax = -10000;
        if (endgaps) {
                for (col0[0] = dely[0] = -ins0, yy = 1; yy <= len1; yy++) {
                        col0[yy] = dely[yy] = col0[yy-1] - ins1;
                        ndely[yy] = yy;               }
                col0[0] = 0;         /* Waterman Bull Math Biol 84 */       }
        else
                for (yy = 1; yy <= len1; yy++)
                        dely[yy] = -ins0;
        /* fill in match matrix
        */
        for (px = seqx[0], xx = 1; xx <= len0; px++, xx++) {
                /* initialize first entry in col
                */
                if (endgaps) {
                        if (xx == 1)
                                col1[0] = delx = -(ins0+ins1);
                        else
                                col1[0] = delx = col0[0] - ins1;
                        ndelx = xx;
                }
                else {
                        col1[0] = 0;
                        delx = -ins0;
                        ndelx = 0;
                }
```

Table 3E

...nw

```
for (py = seqx[1], yy = 1; yy <= len1; py++, yy++) {
        mis = col0[yy-1];
        if (dna)
                mis += (xbm[*px-'A']&xbm[*py-'A'])? DMAT : DMIS;
        else
                mis += _day[*px-'A'][*py-'A'];

/* update penalty for del in x seq;
         * favor new del over ongong del
         * ignore MAXGAP if weighting endgaps
         */
        if (endgaps || ndely[yy] < MAXGAP) {
                if (col0[yy] - ins0 >= dely[yy]) {
                        dely[yy] = col0[yy] - (ins0+ins1);
                        ndely[yy] = 1;
                } else {
                        dely[yy] -= ins1;
                        ndely[yy]++;
                }
        } else {
                if (col0[yy] - (ins0+ins1) >= dely[yy]) {
                        dely[yy] = col0[yy] - (ins0+ins1);
                        ndely[yy] = 1;
                } else
                        ndely[yy]++;
        }

/* update penalty for del in y seq;
         * favor new del over ongong del
         */
        if (endgaps || ndelx < MAXGAP) {
                if (col1[yy-1] - ins0 >= delx) {
                        delx = col1[yy-1] - (ins0+ins1);
                        ndelx = 1;
                } else {
                        delx -= ins1;
                        ndelx++;
                }
        } else {
                if (col1[yy-1] - (ins0+ins1) >= delx) {
                        delx = col1[yy-1] - (ins0+ins1);
                        ndelx = 1;
                } else
                        ndelx++;
        }

/* pick the maximum score; we're favoring
         * mis over any del and delx over dely
         */
```

Page 3 of nw.c

Table 3F

...nw

```
                id = xx - yy + len1 - 1;
                if (mis >= delx && mis >= dely[yy])
                        col1[yy] = mis;
                else if (delx >= dely[yy]) {
                        col1[yy] = delx;
                        ij = dx[id].ijmp;
                        if (dx[id].jp.n[0] && (!dna || (ndelx >= MAXJMP
                        && xx > dx[id].jp.x[ij]+MX) || mis > dx[id].score+DINS0)) {
                                dx[id].ijmp++;
                                if (++ij >= MAXJMP) {
                                        writejmps(id);
                                        ij = dx[id].ijmp = 0;
                                        dx[id].offset = offset;
                                        offset += sizeof(struct jmp) + sizeof(offset);      }
                        }
                        dx[id].jp.n[ij] = ndelx;
                        dx[id].jp.x[ij] = xx;
                        dx[id].score = delx;                        }
                else {  col1[yy] = dely[yy];
                        ij = dx[id].ijmp;
        if (dx[id].jp.n[0] && (!dna || (ndely[yy] >= MAXJMP
                        && xx > dx[id].jp.x[ij]+MX) || mis > dx[id].score+DINS0)) {
                                dx[id].ijmp++;
                                if (++ij >= MAXJMP) {
                                        writejmps(id);
                                        ij = dx[id].ijmp = 0;
                                        dx[id].offset = offset;
                                        offset += sizeof(struct jmp) + sizeof(offset);      }           }
                        dx[id].jp.n[ij] = -ndely[yy];
                        dx[id].jp.x[ij] = xx;
                        dx[id].score = dely[yy];                    }
                if (xx == len0 && yy < len1) {
                        /* last col
                        */
                        if (endgaps)
                                col1[yy] -= ins0+ins1*(len1-yy);
                        if (col1[yy] > smax) {
                                smax = col1[yy];
                                dmax = id;              }
                }
        }
        if (endgaps && xx < len0)
                col1[yy-1] -= ins0+ins1*(len0-xx);
        if (col1[yy-1] > smax) {
                smax = col1[yy-1];
                dmax = id;                      }
        tmp = col0; col0 = col1; col1 = tmp;    }
(void) free((char *)ndely);
(void) free((char *)dely);
(void) free((char *)col0);
(void) free((char *)col1);
}
```

Page 4 of nw.c

Table 3G

```
/*
 *
 * print() -- only routine visible outside this module
 *
 * static:
 * getmat() -- trace back best path, count matches: print()
 * pr_align() -- print alignment of described in array p[]: print()
 * dumpblock() -- dump a block of lines with numbers, stars: pr_align()
 * nums() -- put out a number line: dumpblock()
 * putline() -- put out a line (name, [num], seq, [num]): dumpblock()
 * stars() - -put a line of stars: dumpblock()
 * stripname() -- strip any path and prefix from a seqname
 */
#include "nw.h"
#define SPC      3
#define P_LINE   256        /* maximum output line */
#define P_SPC    3          /* space between name or num and seq */
extern    _day[26][26];
int       olen;             /* set output line length */
FILE      *fx;              /* output file */
print()
{
          int      lx, ly, firstgap, lastgap;       /* overlap */ if ((fx = fopen(ofile, "w")) == 0) {
                    fprintf(stderr,"%s: can't write %s\n", prog, ofile);
                    cleanup(1);        }
          fprintf(fx, "<first sequence: %s (length = %d)\n", namex[0], len0);
          fprintf(fx, "<second sequence: %s (length = %d)\n", namex[1], len1);
          olen = 60;
          lx = len0;
          ly = len1;
          firstgap = lastgap = 0;
          if (dmax < len1 - 1) {           /* leading gap in x */
                    pp[0].spc = firstgap = len1 - dmax - 1;
                    ly -= pp[0].spc;
          }
          else if (dmax > len1 - 1) {      /* leading gap in y */
                    pp[1].spc = firstgap = dmax - (len1 - 1);
                    lx -= pp[1].spc;
          }
          if (dmax0 < len0 - 1) {          /* trailing gap in x */
                    lastgap = len0 - dmax0 -1;
                    lx -= lastgap;
          }
          else if (dmax0 > len0 - 1) {     /* trailing gap in y */
                    lastgap = dmax0 - (len0 - 1);
                    ly -= lastgap;
          }
          getmat(lx, ly, firstgap, lastgap);
          pr_align();
}
``` print

Table 3H

```c
/*
 * trace back the best path, count matches
 */
static
getmat(lx, ly, firstgap, lastgap)
        int     lx, ly;                     /* "core" (minus endgaps) */
        int     firstgap, lastgap;          /* leading trailing overlap */
{
        int             nm, i0, i1, siz0, siz1;
        char            outx[32];
        double          pct;
        register        n0, n1;
        register char   *p0, *p1;
        /* get total matches, score
         */
        i0 = i1 = siz0 = siz1 = 0;
        p0 = seqx[0] + pp[1].spc;
        p1 = seqx[1] + pp[0].spc;
        n0 = pp[1].spc + 1;
        n1 = pp[0].spc + 1;
        nm = 0;
        while ( *p0 && *p1 ) {
                if (siz0) {
                        p1++;
                        n1++;
                        siz0--;     }
                else if (siz1) {
                        p0++;
                        n0++;
                        siz1--;     }
                else {
                        if (xbm[*p0-'A']&xbm[*p1-'A'])
                                nm++;
                        if (n0++ == pp[0].x[i0])
                                siz0 = pp[0].n[i0++];
                        if (n1++ == pp[1].x[i1])
                                siz1 = pp[1].n[i1++];
                        p0++;
                        p1++;       }
        }
        /* pct homology:
         * if penalizing endgaps, base is the shorter seq
         * else, knock off overhangs and take shorter core
         */
        if (endgaps)
                lx = (len0 < len1)? len0 : len1;
        else
                lx = (lx < ly)? lx : ly;
        pct = 100.*(double)nm/(double)lx;
        fprintf(fx, "\n");
        fprintf(fx, "<%d match%s in an overlap of %d: %.2f percent similarity\n",
                nm, (nm == 1)? "" : "es", lx, pct);
``` getmat

Page 2 of nwprint.c

Table 3I

```
                    fprintf(fx, "<gaps in first sequence: %d", gapx);                                      ...getmat
                    if (gapx) {
                                (void) sprintf(outx, " (%d %s%s)",
                                        ngapx, (dna)? "base":"residue", (ngapx == 1)? "":"s");
                                fprintf(fx,"%s", outx);
                    fprintf(fx, ", gaps in second sequence: %d", gapy);
                    if (gapy) {(void) sprintf(outx, " (%d %s%s)",
                                        ngapy, (dna)? "base":"residue", (ngapy == 1)? "":"s");
                                fprintf(fx,"%s", outx);          }
                    if (dna)
                                fprintf(fx,
                                "\n<score: %d (match = %d, mismatch = %d, gap penalty = %d + %d per base)\n",
                                smax, DMAT, DMIS, DINS0, DINS1);
                    else
                                fprintf(fx,
                                "\n<score: %d (Dayhoff PAM 250 matrix, gap penalty = %d + %d per residue)\n",
                                smax, PINS0, PINS1);
                    if (endgaps)
                                fprintf(fx,
                                "<endgaps penalized. left endgap: %d %s%s, right endgap: %d %s%s\n",
                                firstgap, (dna)? "base" : "residue", (firstgap == 1)? "" : "s",
                                lastgap, (dna)? "base" : "residue", (lastgap == 1)? "" : "s");
                    else
                                fprintf(fx, "<endgaps not penalized\n");   }
static              nm;                 /* matches in core -- for checking */
static              lmax;               /* lengths of stripped file names */
static              ij[2];              /* jmp index for a path */
static              nc[2];              /* number at start of current line */
static              ni[2];              /* current elem number -- for gapping */
static              siz[2];
static char         *ps[2];             /* ptr to current element */
static char         *po[2];             /* ptr to next output char slot */
static char         out[2][P_LINE];     /* output line */
static char         star[P_LINE];       /* set by stars() */
/*
* print alignment of described in struct path pp[ ]
*/
static                                                                                                     pr_align
pr_align()
{
          int       nn;        /* char count */
          int       more;
          register  i;
          for (i = 0, lmax = 0; i < 2; i++) {nn = stripname(namex[i]);
                    if (nn > lmax)
                              lmax = nn;
                    nc[i] = 1;
                    ni[i] = 1;
                    siz[i] = ij[i] = 0;
                    ps[i] = seqx[i];
                    po[i] = out[i];
          }
```

Table 3J

```
        for (nn = nm = 0, more = 1; more; ) {                                          ...pr_align
                for (i = more = 0; i < 2; i++) {
                        /*
                         * do we have more of this sequence?
                         */
                        if (!*ps[i])
                                continue;
                        more++;
                        if (pp[i].spc) {       /* leading space */
                                *po[i]++ = ' ';
                                pp[i].spc--;                    }
                        else if (siz[i]) {     /* in a gap */
                                *po[i]++ = '-';
                                siz[i]--;                       }
                        else {                 /* we're putting a seq element
                                                */
                                *po[i] = *ps[i];
                                if (islower(*ps[i]))
                                        *ps[i] = toupper(*ps[i]);
                                po[i]++;
                                ps[i]++;
                                /*
                                 * are we at next gap for this seq?
                                 */
                                if (ni[i] == pp[i].x[ij[i]]) {
                                        /*
                                         * we need to merge all gaps
                                         * at this location
                                         */
                                        siz[i] = pp[i].n[ij[i]++];
                                        while (ni[i] == pp[i].x[ij[i]])
                                                siz[i] += pp[i].n[ij[i]++];    }
                                ni[i]++;
                        }
                }
                if (++nn == olen || !more && nn) {
                        dumpblock();
                        for (i = 0; i < 2; i++)
                                po[i] = out[i];
                        nn = 0;        }
        }
}
/*
 * dump a block of lines, including numbers, stars: pr_align()
 */
static
dumpblock()                                                                             dumpblock
{
        register i;
        for (i = 0; i < 2; i++)
                *po[i]-- = '\0';
```

Table 3K

```
                (void) putc('\n', fx);
                for (i = 0; i < 2; i++) {
                        if (*out[i] && (*out[i] != ' ' || *(po[i]) != ' ')) {
                                if (i == 0)
                                        nums(i);
                                if (i == 0 && *out[1])
                                        stars();
                                putline(i);
                                if (i == 0 && *out[1])
                                        fprintf(fx, star);
                                if (i == 1)
                                        nums(i);              }
                }
        }
}
/*
* put out a number line: dumpblock()
*/
static
nums(ix)
        int     ix;     /* index in out[] holding seq line */
{       char    nline[P_LINE];
        register        i, j;
        register char   *pn, *px, *py;
        for (pn = nline, i = 0; i < lmax+P_SPC; i++, pn++)
                *pn = ' ';
        for (i = nc[ix], py = out[ix]; *py; py++, pn++) {
                if (*py == ' ' || *py == '-')
                        *pn = ' ';
                else {
                        if (i%10 == 0 || (i == 1 && nc[ix] != 1)) {
                                j = (i < 0)? -i : i;
                                for (px = pn; j; j /= 10, px--)
                                        *px = j%10 + '0';
                                if (i < 0)
                                        *px = '-';                }
                        else
                                *pn = ' ';
                        i++;            }
        }
        *pn = '\0';
        nc[ix] = i;
        for (pn = nline; *pn; pn++)
                (void) putc(*pn, fx);
        (void) putc('\n', fx);}
/*
* put out a line (name, [num], seq, [num]): dumpblock()
*/
static
putline(ix)
        int     ix;
{
```

...dumpblock nums putline

Page 5 of nwprint.c

Table 3L

```
        int             i;
        register char   *px;
        for (px = namex[ix], i = 0; *px && *px != ' '; px++, i++)
                (void) putc(*px, fx);
        for (; i < lmax+P_SPC; i++)
                (void) putc(' ', fx);
        /* these count from 1:
         * ni[] is current element (from 1)
         * nc[] is number at start of current line
         */
        for (px = out[ix]; *px; px++)
                (void) putc(*px&0x7F, fx);
        (void) putc('\n', fx);
}

/*
 * put a line of stars (seqs always in out[0], out[1]): dumpblock()
 */
static
stars()
{
        int             i;
        register char   *p0, *p1, cx, *px;

if (!*out[0] || (*out[0] == ' ' && *(po[0]) == ' ') ||
            !*out[1] || (*out[1] == ' ' && *(po[1]) == ' '))
                return;
        px = star;
        for (i = lmax+P_SPC; i; i--)
                *px++ = ' ';

for (p0 = out[0], p1 = out[1]; *p0 && *p1; p0++, p1++) {
                if (isalpha(*p0) && isalpha(*p1)) {
                        if (xbm[*p0-'A']&xbm[*p1-'A']) {
                                cx = '*';
                                nm++;
                        }
                        else if (!dna && _day[*p0-'A'][*p1-'A'] > 0)
                                cx = '.';
                        else
                                cx = ' ';
                }
                else
                        cx = ' ';
                *px++ = cx;
        }
        *px++ = '\n';
        *px = '\0';
}
```

...putline stars

Page 6 of nwprint.c

Table 3M

```
/*
 * strip path or prefix from pn, return len: pr_align()
 */
static
stripname(pn)                                                           stripname
        char    *pn;    /* file name (may be path) */
{
        register char   *px, *py;

py = 0;
        for (px = pn; *px; px++)
                if (*px == '/')
                        py = px + 1;
        if (py)
                (void) strcpy(pn, py);
        return(strlen(pn));

}
```

Page 7 of nwprint.c

Table 3N

```
/*
* cleanup() -- cleanup any tmp file
* getseq() -- read in seq, set dna, len, maxlen
* g_calloc() -- calloc() with error checkin
* readjmps() -- get the good jmps, from tmp file if necessary
* writejmps() -- write a filled array of jmps to a tmp file: nw()
*/
#include "nw.h"
#include <sys/file.h>
char      *jname = "/tmp/homgXXXXXX";        /* tmp file for jmps */
FILE      *fj;
int       cleanup();                          /* cleanup tmp file */
long      lseek();
/*
* remove any tmp file if we blow
*/
cleanup(i)                                                                                cleanup
          int       i;
{         if (fj)
                    (void) unlink(jname);
          exit(i);}
/*
* read, return ptr to seq, set dna, len, maxlen
* skip lines starting with ';', '<', or '>'
* seq in upper or lower case
*/
char      *
getseq(file, len)                                                                         getseq
          char      *file;     /* file name */
          int       *len;      /* seq len */
{
          char               line[1024], *pseq;
          register char      *px, *py;
          int                natgc, tlen;
          FILE               *fp;
          if ((fp = fopen(file,"r")) == 0) {
                    fprintf(stderr,"%s: can't read %s\n", prog, file);
                    exit(1);
          }
          tlen = natgc = 0;
          while (fgets(line, 1024, fp)) {
                    if (*line == ';' || *line == '<' || *line == '>')
                              continue;
                    for (px = line; *px != '\n'; px++)
                              if (isupper(*px) || islower(*px))
                                        tlen++;
          }
          if ((pseq = malloc((unsigned)(tlen+6))) == 0) {
                    fprintf(stderr,"%s: malloc() failed to get %d bytes for %s\n", prog, tlen+6, file);
                    exit(1);
          }
          pseq[0] = pseq[1] = pseq[2] = pseq[3] = '\0';
```

Table 3O

...getseq

```
            py = pseq + 4;
            *len = tlen;
            rewind(fp);
            while (fgets(line, 1024, fp)) {
                        if (*line == ';' || *line == '<' || *line == '>')
                                    continue;
                        for (px = line; *px != '\n'; px++) {
                                    if (isupper(*px))
                                                *py++ = *px;
                                    else if (islower(*px))
                                                *py++ = toupper(*px);
                                    if (index("ATGCU",*(py-1)))
                                                natgc++;            }
            }
            *py++ = '\0';
            *py = '\0';
            (void) fclose(fp);
            dna = natgc > (tlen/3);
            return(pseq+4);
}
char      *
g_calloc(msg, nx, sz)
            char      *msg;             /* program, calling routine */
            int       nx, sz;           /* number and size of elements */
{
            char                *px, *calloc();
            if ((px = calloc((unsigned)nx, (unsigned)sz)) == 0) {
                        if (*msg) {
                                    fprintf(stderr, "%s: g_calloc() failed %s (n=%d, sz=%d)\n", prog, msg, nx, sz);
                                    exit(1);            }
            }
            return(px);
}
/*
 * get final jmps from dx[] or tmp file, set pp[], reset dmax: main()
 */
readjmps()
{
            int                 fd = -1;
            int                 siz, i0, i1;
            register  i, j, xx;
            if (fj) {
                        (void) fclose(fj);
                        if ((fd = open(jname, O_RDONLY, 0)) < 0) {
                                    fprintf(stderr, "%s: can't open() %s\n", prog, jname);
                                    cleanup(1);            }
            }
            for (i = i0 = i1 = 0, dmax0 = dmax, xx = len0; ; i++) {
                        while (1) {
                                    for (j = dx[dmax].ijmp; j >= 0 && dx[dmax].jp.x[j] >= xx; j--)
                                                ;
``` g_calloc readjmps

Table 3P

...readjmps

```
                if (j < 0 && dx[dmax].offset && fj) {
                        (void) lseek(fd, dx[dmax].offset, 0);
                        (void) read(fd, (char *)&dx[dmax].jp, sizeof(struct jmp));
                        (void) read(fd, (char *)&dx[dmax].offset, sizeof(dx[dmax].offset));
                        dx[dmax].ijmp = MAXJMP-1;                                               }
                else
                        break;          }
        if (i >= JMPS) {
                fprintf(stderr, "%s: too many gaps in alignment\n", prog);
                cleanup(1);             }
        if (j >= 0) {
                siz = dx[dmax].jp.n[j];
                xx = dx[dmax].jp.x[j];
                dmax += siz;
                if (siz < 0) {                  /* gap in second seq */
                        pp[1].n[i1] = -siz;
                        xx += siz;
                        /* id = xx - yy + len1 - 1
                        */
                        pp[1].x[i1] = xx - dmax + len1 - 1;
                        gapy++;
                        ngapy -= siz;
/* ignore MAXGAP when doing endgaps */
                        siz = (-siz < MAXGAP || endgaps)? -siz : MAXGAP;
                        i1++;                   }
                else if (siz > 0) {     /* gap in first seq */
                        pp[0].n[i0] = siz;
                        pp[0].x[i0] = xx;
                        gapx++;
                        ngapx += siz;
/* ignore MAXGAP when doing endgaps */
                        siz = (siz < MAXGAP || endgaps)? siz : MAXGAP;
                        i0++;                   }
                }
                else
                        break;  }
        /* reverse the order of jmps
        */
        for (j = 0, i0--; j < i0; j++, i0--) {
                i = pp[0].n[j]; pp[0].n[j] = pp[0].n[i0]; pp[0].n[i0] = i;
                i = pp[0].x[j]; pp[0].x[j] = pp[0].x[i0]; pp[0].x[i0] = i;        }
        for (j = 0, i1--; j < i1; j++, i1--) {
                i = pp[1].n[j]; pp[1].n[j] = pp[1].n[i1]; pp[1].n[i1] = i;
                i = pp[1].x[j]; pp[1].x[j] = pp[1].x[i1]; pp[1].x[i1] = i;        }
        if (fd >= 0)
                (void) close(fd);
        if (fj) {
                (void) unlink(jname);
                fj = 0;
                offset = 0;}
}
```

Page 3 of nwsubr.c

Table 3Q

```
/*
 * write a filled jmp struct offset of the prev one (if any): nw()
 */
writejmps(ix)                                                                          writejmps
        int     ix;
{
        char    *mktemp();

if (!fj) {
                if (mktemp(jname) < 0) {
                        fprintf(stderr, "%s: can't mktemp() %s\n", prog, jname);
                        cleanup(1);
                }
                if ((fj = fopen(jname, "w")) == 0) {
                        fprintf(stderr, "%s: can't write %s\n", prog, jname);
                        exit(1);
                }
        }
        (void) fwrite((char *)&dx[ix].jp, sizeof(struct jmp), 1, fj);
        (void) fwrite((char *)&dx[ix].offset, sizeof(dx[ix].offset), 1, fj);
}
```

What is claimed is:

1. A method of treating an allergic disorder in a mammal comprising administering to said mammal a therapeutically effective amount of a T Cell Cytokine Receptor (TCCR) agonist antibody or TCCR binding fragment thereof, a bispecific TCCR agonist antibody, a heteroconjugate TCCR agonist antibody, or a TCCR agonist diabody, wherein any of said antibodies or fragment comprises two or more TCCR antigen binding sites.

2. The method of claim 1, wherein the allergic disorder asthma, allergic rhinitis, atopic dermatitis, or vernal conjunctivitis.

3. The method of claim 1, wherein the agonist antibody is a monoclonal antibody or fragment thereof comprising two or more TCCR antigen binding sites.

4. The method of claim 1, wherein the agonist antibody is a humanized antibody or fragment thereof comprising two or more TCCR antigen binding sites.

5. The method of claim 1, wherein said agonist is administered in combination with a cytotoxic agent, cytokine, anticancer agent, or growth inhibitory agent.

6. The method of claim 1, wherein the bispecific antibody, heteroconjugate antibody, or diabody binds two different TCCR epitopes.

7. The method of claim 1, wherein the antibody fragment is a F(ab')$_2$ fragment.

8. The method of claim 3, wherein the monoclonal antibody fragment is a F(ab')$_2$ fragment.

9. The method of claim 4, wherein the humanized antibody fragment is a F(ab')$_2$ fragment.

* * * * *

SEQUENCE LISTING

<160> NUMBER OF SEQ ID NOS: 16

<210> SEQ ID NO 1
<211> LENGTH: 636
<212> TYPE: PRT
<213> ORGANISM: Homo sapiens

<400> SEQUENCE: 1

```
Met Arg Gly Gly Arg Gly Ala Pro Phe Trp Leu Trp Pro Leu Pro
  1               5                  10                  15

Lys Leu Ala Leu Leu Pro Leu Leu Trp Val Leu Phe Gln Arg Thr
                 20                  25                  30

Arg Pro Gln Gly Ser Ala Gly Pro Leu Gln Cys Tyr Gly Val Gly
                 35                  40                  45

Pro Leu Gly Asp Leu Asn Cys Ser Trp Glu Pro Leu Gly Asp Leu
                 50                  55                  60

Gly Ala Pro Ser Glu Leu His Leu Gln Ser Gln Lys Tyr Arg Ser
                 65                  70                  75

Asn Lys Thr Gln Thr Val Ala Val Ala Ala Gly Arg Ser Trp Val
                 80                  85                  90

Ala Ile Pro Arg Glu Gln Leu Thr Met Ser Asp Lys Leu Leu Val
                 95                 100                 105

Trp Gly Thr Lys Ala Gly Gln Pro Leu Trp Pro Pro Val Phe Val
                110                 115                 120

Asn Leu Glu Thr Gln Met Lys Pro Asn Ala Pro Arg Leu Gly Pro
                125                 130                 135

Asp Val Asp Phe Ser Glu Asp Pro Leu Glu Ala Thr Val His
                140                 145                 150

Trp Ala Pro Pro Thr Trp Pro Ser His Lys Val Leu Ile Cys Gln
                155                 160                 165

Phe His Tyr Arg Arg Cys Gln Glu Ala Ala Trp Thr Leu Leu Glu
                170                 175                 180

Pro Glu Leu Lys Thr Ile Pro Leu Thr Pro Val Glu Ile Gln Asp
                185                 190                 195

Leu Glu Leu Ala Thr Gly Tyr Lys Val Tyr Gly Arg Cys Arg Met
                200                 205                 210

Glu Lys Glu Glu Asp Leu Trp Gly Glu Trp Ser Pro Ile Leu Ser
                215                 220                 225

Phe Gln Thr Pro Pro Ser Ala Pro Lys Asp Val Trp Val Ser Gly
                230                 235                 240

Asn Leu Cys Gly Thr Pro Gly Gly Glu Glu Pro Leu Leu Leu Trp
                245                 250                 255

Lys Ala Pro Gly Pro Cys Val Gln Val Ser Tyr Lys Val Trp Phe
                260                 265                 270

Trp Val Gly Gly Arg Glu Leu Ser Pro Glu Gly Ile Thr Cys Cys
                275                 280                 285

Cys Ser Leu Ile Pro Ser Gly Ala Glu Trp Ala Arg Val Ser Ala
                290                 295                 300

Val Asn Ala Thr Ser Trp Glu Pro Leu Thr Asn Leu Ser Leu Val
                305                 310                 315

Cys Leu Asp Ser Ala Ser Ala Pro Arg Ser Val Ala Val Ser Ser
                320                 325                 330

Ile Ala Gly Ser Thr Glu Leu Leu Val Thr Trp Gln Pro Gly Pro
```

-continued

```
                335                 340                 345
Gly Glu Pro Leu Glu His Val Val Asp Trp Ala Arg Asp Gly Asp
            350                 355                 360
Pro Leu Glu Lys Leu Asn Trp Val Arg Leu Pro Pro Gly Asn Leu
        365                 370                 375
Ser Ala Leu Leu Pro Gly Asn Phe Thr Val Gly Val Pro Tyr Arg
    380                 385                 390
Ile Thr Val Thr Ala Val Ser Ala Ser Gly Leu Ala Ser Ala Ser
395                 400                 405
Ser Val Trp Gly Phe Arg Glu Glu Leu Ala Pro Leu Val Gly Pro
        410                 415                 420
Thr Leu Trp Arg Leu Gln Asp Ala Pro Pro Gly Thr Pro Ala Ile
    425                 430                 435
Ala Trp Gly Glu Val Pro Arg His Gln Leu Arg Gly His Leu Thr
440                 445                 450
His Tyr Thr Leu Cys Ala Gln Ser Gly Thr Ser Pro Ser Val Cys
        455                 460                 465
Met Asn Val Ser Gly Asn Thr Gln Ser Val Thr Leu Pro Asp Leu
    470                 475                 480
Pro Trp Gly Pro Cys Glu Leu Trp Val Thr Ala Ser Thr Ile Ala
485                 490                 495
Gly Gln Gly Pro Pro Gly Pro Ile Leu Arg Leu His Leu Pro Asp
        500                 505                 510
Asn Thr Leu Arg Trp Lys Val Leu Pro Gly Ile Leu Phe Leu Trp
    515                 520                 525
Gly Leu Phe Leu Leu Gly Cys Gly Leu Ser Leu Ala Thr Ser Gly
530                 535                 540
Arg Cys Tyr His Leu Arg His Lys Val Leu Pro Arg Trp Val Trp
        545                 550                 555
Glu Lys Val Pro Asp Pro Ala Asn Ser Ser Ser Gly Gln Pro His
    560                 565                 570
Met Glu Gln Val Pro Glu Ala Gln Pro Leu Gly Asp Leu Pro Ile
575                 580                 585
Leu Glu Val Glu Glu Met Glu Pro Pro Val Met Glu Ser Ser
        590                 595                 600
Gln Pro Ala Gln Ala Thr Ala Pro Leu Asp Ser Gly Tyr Glu Lys
    605                 610                 615
His Phe Leu Pro Thr Pro Glu Glu Leu Gly Leu Leu Gly Pro Pro
620                 625                 630
Arg Pro Gln Val Leu Ala
            635

<210> SEQ ID NO 2
<211> LENGTH: 623
<212> TYPE: PRT
<213> ORGANISM: Mus musculus

<400> SEQUENCE: 2

Met Asn Arg Leu Arg Val Ala Arg Leu Thr Pro Leu Glu Leu Leu
  1               5                  10                  15
Leu Ser Leu Met Ser Leu Leu Leu Gly Thr Arg Pro His Gly Ser
                20                  25                  30
Pro Gly Pro Leu Gln Cys Tyr Ser Val Gly Pro Leu Gly Ile Leu
            35                  40                  45
```

-continued

```
Asn Cys Ser Trp Glu Pro Leu Gly Asp Leu Glu Thr Pro Pro Val
             50                  55                  60
Leu Tyr His Gln Ser Gln Lys Tyr His Pro Asn Arg Val Trp Glu
             65                  70                  75
Val Lys Val Pro Ser Lys Gln Ser Trp Val Thr Ile Pro Arg Glu
             80                  85                  90
Gln Phe Thr Met Ala Asp Lys Leu Leu Ile Trp Gly Thr Gln Lys
             95                 100                 105
Gly Arg Pro Leu Trp Ser Val Ser Val Asn Leu Glu Thr Gln
            110                 115                 120
Met Lys Pro Asp Thr Pro Gln Ile Phe Ser Gln Val Asp Ile Ser
            125                 130                 135
Glu Glu Ala Thr Leu Glu Ala Thr Val Gln Trp Ala Pro Pro Val
            140                 145                 150
Trp Pro Pro Gln Lys Ala Leu Thr Cys Gln Phe Arg Tyr Lys Glu
            155                 160                 165
Cys Gln Ala Glu Ala Trp Thr Arg Leu Glu Pro Gln Leu Lys Thr
            170                 175                 180
Asp Gly Leu Thr Pro Val Glu Met Gln Asn Leu Glu Pro Gly Thr
            185                 190                 195
Cys Tyr Gln Val Ser Gly Arg Cys Gln Val Glu Asn Gly Tyr Pro
            200                 205                 210
Trp Gly Glu Trp Ser Ser Pro Leu Ser Phe Gln Thr Pro Phe Leu
            215                 220                 225
Asp Pro Glu Asp Val Trp Val Ser Gly Thr Val Cys Glu Thr Ser
            230                 235                 240
Gly Lys Arg Ala Ala Leu Leu Val Trp Lys Asp Pro Arg Pro Cys
            245                 250                 255
Val Gln Val Thr Tyr Thr Val Trp Phe Gly Ala Gly Asp Ile Thr
            260                 265                 270
Thr Thr Gln Glu Glu Val Pro Cys Cys Lys Ser Pro Val Pro Ala
            275                 280                 285
Trp Met Glu Trp Ala Val Val Ser Pro Gly Asn Ser Thr Ser Trp
            290                 295                 300
Val Pro Pro Thr Asn Leu Ser Leu Val Cys Leu Ala Pro Glu Ser
            305                 310                 315
Ala Pro Cys Asp Val Gly Val Ser Ser Ala Asp Gly Ser Pro Gly
            320                 325                 330
Ile Lys Val Thr Trp Lys Gln Gly Thr Arg Lys Pro Leu Glu Tyr
            335                 340                 345
Val Val Asp Trp Ala Gln Asp Gly Asp Ser Leu Asp Lys Leu Asn
            350                 355                 360
Trp Thr Arg Leu Pro Pro Gly Asn Leu Ser Thr Leu Leu Pro Gly
            365                 370                 375
Glu Phe Lys Gly Gly Val Pro Tyr Arg Ile Thr Val Thr Ala Val
            380                 385                 390
Tyr Ser Gly Gly Leu Ala Ala Pro Ser Val Trp Gly Phe Arg
            395                 400                 405
Glu Glu Leu Val Pro Leu Ala Gly Pro Ala Val Trp Arg Leu Pro
            410                 415                 420
Asp Asp Pro Pro Gly Thr Pro Val Val Ala Trp Gly Glu Val Pro
            425                 430                 435
Arg His Gln Leu Arg Gly Gln Ala Thr His Tyr Thr Phe Cys Ile
```

```
                       440             445             450
Gln Ser Arg Gly Leu Ser Thr Val Cys Arg Asn Val Ser Ser Gln
                455             460             465

Thr Gln Thr Ala Thr Leu Pro Asn Leu His Ser Gly Ser Phe Lys
                470             475             480

Leu Trp Val Thr Val Ser Thr Val Ala Gly Gln Gly Pro Pro Gly
                485             490             495

Pro Asp Leu Ser Leu His Leu Pro Asp Asn Arg Ile Arg Trp Lys
                500             505             510

Ala Leu Pro Trp Phe Leu Ser Leu Trp Gly Leu Leu Met Gly
                515             520             525

Cys Gly Leu Ser Leu Ala Ser Thr Arg Cys Leu Gln Ala Arg Cys
                530             535             540

Leu His Trp Arg His Lys Leu Leu Pro Gln Trp Ile Trp Glu Arg
                545             550             555

Val Pro Asp Pro Ala Asn Ser Asn Ser Gly Gln Pro Tyr Ile Lys
                560             565             570

Glu Val Ser Leu Pro Gln Pro Pro Lys Asp Gly Pro Ile Leu Glu
                575             580             585

Val Glu Glu Val Glu Leu Gln Pro Val Val Glu Ser Pro Lys Ala
                590             595             600

Ser Ala Pro Ile Tyr Ser Gly Tyr Glu Lys His Phe Leu Pro Thr
                605             610             615

Pro Glu Glu Leu Gly Leu Leu Val
                620

<210> SEQ ID NO 3
<211> LENGTH: 2646
<212> TYPE: DNA
<213> ORGANISM: Homo sapiens
<220> FEATURE:
<221> NAME/KEY: unsure
<222> LOCATION: 2433
<223> OTHER INFORMATION: unknown base

<400> SEQUENCE: 3
gtgggttcgg cttcccgttg cgcctcgggg gctgtaccca gagctcgaag           50
aggagcagcg cggcccgcac ccggcaaggc tgggccggac tcggggctcc          100
cgagggacgc catgcgggga ggcaggggcg cccctttctg gctgtggccg          150
ctgcccaagc tggcgctgct gcctctgttg tgggtgcttt ccagcggac            200 gcgtccccag gcagcgccg ggccactgca gtgctacgga gttggaccct           250
tgggcgactt gaactgctcg tgggagcctc ttggggacct gggagccccc          300
tccgagttac acctccagag ccaaaagtac cgttccaaca aacccagac            350 tgtggcagtg gcagccggac ggagctgggt ggcattcct cgggaacagc           400 tcaccatgtc tgacaaactc cttgtctggg cactaaggc aggccagcct            450 ctctggcccc ccgtcttcgt gaacctagaa acccaaatga agccaaacgc          500
cccccggctg ggccctgacg tggactttc cgaggatgac cccctggagg           550
ccactgtcca ttgggcccca cctacatggc catctcataa agttctgatc          600
tgccagttcc actaccgaag atgtcaggag gcggcctgga ccctgctgga          650
accggagctg aagaccatac ccctgacccc tgttgagatc caagatttgg          700
agctagccac tggctacaaa gtgtatggcc gctgccggat ggagaaagaa          750
```

```
gaggatttgt ggggcgagtg gagcccatt ttgtccttcc agacaccgcc        800
ttctgctcca aaagatgtgt gggtatcagg gaacctctgt gggacgcctg        850
gaggagagga accttgctt ctatggaagg ccccagggcc ctgtgtgcag         900
gtgagctaca aagtctggtt ctgggttgga ggtcgtgagc tgagtccaga        950
aggaattacc tgctgctgct ccctaattcc cagtggggcg gagtgggcca       1000
gggtgtccgc tgtcaacgcc acaagctggg agcctctcac caacctctct       1050
ttggtctgct tggattcagc ctctgccccc cgtagcgtgg cagtcagcag       1100
catcgctggg agcacggagc tactggtgac ctggcaaccg gggcctgggg       1150
aaccactgga gcatgtagtg gactgggctc gagatgggga cccctggag        1200
aaactcaact gggtccggct tccccctggg aacctcagtg ctctgttacc       1250
agggaatttc actgtcgggg tccctatcg aatcactgtg accgcagtct        1300
ctgcttcagg cttggcctct gcatcctccg tctgggggtt cagggaggaa       1350
ttagcacccc tagtgggggcc aacgctttgg cgactccaag atgcccctcc      1400
agggaccccc gccatagcgt ggggagaggt cccaaggcac cagcttcgag       1450
gccacctcac ccactacacc ttgtgtgcac agagtggaac cagcccctcc       1500
gtctgcatga atgtgagtgg caacacacag agtgtcaccc tgcctgacct       1550
tccttggggt ccctgtgagc tgtgggtgac agcatctacc atcgctggac       1600
agggccctcc tggtcccatc ctccggcttc atctaccaga taacaccctg       1650
aggtggaaag ttctgccggg catcctattc ttgtggggct tgttcctgtt       1700
ggggtgtggc ctgagcctgg ccacctctgg aaggtgctac cacctaaggc       1750
acaaagtgct gccccgctgg gtctgggaga aagttcctga tcctgccaac       1800
agcagttcag gccagcccca catggagcaa gtacctgagg cccagcccct       1850
tggggacttg cccatcctgg aagtggagga gatggagccc ccgccggtta       1900
tggagtcctc ccagcccgcc caggccaccg ccccgcttga ctctgggtat       1950
gagaagcact tcctgcccac acctgaggag ctgggccttc tggggccccc       2000
caggccacag gttctggcct gaaccacacg tctggctggg ggctgccagc       2050
caggctagag ggatgctcat gcaggttgca ccccagtcct ggattagccc       2100
tcttgatgga tgaagacact gaggactcag agaggctgag tcacttacct       2150
gaggacaccc agccaggcag agctgggatt gaaggacccc tatagagaag       2200
ggcttggccc ccatggggaa gacacggatg gaaggtggag caaaggaaaa       2250
tacatgaaat tgagagtggc agctgcctgc caaaatctgt tccgctgtaa       2300
cagaactgaa tttggacccc agcacagtgg ctcacgcctg taatcccagc       2350
actttggcag gccaaggtgg aaggatcact tagagctagg agtttgagac       2400
cagcctgggc aatatagcaa gaccccctcac tanaaaaata aaacatcaaa      2450
aacaaaaaca attagctggg catgatggca cacacctgta gtccgagcca       2500
cttgggaggc tgaggtggga ggatcggttg agcccaggag ttcgaagctg       2550
cagggacctc tgattgcacc actgcactcc aggctgggta acagaatgag       2600
accttatctc aaaataaac aaactaataa aaaaaaaaa aaaaaa            2646
```

<210> SEQ ID NO 4

-continued

<211> LENGTH: 2005
<212> TYPE: DNA
<213> ORGANISM: Mus musculus

<400> SEQUENCE: 4

| | |
|---|---|
| tcggttctat cgatggggcc atgaaccggc tccggttgc acgcctcacg | 50 |
| ccgttggagc ttctgctgtc gctgatgtcg ctgctgctcg ggacgcggcc | 100 |
| ccacggcagt ccaggcccac tgcagtgcta cagcgtcggt cccctgggaa | 150 |
| tcctgaactg ctcctgggaa cctttgggcg acctggagac tccacctgtg | 200 |
| ctgtatcacc agagtcagaa ataccatccc aatagagtct gggaggtgaa | 250 |
| ggtgccttcc aaacaaagtt gggtgaccat tccccgggaa cagttcacca | 300 |
| tggctgacaa actcctcatc tgggggacac aaaaggacg gcctctgtgg | 350 |
| tcctctgtct ctgtgaacct ggagacccaa atgaagccag acacacctca | 400 |
| gatcttctct caagtggata tttctgagga agcaaccctg gaggccactg | 450 |
| tgcagtgggc gccgcccgtg tggccaccgc agaaagctct cacctgtcag | 500 |
| ttccggtaca aggaatgcca ggctgaagca tggacccggc tggagcccca | 550 |
| gctgaagaca gatgggctga ctcctgttga gatgcagaac ctggaacctg | 600 |
| gcacctgcta ccaggtgtct ggccgctgcc aggtggagaa cggatatcca | 650 |
| tggggcgagt ggagttcgcc cctgtccttc cagacgccat tcttagatcc | 700 |
| tgaagatgtg tgggtatcgg ggaccgtctg tgaaacttct ggcaaacggg | 750 |
| cagccctgct tgtctggaag gacccaagac cttgtgtgca ggtgacttac | 800 |
| acagtctggt tggggctgg agatattact acaactcaag aagaggtccc | 850 |
| gtgctgcaag tcccctgtcc ctgcatggat ggagtgggct gtggtctctc | 900 |
| ctggcaacag caccagctgg gtgcctccca ccaacctgtc tctggtgtgc | 950 |
| ttggctccag aatctgcccc ctgtgacgtg ggagtgagca gtgctgatgg | 1000 |
| gagcccaggg ataaaggtga cctggaaaca agggaccagg aaaccattgg | 1050 |
| agtatgtggt ggactgggct caagatggtg acagcctgga caagctcaac | 1100 |
| tggacccgtc tccccctgg aaacctcagc acattgttac caggggagtt | 1150 |
| caaaggaggg gtcccctatc gaattacagt gactgcagta tactctggag | 1200 |
| gattagctgc tgcacccctca gtttggggat tcagagagga gttagtaccc | 1250 |
| cttgctgggc cagcagtttg gcgacttcca gatgaccccc cagggacacc | 1300 |
| tgttgtagcc tggggagaag taccaagaca ccagctcaga ggccaggcta | 1350 |
| ctcactacac cttctgcata cagagcagag gcctctccac tgtctgcagg | 1400 |
| aacgtgagca gtcaaaccca gactgccact ctgcccaacc ttcactcggg | 1450 |
| ttccttcaag ctgtgggtga cggtgtccac cgttgcagga cagggcccac | 1500 |
| ctggtcccga cctttcactt cacctaccag ataataggat caggtggaaa | 1550 |
| gctctgccct ggtttctgtc cctgtggggt ttgcttctga tgggctgtgg | 1600 |
| cctgagcctg gccagtacca ggtgcctaca ggccaggtgc ttacactggc | 1650 |
| gacacaagtt gcttccccag tggatctggg agagggttcc tgatcctgcc | 1700 |
| aacagcaatt ctgggcaacc ttacatcaag gaggtgagcc tgccccaacc | 1750 |
| gcccaaggac ggaccccatcc tggaggtgga ggaagtggag ctacagcctg | 1800 |
| ttgtggagtc ccctaaagcc tctgccccga tttactctgg gtatgagaaa | 1850 |

-continued

```
cacttcctgc ccacaccaga ggagctgggc cttctagtct gatctgctta          1900
cggctagggg ctgtacccct atcttgggct agacgttcta gagtcgaccg          1950
cagaagcttg gccgccatgg cccaacttgt ttattgcagc ttataatgtt          2000
aaata                                                           2005

<210> SEQ ID NO 5
<211> LENGTH: 20
<212> TYPE: DNA
<213> ORGANISM: Mus musculus

<400> SEQUENCE: 5
tggtctctcc tggcaacagc                                           20

<210> SEQ ID NO 6
<211> LENGTH: 20
<212> TYPE: DNA
<213> ORGANISM: Mus musculus

<400> SEQUENCE: 6
agccaagcac accagagaca                                           20

<210> SEQ ID NO 7
<211> LENGTH: 21
<212> TYPE: DNA
<213> ORGANISM: Mus musculus

<400> SEQUENCE: 7
cagctgggtg cctcccacca a                                         21

<210> SEQ ID NO 8
<211> LENGTH: 20
<212> TYPE: DNA
<213> ORGANISM: Mus musculus

<400> SEQUENCE: 8
atccgcaagc ctgtgactgt                                           20

<210> SEQ ID NO 9
<211> LENGTH: 18
<212> TYPE: DNA
<213> ORGANISM: Mus musculus

<400> SEQUENCE: 9
tcgggccagg gtgttttt                                             18

<210> SEQ ID NO 10
<211> LENGTH: 18
<212> TYPE: DNA
<213> ORGANISM: Mus musculus

<400> SEQUENCE: 10
ttcccgggct cgttgccg                                             18

<210> SEQ ID NO 11
<211> LENGTH: 18
<212> TYPE: DNA
<213> ORGANISM: Mus musculus

<400> SEQUENCE: 11
tcgcgtctct gggaagct                                             18
```

```
<210> SEQ ID NO 12
<211> LENGTH: 24
<212> TYPE: DNA
<213> ORGANISM: Mus musculus

<400> SEQUENCE: 12
tttaagccaa tgtatccgag actg                                              24

<210> SEQ ID NO 13
<211> LENGTH: 20
<212> TYPE: DNA
<213> ORGANISM: Mus musculus

<400> SEQUENCE: 13
cgccagcgtc ctcctcgtgg                                                   20

<210> SEQ ID NO 14
<211> LENGTH: 21
<212> TYPE: DNA
<213> ORGANISM: Mus musculus

<400> SEQUENCE: 14
caagcatttg catcgctatc a                                                 21

<210> SEQ ID NO 15
<211> LENGTH: 19
<212> TYPE: DNA
<213> ORGANISM: Mus musculus

<400> SEQUENCE: 15
aatgcctttt gccggaagt                                                    19

<210> SEQ ID NO 16
<211> LENGTH: 24
<212> TYPE: DNA
<213> ORGANISM: Mus musculus

<400> SEQUENCE: 16
acgaattgag aacgtgccca ccgt                                              24
```